United States Patent
Bischof et al.

(10) Patent No.: US 10,604,457 B2
(45) Date of Patent: Mar. 31, 2020

(54) ETHYLENE OLIGOMERIZATION PROCESSES

(71) Applicant: Chevron Phillips Chemical Company LP, The Woodlands, TX (US)

(72) Inventors: Steven M. Bischof, Humble, TX (US); Brooke L. Small, Kingwood, TX (US); Ryan W. Snell, Kingwood, TX (US); Ron D. Knudsen, Bartlesville, OK (US); Eric J. Netemeyer, Bartlesville, OK (US); Orson L. Sydora, Houston, TX (US); Jamie N. Sutherland, Kingwood, TX (US); Bruce E. Kreischer, Kingwood, TX (US); William J. Fisher, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

(21) Appl. No.: 15/394,317

(22) Filed: Dec. 29, 2016

(65) Prior Publication Data
US 2018/0186709 A1    Jul. 5, 2018

(51) Int. Cl.
*C07C 2/32* (2006.01)
*C07C 2/34* (2006.01)
(Continued)

(52) U.S. Cl.
CPC ............ *C07C 2/34* (2013.01); *B01J 31/143* (2013.01); *B01J 31/2404* (2013.01); *C07C 2/36* (2013.01);
(Continued)

(58) Field of Classification Search
CPC .................................................. C07C 2/34
(Continued)

(56) References Cited

U.S. PATENT DOCUMENTS

| 5,451,645 A | 11/1995 | Raegen et al. |
| 5,955,555 A | 11/1999 | Bennett |

(Continued)

FOREIGN PATENT DOCUMENTS

| CA | 2020509 A1 | 2/1991 |
| CN | 104418690 A | 3/2015 |

(Continued)

OTHER PUBLICATIONS

Small, B. L. et. al. "Oligomerization of Ethylene Using New Tridentate Iron Catalysts Bearing α-Diimine Ligands with Pendant S and P Donors", Organometallics (2010), 29, pp. 6723-6731. (Year: 2010).*

(Continued)

*Primary Examiner* — Philip Y Louie
(74) *Attorney, Agent, or Firm* — Conley Rose, P.C.

(57) ABSTRACT

A process comprising a) contacting (i) ethylene, (ii) a catalyst system comprising 1) a heteroatomic ligand iron salt complex, or a heteroatomic ligand and an iron salt, (iii) hydrogen, and (iv) optionally an organic reaction medium; and b) forming an oligomer product wherein 1) the oligomer product has a Schulz-Flory K value from 0.4 to 0.8 and 2) the oligomer product comprises (a) less than 1 wt. % of polymer, (b) less than 1 wt. % compounds having greater than 70 carbon atoms, (c) less than 1 wt. % compounds having a weight average molecular weight of greater than 1000 g/mol, or (d) any combination thereof wherein the weight percentage is based on the total weight of the oligomer product.

23 Claims, 4 Drawing Sheets

(51) Int. Cl.
  *B01J 31/24* (2006.01)
  *B01J 31/14* (2006.01)
  *C07C 2/36* (2006.01)

(52) U.S. Cl.
  CPC ...... *B01J 2231/20* (2013.01); *B01J 2531/842* (2013.01); *C07C 2531/14* (2013.01); *C07C 2531/24* (2013.01); *Y02P 20/52* (2015.11)

(58) Field of Classification Search
  USPC .................................................. 585/502, 513
  See application file for complete search history.

(56) References Cited

U.S. PATENT DOCUMENTS

| | | | |
|---|---|---|---|
| 6,103,946 | A | 9/2000 | Brookhart, III et al. |
| 6,214,761 | B1 | 4/2001 | Bennett |
| 6,291,733 | B1 | 9/2001 | Small et al. |
| 6,417,305 | B2 | 7/2002 | Bennett |
| 6,423,848 | B2 | 7/2002 | Bennett |
| 6,432,862 | B1 | 8/2002 | Bennett |
| 6,451,939 | B1 | 9/2002 | Britovsek et al. |
| 6,455,660 | B1 | 9/2002 | Clutton et al. |
| 6,458,739 | B1 | 10/2002 | Kimberley et al. |
| 6,458,905 | B1 | 10/2002 | Schmidt et al. |
| 6,461,994 | B1 | 10/2002 | Gibson et al. |
| 6,472,341 | B1 | 10/2002 | Kimberly et al. |
| 6,489,497 | B1 | 12/2002 | Brookhart, III et al. |
| 6,534,691 | B2 | 3/2003 | Culver et al. |
| 6,545,108 | B1 | 4/2003 | Moody et al. |
| 6,555,723 | B2 | 4/2003 | Schiffino |
| 6,559,091 | B1 | 5/2003 | Moody et al. |
| 6,657,026 | B1 | 12/2003 | Kimberley et al. |
| 6,683,187 | B2 | 1/2004 | De Boer et al. |
| 6,710,006 | B2 | 3/2004 | De Boer et al. |
| 6,740,715 | B2 | 5/2004 | Brookhart, III et al. |
| 6,911,505 | B2 | 6/2005 | Small et al. |
| 6,911,506 | B2 | 6/2005 | Small et al. |
| 7,001,964 | B2 | 2/2006 | Small |
| 7,037,988 | B2 | 5/2006 | De Boer et al. |
| 7,045,632 | B2 | 5/2006 | Small |
| 7,049,442 | B2 | 5/2006 | De Boer et al. |
| 7,053,020 | B2 | 5/2006 | De Boer et al. |
| 7,053,259 | B2 | 5/2006 | Culver et al. |
| 7,056,997 | B2 | 6/2006 | Small et al. |
| 7,129,304 | B1 | 10/2006 | Small et al. |
| 7,223,893 | B2 | 5/2007 | Small et al. |
| 7,268,096 | B2 | 9/2007 | Small et al. |
| 7,271,121 | B2 | 9/2007 | Small et al. |
| 7,297,806 | B2 | 11/2007 | Brookhart, III et al. |
| 7,304,159 | B2 | 12/2007 | De Boer et al. |
| 7,442,819 | B2 | 10/2008 | Ionkin et al. |
| 7,456,284 | B2 | 11/2008 | Small |
| 7,683,149 | B2 | 3/2010 | Ionkin et al. |
| 7,902,415 | B2 | 3/2011 | Small |
| 7,994,376 | B2 | 8/2011 | Small et al. |
| 2002/0016425 | A1 | 2/2002 | De Boer et al. |
| 2005/0014983 | A1 | 1/2005 | De Boer et al. |
| 2005/0187418 | A1 | 8/2005 | Small et al. |
| 2007/0112150 | A1 | 5/2007 | Small et al. |
| 2007/0221608 | A1 | 9/2007 | Axe et al. |
| 2010/0274065 | A1 | 10/2010 | Sydora |
| 2013/0172651 | A1 | 7/2013 | Small |
| 2013/0211168 | A1 | 8/2013 | Breuil et al. |
| 2016/0229766 | A1 | 8/2016 | Sydora et al. |

FOREIGN PATENT DOCUMENTS

| | | |
|---|---|---|
| CN | 105884565 A | 8/2016 |
| EP | 1229020 A1 | 8/2002 |
| WO | 2004026795 A2 | 4/2004 |
| WO | 2005005354 A1 | 1/2005 |
| WO | 2010051415 A1 | 5/2010 |
| WO | 2011126787 A1 | 10/2011 |
| WO | 2013101387 A1 | 7/2013 |

OTHER PUBLICATIONS

Huang et al., "Effects of Hydrogen in Ethylene Polymerization and Oligomerization with Magnesium Chloride-Supported Bis(imino) pyridyl Iron Catalysts", Journal of Polymer Science: Part A: Polymer Chemistry, Wiley InterScience, vol. 45, 4054-4061, 2007. (Year: 2007).*
Agapie, T., "Selective ethylene oligomerization: Recent advances in chromium catalysis and mechanistic investigations," Coordination Chemistry Reviews, 2011, vol. 255, pp. 861-880, Elsevier B.V.
Bennett, A. et al., "Novel, highly active iron and cobalt catalysts for olefin polymerization," Chemtech, Jul. 1999, pp. 24-28, vol. 29, American Chemical Society.
Britovsek, G. et al., "Iron and Cobalt Ethylene Polymerization Catalysts bearing 2,6-Bis(imino)Pyridyl Ligands: Synthesis, Structures and Polymerization Studies," Journal of the American Chemical Society, 1999, pp. 8728-8740, vol. 121, American Chemical Society.
Britovsek, G. et al., "Novel olefin polymerization catalysts based on iron and cobalt," Chemical Communication, 1998, pp. 849-850, vol. 7.
Britovsek, G. et al., "Oligomerization of Ethylene by Bis(imino)pyridyliron and —cobalt Complexes," Chemistry—A European Journal, 2000, pp. 2221-2231, vol. 6, No. 12, Wiley-VCH.
Chen, Y., et al., "Fluoro-Substituted 2,6-Bis(imino)pyridyl Iron and Cobalt Complexes: High-Activity Ethylene Oligomerization Catalysts," Organometallics, 2003, pp. 1231-1236, vol. 32, American Chemical Society.
Chen, Y., et al., Halogen-Substituted 2,6-Bis(imino)pyridyl Iron and cobalt Complexes: Highly Active Catalysts for Polymerization and Oligomerization of Ethylene, Organometallics, 2003, pp. 4312-4321, vol. 22, American Chemical Society.
Dixon, J., et al., "Advances in selective ethylene trimerisation—a critical overview," Journal of Organometallic Chemistry, 2004, vol. 689, pp. 3641-3668, Elsevier B. V.
Filing Receipt and Specification of U.S. Appl. No. 15/394,411, filed Dec. 29, 2016, entitled, "Ethylene Oligomerization Processes," 73 pages.
Ionkin, A., et al., "High-Temperature Catalysts for the Production of α-Olefins Based on Iron(II) and Cobalt(II) Tridentate Bis(imino)pyridine Complexes with a Double Pattern of Substitution: o-Methyl plus o-Fluorine in the Same Imino Arm," Organometallics, 2008, pp. 1147-1156, vol. 27, American Chemical Society.
Ionkin, A., et al., "High-Temperature Catalysts for the Production of α-Olefins Based on Iron(II) and Iron(III) Tridentate Bis(imino)pyridine Complexes Modified by Nitrilo Group," J. Poly. Sci.: Part A Poly. Chem., 2008, pp. 585-611, vol. 46.
Ionkin, A., et al., "High-Temperature Catalysts for the Production of α-Olefins Based on Iron(II) and Iron(III) Tridentate Bis(imino)pyridine Complexes with Double Pattern of Substitution: ortho-Methyl plus meta-Aryl," Organometallics, 2006, pp. 2987-2992, vol. 25, American Chemical Society.
Ionkin, A., et al., "Modification of Iron(II) Tridentate Bis(imino)pyridine Complexes by a Boryl Group for the Production of α-Olefins at High Temperature," Organometallics, 2008, pp. 1902-1911, vol. 27, American Chemical Society.
Manyik, R., et al., "A Soluble Chromium-based Catalyst for Ethylene Trimerization and Polymerization," Journal of Catalysis, 1977, vol. 47, pp. 197-209, Academic Press, Inc.
McNaught, Alan D., et al., "Compendium of Chemical Terminology," IUPAC Recommendations, Second edition, 1997, 5 pages, Wiley-Blackwell. (To cite per Edith Feb. 20, 2017).
Schmiege, B., et al., "Alternatives to pyridinediimine ligands: syntheses and structures of metal complexes supported by donor-modified α-diimine ligands," Dalton Transactions, 2007, vol. 24, pp. 2547-2562, Royal Society of Chemistry.
Small, B. et al., "Highly Active Iron and Cobalt Catalysts for the Polymerization of Ethylene," Journal of the American chemical Society, 1998, pp. 4049-4050, vol. 120, American Chemical Society.
Small, B. et al., "Iron-Based Catalysts with Exceptionally High Activities and Selectivities for Oligomerization of Ethylene to

(56) References Cited

OTHER PUBLICATIONS

Linear α-Olefins," Journal of the American Chemical Society, 1998, pp. 7143-7144, vol. 120, American Society.

Small, B. et al., "Polymerization of Propylene by a New Generation of Iron Catalysts: Mechanisms of Chain Initiation, Propagation, and Termination," Macromolecules, Oct. 29, 1999, pp. 2120-2130, vol. 32, American Chemical Society.

Small, B., et al., "Oligomerization of Ethylene using New Iron Catalysts Bearing Pendant Donor Modified α-Diimine Ligands," Organometallics, 2007, vol. 26, pp. 1744-1749, American Chemical Society.

Small, B., et al., "Oligomerization of Ethylene Using New Tridentate Iron Catalysts Bearing α-Diimine Ligands with Pendant S and P Donors," Organometallics, 2010, vol. 29, pp. 6723-6731, American Chemical Society.

Zhang, Z., et al., "Ethylene oligomerization catalyzed by a novel iron complex containing fluoro and methyl substituents," Journal of Molecular catalysis A: Chemical, 2004, pp. 249-254, vol. 219, Elsevier B.V.

"Group notation revised in periodic table," Feb. 4, 1985, C&EN, p. 27.

Boudier, Adrien, et al., "Novel Catalytic System for Ethylene Oligomerization: An Iron(III) Complex with an Anionic N, N,N Ligand," Organometallics, 2011, vol. 30, pp. 2640-2642, American Chemical Society.

Receipt and Specification of U.S. Appl. No. 15/852,623, filed Dec. 22, 2017, by Steven Bischof, et al. and entitled "Ethylene Oligomerization Processes."

Receipt and specification for international application entitled "Ethylene Oligomerization Processes," by Steven Bischof, et al., filed Dec. 22, 2017 as serial No. PCT/US2017/068274.

Receipt and specification for international application entitled "Ethylene Oligomerization Processes," by Steven Bischof, et al., filed Dec. 22, 2017 as serial No. PCT/US2017/068278.

Receipt and specification for international application entitled "Ethylene Oligomerization Processes," by Steven Bischof, et al., filed Dec. 22, 2017 as serial No. PCT/US2017/068281.

Sun, Wen-Hua, et al., "Iron Complexes Bearing 2-Imino-1,10-phenanthrolinyl Ligands as Highly Active Catalysts for Ethylene Oligomerization," Organometallics, 2006, vol. 25, pp. 666-677, American Chemical Society.

Foreign communication from a related application—International Search Report and Written Opinion, PCT/US2017/068278, dated May 30, 2018, 18 pages.

Office Action dated Feb. 8, 2018 (44 pages), U.S. Appl. No. 15/394,411, filed Dec. 29, 2016.

Office Action dated Feb. 8, 2018 (58 pages), U.S. Appl. No. 15/852,623, filed Dec. 22, 2017.

Foreign communication from a counterpart application—Invitation to Pay Additional Fees and Partial Search Report, PCT/US2017/068278, dated Apr. 9, 2018, 14 pages.

Foreign communication from a counterpart application—International Search Report and Written Opinion, PCT/US2017/068281, dated Apr. 9, 2018, 13 pages.

Walsh, R., et al., "Tetramerisation Process Technology Review," The IP.com Prior Art Database, Jul. 13, 2004, Sasol Technology (Pty) Ltd, 28 pages.

Foreign communication from a related application—International Search Report and Written Opinion, PCT/US2017/068274, dated Jun. 7, 2018, 23 pages.

\* cited by examiner

ETHYLENE OLIGOMERIZATION PROCESSES

CROSS-REFERENCE TO RELATED APPLICATIONS

Not applicable.

FIELD

The present disclosure relates to processes for producing alpha olefins. More particularly, the present disclosure relates to improved processes for oligomerizing ethylene.

BACKGROUND

Alpha olefins are important items of commerce. Their many applications include employment as intermediates in the manufacture of detergents, as precursors to more environmentally friendly refined oils, as monomers, and as precursors for many other types of products. One method of making alpha olefins is via oligomerization of ethylene in a catalytic reaction involving various types of catalysts and/or catalyst systems. Examples of catalysts and catalyst systems used commercially to produce alpha olefins include alkylaluminum compounds, certain nickel-phosphine complexes, titanium halides with a Lewis acid (e.g., diethyl aluminum chloride), zirconium halides and/or zirconium alkoxides with alkylaluminum compounds. Additionally, there is a selective ethylene trimerization and/or tetramerization catalyst system for producing 1-hexene that uses a chromium containing compound (e.g., a chromium carboxylate), a nitrogen-containing ligand (e.g., a pyrrole), and a metal alkyl (e.g., alkyl aluminum compounds).

Several non-commercial oligomerization catalyst systems to produce alpha olefins are based upon metal complexes of pyridine bis-imines, metal complexes of amine compounds having a metal complexing group, and selective trimerization and/or tetramerization catalyst systems using a metal compound (e.g., a chromium compound) complex of a diphosphinylamine, phosphinyl formamidine, phosphinyl amidine, or phosphinyl guanidine. These catalyst systems typically use an organoaluminum compound (e.g., aluminoxane) as a component of the catalyst systems for olefin oligomerization.

Applications and demand for olefins (e.g., alpha olefins) continue to multiply, and competition to supply them correspondingly intensifies. Thus, additional novel and improved catalyst systems and processes for olefin oligomerization are desirable.

SUMMARY

Disclosed herein is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product wherein 1) the oligomer product has a Schulz-Flory K value from 0.4 to 0.8 and 2) the oligomer product comprises (a) less than 1 wt. % of polymer, (b) less than 1 wt. % compounds having greater than 70 carbon atoms, (c) less than 1 wt. % compounds having a weight average molecular weight of greater than 1000 g/mol, or (d) any combination thereof wherein the weight percentage is based on the total weight of the oligomer product.

Also disclosed herein is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product wherein 1) the oligomer product has a Schulz-Flory K value from 0.4 to 0.8, and 2) each of a single carbon number oligomer product fractions has a paraffin content equal to or less than 2 times of the paraffin content of a corresponding single carbon number oligomer product produced in the absence of hydrogen wherein the weight percentage is based on the total weight of the single carbon number oligomer product.

Also disclosed herein is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product having a Schulz-Flory K value of from 0.4 to 0.8 with a value that is within ±5% of an oligomer product produced in the absence of hydrogen.

DETAILED DESCRIPTION

Figure 1:
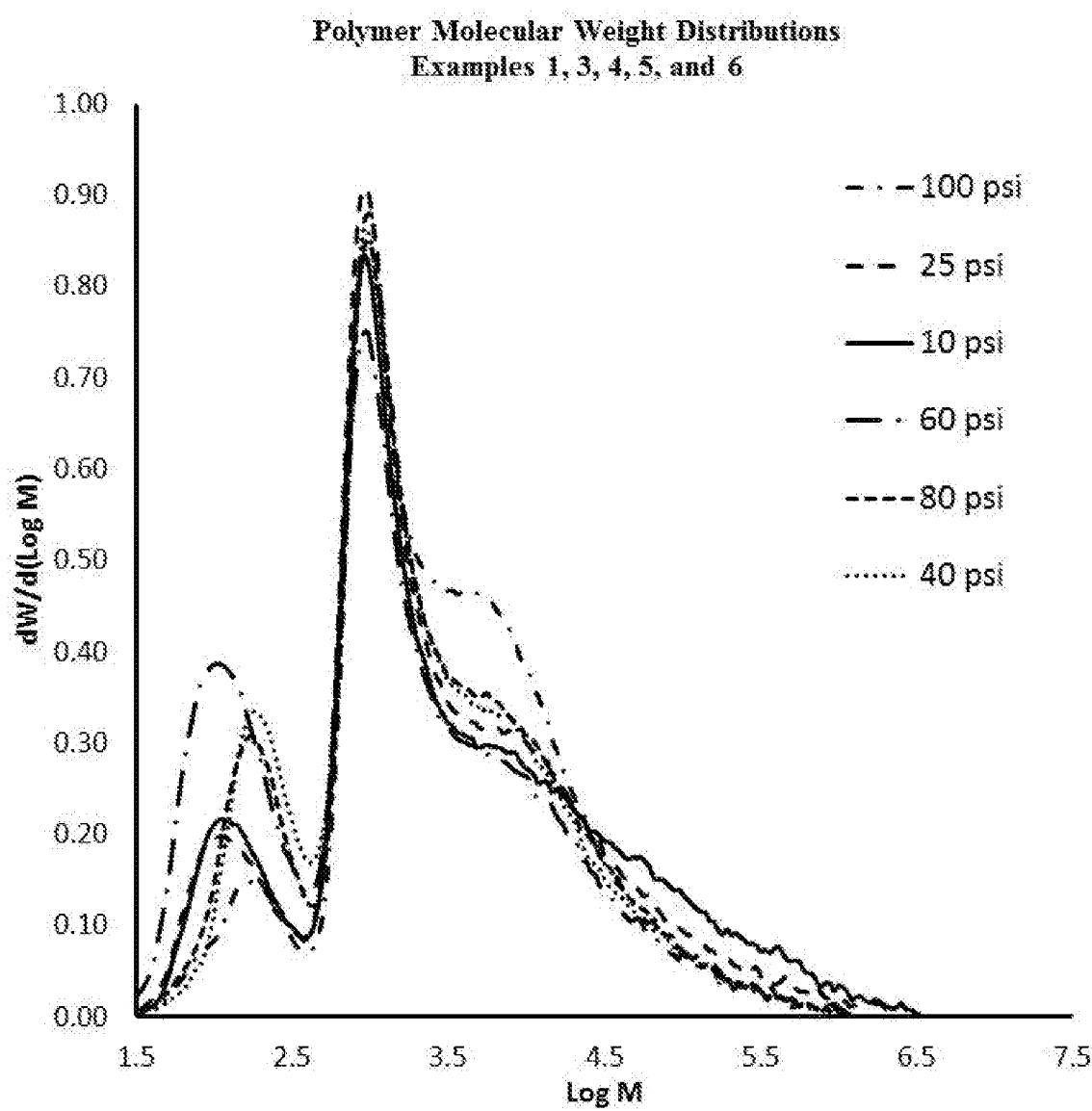
FIG. 1 provides a plot of the molecular weight of the polymer produced in Examples 1, 3, 4, 5, and 6.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in Chemical and Engineering News, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements, among others.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively, consist of specific steps and/or utilize a catalyst system comprising recited components and other non-recited components.

While compositions and methods are described in terms of "comprising" various components or steps, the compositions and methods can also "consist essentially of" or "consist of" the various components or steps.

In the specification and claims, the terms "a," "an," and "the" are intended, unless specifically indicated otherwise, to include plural alternatives, e.g., at least one, or one or more. For instance, the disclosure of "a trialkylaluminum compound" is meant to encompass one trialkylaluminum compound, or mixtures or combinations of more than one trialkylaluminum compound unless otherwise specified. In another instance, the disclosure using a specified material of a can be interpreted as comprising (consisting essentially of, or consisting of) at least one of the specified material, or can be interpreted as comprising (consisting essentially of, or consisting of) one of more of the specified materials. For example, in general, a claim feature reciting "consisting essentially of a $C_6$ to $C_{16}$ compound" can be interpreted or rewritten to recite "consisting essentially of at least one $C_6$ to $C_{16}$ compound," or "consisting essentially of one or more $C_6$ to $C_{16}$ compounds."

In this disclosure, the terms first, second, and third, among others, can be utilized to differentiate multiple occurrences of a similar element. For example a method can utilize two or more solvents in different steps of a method, or alternatively, two different solvents in a mixture. The differentiating term can be applied to any element described herein when necessary to provide a differentiation. It should be understood that the numerical or alphabetical precedence of the differentiating terms do not imply a particular order or preference of the element in a method or compound described herein unless specifically specified otherwise.

In this disclosure, a process can have multiple steps or can include features having a number of different elements (e.g., components in a catalyst system or components in an olefin oligomerization process, among other features). These steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to a $C_6$ hydrocarbon refers to all hydrocarbon having 6 carbon atoms, a general reference to pentane includes n-pentane, 2-methylbutane, and 2,2-dimethylpropane, and a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth.

For the purposes of this application, the term or variations of the term "organyl group consisting essentially of inert functional groups" refers to an organyl group (having a free valence on a carbon atom) wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting essentially of inert functional groups" further defines the particular organyl groups that can be present within the organyl group consisting essentially of inert functional groups. Additionally, the term "organyl group consisting essentially of inert functional groups" can refer to the presence of one or more inert functional groups within the organyl group. The term or variation of the term "organyl group consisting essentially of inert functional groups" definition includes the hydrocarbyl group as a member (among other groups). Similarly, an "organylene group consisting essentially of inert functional groups" refers to an organic group formed by removing two hydrogen atoms from one or two carbon atoms of an organic compound consisting of inert functional groups and an "organic group consisting essentially of inert functional groups" refers to a generalized organic group consisting essentially of inert functional groups formed by removing one or more hydrogen atoms from one or more carbon atoms of an organic compound consisting of inert functional groups.

For purposes of this application, an "inert functional group" is a group having a free valence on a heteroatom which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while a hydrocarboxy group can complex with a metal compound, a hydrocarboxy group located at a para position of a substituted pyridine ring or the para position of a substituted imine phenyl group can be an inert functional group because a single metal compound molecule cannot complex with the three nitrogen atoms of a bis(imine) pyridine ligand and the para hydrocarboxy group within the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include a halide (fluoride, chloride, bromide, and iodide), nitro, hydrocarboxy groups (e.g., alkoxy, and/or aroxy, among others), and/or hydrocarbosulfidyl groups (e.g., RS—), among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc . . . endocyclic double or triple bonds, respectively, can be identified by use of the term "mono," "di," "tri, etc . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

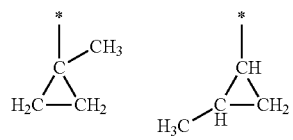

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to hydrocarbon compounds that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. carbon-carbon double bonds can be identified by use of the term "mono," "di," "tri," etc. within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. such multiple bonds can be identified by use of the term "mono," "di," "tri," etc. within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane).

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "primary carbon atom group," a "secondary carbon atom group," a "tertiary carbon atom group," and a "quaternary carbon atom group" describe the type of carbon atom which would be created when the group is attached to a base structure. A "primary carbon atom group" is a group wherein the carbon atom bonded to the base structure is also bonded to three monovalent atoms (e.g., hydrogen or halides) in addition to the base structure. A methyl group, a trifluormethyl group (among other group) attached to a base structure represent potential "primary carbon atom groups." A "secondary carbon atom group" is a group wherein the carbon atom bonded to the base structure is bonded to one other non-monovalent atom (e.g., carbon, nitrogen, or oxygen, among others) and two monovalent atoms. An ethyl group, a 1-chloroeth-1-yl group, and a methoxymethyl group (among others) attached to a base structure represent potential "secondary carbon atom groups." A "tertiary carbon group" is a group wherein the carbon atom bonded to the base structure is bonded to two other non-monovalent atoms and one monovalent atom. An isopropyl group, a 2-chloroprop-1-yl group, a phenyl group, and a 1-methoxyethy-1-yl group (among others) attached to a base structure represent potential "tertiary carbon groups." A "quaternary carbon group" is a group wherein the carbon atom bonded to the base structure is also bonded to three other non-monovalent atoms. A tert-butyl group and a 2-methoxyprop-2-yl group (among others) attached to a base structure represent potential "quaternary carbon groups."

A "halide" has its usual meaning; therefore, examples of halides include fluoride, chloride, bromide, and iodide.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4-position refers to a group having a non-hydrogen atom at the 4-position and hydrogen or any other non-hydrogen group at the 2-, 3-, 5-, and 6-positions.

The term "reaction zone effluent," and it derivatives (e.g., oligomerization reaction zone effluent) generally refers to all the material which exits the reaction zone. The term "reaction zone effluent," and its derivatives, can also be prefaced with other descriptors that limit the portion of the reaction zone effluent being referenced. For example, the term "reaction zone effluent" would refer to all material exiting the reaction zone (e.g., product and solvent or diluent, among others), while the term "olefin reaction zone effluent" refers to only the olefins within the reaction zone effluent and the term "oligomer product reaction zone effluent" refers to oligomer product within the reaction zone effluent.

The term "oligomerization," and its derivatives, refers to processes which produce a mixture of products containing at least 70 wt. % products containing from 2 to 30 monomer units. Similarly, an "oligomer" is a product that contains from 2 to 30 monomer units while an "oligomer product" or an "oligomerization product" includes all products made by the "oligomerization" process including the "oligomers" and products which are not "oligomers" (e.g., product which contain more than 30 monomer units). It should be noted that the monomer units in the "oligomer" or "oligomerization product" do not have to be the same. For example, an "oligomer," "oligomer product," or "oligomerization product" of an "oligomerization" process using ethylene and propylene as monomers can contain both ethylene and/or propylene units.

K value (sometimes referred to as Schulz-Flory chain growth factor, K, or Schulz-Flory K value) can be defined the equation: $K=X_{q+1}/X_q$ wherein $X_{q+1}$ is the number of moles of oligomer product produced having q+1 monomer (e.g., ethylene) units and $X_q$ is the number of moles of oligomer product produced having q monomer (e.g., ethylene) units. Generally, the Schulz-Flory K value can be determined using any two oligomers of the oligomer product which differs in the number of monomer units by 1. However, one would appreciate that product isolation and analysis can lead to inaccuracies in a determined oligomer product distribution using particular oligomers (e.g., incomplete recovery of gaseous product and/or solid product during product isolation). One having ordinary skill in the art would recognize such issues and can choose the appropriate oligomers upon which to base the determination of the Schulz-Flory K value.

Catalyst system productivity is defined as grams of a product produced per gram (or mole) of metal in the catalyst system utilized in the oligomerization. Catalyst system activity is defined as grams of a product produced per gram (or mole) of metal of the metal utilized per unit of time (e.g., hour) of an oligomerization. Catalyst system productivity and/or activity can be stated in terms of various products of an oligomerization and/or components of catalyst system. For example, in an ethylene oligomerization process utilizing a catalyst system comprising an iron salt complex and an organoaluminum compound, the catalyst system productivity which can be utilized include (g oligomer product)/(g Fe), among other productivities.

Unless otherwise specified, the terms "contacted," "combined," and "in the presence of" refer to any addition sequence, order, or concentration for contacting or combining the recited two or more components. The combining or contacting of the components, according to the various methods described herein can occur in one or more contact zones under suitable contact conditions such as temperature, pressure, contact time, flow rates, etc. . . . The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact, unless otherwise specified. The processes can be carried out in a batch or continuous process as is suitable for a given aspect, unless otherwise specified.

The terms "simultaneously," "simultaneously contact," "contact simultaneously," and their derivatives when referring to a contact method refers to a contact method wherein the two or more recited compounds, mixtures, streams, and/or compositions are contacted by flowing into a common junction, pot, vessel, or reactor, among others, at the same time. The terms "substantially simultaneously," "substantially simultaneously contact," "contact substantially simultaneously," and their derivatives when referring to a contact method refers to a contact method wherein, during the contact of two or more recited compounds, mixtures, streams, and/or compositions, the two or more recited compounds, mixtures, streams, and/or compositions are contacted such that for some period during the contact process the two or more recited compounds, mixtures, streams, and/or compositions flow into a common junction, pot, vessel, or reactor at the same time. It should be noted that the terms "substantially simultaneously," "substantially simultaneously contact," "contact substantially simultaneously," and their derivatives do not mean that the two or more recited compounds, mixtures, streams, and/or compositions are contacted simultaneously over the entire addition of each of the two or more recited compounds, mixtures, streams, and/or compositions. The terms "substantially simultaneously," "substantially simultaneously contact," "contact substantially simultaneously," and it derivatives include scenarios where the flow of one of the (or less than all of the) recited compounds, mixtures, streams, and/or compositions can be initiated into the common junction, pot, vessel, or reactor before the others and/or the flow of one of the (or less than all of the) recited compounds, mixtures, streams, and/or compositions into the common junction, pot, vessel, or reactor can be completed, stopped, or discontinued before the other recited compounds, mixtures, streams, and/or compositions. In any aspect and/or embodiment described herein, the terms "simultaneously," "simultaneously contact," "contact simultaneously," and their derivatives, can be modified by the inclusion of a term providing a quantity of the each of the recited compounds, mixtures, streams, and/or compositions which can be contacted simultaneously indicate scenarios of various degrees of "substantially simultaneously," "substantially simultaneously contact," "contact substantially simultaneously," and their derivatives. For example, at least 20%, 30%, 40%, 50%, 60%, 70%, 75%, 80%, 85%, 90%, 95% of each of the recited compounds, mixtures, streams, and/or compositions can be "simultaneously contacted" or "contacted simultaneously." Generally, the percentages of the recited compounds, mixtures, streams, and/or compositions that can be "simultaneously contacted" or "contacted simultaneously" can be by weight (wt. %), by volume (volume %), or by mole (mole %). Unless otherwise specified, recited compounds, mixtures, streams, and/or compositions that are "substantially simultaneously," "substantially simultaneously contact," "contact substantially simultaneously," and their derivatives shall mean that at least 50% of each of the recited compounds, mixtures, streams, and/or compositions can be "simultaneously contacted" or "contacted simultaneously."

It should be further noted, that in reference to contact method or process, "simultaneously," "simultaneously contact," "contact simultaneously," "substantially simultaneously contact," "contact substantially simultaneously," and their derivatives is different than a process or method wherein one or more a first materials (e.g., compound, mixture, stream, and/or composition) already resides in a pot, vessel, or reactor and one or more other compounds, mixtures, streams, and/or compositions are added to the pot, vessel, or reactor. In this instance the first material in the pot, vessel, or reactor does not flow into the pot, vessel, or reactor concurrently with the other compounds, mixtures, streams, and/or compositions and the material in the pot. Thus, the first material and the other compounds, mixtures, streams, and/or compositions cannot be said to be "simultaneously contacted," "contacted simultaneously," "substantially simultaneously contacted," or "contacted substantially simultaneously." with the other component(s).

The processes disclosed herein can relate to processes comprising a) contacting (i) ethylene, (ii) a catalyst system comprising a heteroatomic ligand iron salt complex, or a heteroatomic ligand and an iron salt, and (iii) hydrogen; and b) forming an oligomer product. In an aspect, the processes can comprise a) contacting (i) ethylene, (ii) a catalyst system comprising 1) a heteroatomic ligand iron salt complex, or a heteroatomic ligand and an iron salt and 2) an organoaluminum compound, and (iii) hydrogen; and b) forming an oligomer product. Optionally, the ethylene, catalyst system and hydrogen can be contacted with an, at least one, or one or more, organic reaction medium (s). In an aspect, the oligomer product can be formed in a reaction zone. In an aspect, the oligomer product can be form at, the reaction zone can have, or the reaction zone can operate at conditions capable of forming an oligomer product. Generally, the heteroatomic ligand iron salt of the catalyst system, the heteroatomic ligand of the catalyst system, the iron salt of the catalyst system, the organoaluminum compound which can be utilized in the catalyst system, the optional organic reaction medium, the reaction zone, the conditions at which the oligomer product can be formed, the conditions which the reaction zone can have, and/or the conditions at which the reaction zone can operate, where applicable, are independent elements of process described herein and are independently described herein. These independently described process elements can be utilized in any combination, and without limitation, to further describe the processes provided herein.

In an aspect, the processes described herein can produce an oligomer product wherein the oligomer product has a particular Schulz-Flory K value. In further aspects, the oligomer product produced by the process described herein can form an oligomer product wherein 1) the oligomer product comprises (a) less than a specified amount of polymer, (b) less than a specified amount of compounds having greater than 70 carbon atoms, (c) less than a specified amount of compounds having a weight average molecular weight of greater than 1000 g/mol, or (d) any combination thereof wherein the weight percentage is based on the total weight of the oligomer product, 2) each of a single carbon number oligomer product fraction from $C_4$ to $C_{18}$ has a paraffin content equal to or less than a specified paraffin content of a corresponding single carbon number oligomer product fraction produced by a similar process operating in the substantial absence of hydrogen based on the total weight of the oligomer product fraction, 3) the oligomer product has a Schulz-Flory K value that is within a specified range of the Schulz-Flory K value of a corresponding oligomer product produced by a similar process operating in the substantial absence of hydrogen, 4) or any combination thereof. In some embodiments, the oligomer product produced by the process described herein can form an oligomer product wherein the oligomer product comprises (a) less than a specified amount of polymer, (b) less than a specified amount of compounds having greater than 70 carbon atoms, (c) less than a specified amount of compounds having a weight average molecular weight of greater than 1000 g/mol, or (d) any combination thereof wherein the weight percentage is based on the total weight of the oligomer product; alternatively, each of a single carbon number oligomer product fraction from $C_4$ to $C_{18}$ has a paraffin content equal to or less than a specified paraffin content of a corresponding single carbon number oligomer product fraction produced by a similar process operating in the substantial absence of hydrogen based on the total weight of the oligomer product fraction; or alternatively, 3) the oligomer product has a Schulz-Flory K value that is within a specified range of the Schulz-Flory K value of a corresponding oligomer product produced by a similar process operating in the substantial absence of hydrogen. The specified amount of polymer, the specified amount of compounds having greater than 70 carbon atoms, the specified amount of compounds having a weight average molecular weight of greater than 1000 g/mol, the specified paraffin content, and the specified range of the Schulz-Flory K value are independent elements of the processes described herein and are independently described herein. These independently described process elements can be utilized in any combination, and without limitation, to further describe the processes provided herein.

In an aspect, a catalyst system used in the processes can comprise a heteroatomic ligand iron salt complex; or alternatively, a heteroatomic ligand and an iron salt. In an aspect the heteroatomic ligand iron salt complex of the catalyst system can be an αmine iron salt complex or a pyridine bisimine iron salt complex; alternatively, an αmine iron salt complex; or alternatively, a pyridine bisimine iron salt complex. In an aspect, the heteroatomic ligand of the catalyst utilizing a heteroatomic ligand and an iron salt can be a pyridine bisimine. Generally, the α-diimine iron salt complex, the α-diimine of the α-diimine iron salt complex, the pyridine bisimine iron salt complex, the iron salt, and the iron salt of the α-diimine iron salt complex or the pyridine bisimine iron salt complex are independent elements of the catalyst systems utilized in the processes described herein and are independently described herein. These, independently described catalyst system elements can be utilized in any combination, and without limitation, to further describe the catalyst systems utilized in processes provided herein.

In various aspects and embodiments, an α-diimine iron salt complex can be utilized in the processes described herein. Generally, the α-diimine iron salt complex can be any α-diimine iron salt complex that when contacted with ethylene and any other appropriate reagent(s) under the appropriate conditions can form an oligomer product. Generally, the α-diimine and the iron salt of the α-diimine iron salt complex are independent elements of the α-diimine iron salt complex and are independently disclosed herein. The independent descriptions of the α-diimine and the iron salt of the α-diimine iron salt complex can be used without limitation, and in any combination, to further describe the α-diimine iron salt complex that can be introduced into the reaction in some aspects and/or embodiments of the processes described herein. In an aspect, the α-diimine iron salt complex can comprise only one α-diimine group; alternatively, at least two α-diimine groups; or alternatively, the α-diimine can comprise only two α-diimine groups.

Generally, the α-diimine of the α-diimine iron salt complex can be described as comprising i) an α-diimine group, ii) a first imine nitrogen group attached to a first imine nitrogen atom of the α-diimine group, and iii) a second imine nitrogen group attached to a second imine nitrogen atom of the α-diimine group. The α-diimine group, first imine nitrogen group, and second imine nitrogen group are independent elements of the α-diimine and each of these elements are independently described herein. The independent elements of the α-diimine can used without limitation, and in any combination, to further describe the α-diimine and the α-diimine element of the α-diimine iron salt complex.

In an aspect, the α-diimine of the α-diimine iron salt complex can be a bidentate α-diimine or a tridentate α-diimine; alternatively, a bidentate α-diimine; or alternatively, a tridentate α-diimine. It should be noted that the tridentate α-diimine description does not necessarily imply that all of the ligating elements of the tridentate α-diimine complex to the iron salt.

In an aspect, the α-diimine group of the α-diimine can be derived from an α-diacyl compound; or alternatively, an α-dione. Consequently, in some aspects, the α-diimine of the α-diimine iron salt complex can be described as comprising i) an α-diimine group derived from an α-diacyl compound, ii) a first imine nitrogen group attached to a first imine nitrogen atom of the α-diimine group, and iii) a second imine nitrogen group attached to a second imine nitrogen atom of the α-diimine group; or alternatively, the α-diimine of the α-diimine iron salt complex can be described as comprising i) an α-diimine group derived from an α-dione, ii) a first imine nitrogen group attached to a first imine nitrogen atom of the α-diimine group, and iii) a second imine nitrogen group attached to a second imine nitrogen atom of the α-diimine group. In an aspect, the α-diacyl compound (or α-dione) can be an aliphatic α-diacyl compound (or aliphatic α-dione) or an aromatic α-diacyl compound (or aromatic α-dione); alternatively, an aliphatic α-diacyl compound (or aliphatic α-dione); or alternatively, an aromatic α-diacyl compound (or aromatic α-dione). In other aspects, the α-diacyl compound (or α-dione), whether it is aliphatic or aromatic, can be a cyclic α-diacyl compound (or cyclic α-dione) or an acyclic α-diacyl compound (or acyclic α-dione); alternatively, a cyclic α-diacyl compound (or cyclic α-dione); or alternatively, an acyclic α-diacyl compound (or acyclic α-dione). In any aspect or embodiment disclosed herein, the α-diacyl compound (or α-dione), whether it is aliphatic or aromatic and/or cyclic or acyclic, can be a $C_4$ to $C_{60}$ α-diacyl compound (or $C_4$ to $C_{60}$ α-dione), a $C_4$ to $C_{45}$ α-diacyl compound (or $C_4$ to $C_{45}$ α-dione), a $C_4$ to $C_{30}$ α-diacyl compound (or $C_4$ to $C_{30}$ α-dione), or $C_4$ to $C_{20}$ α-diacyl compound (or $C_4$ to $C_{20}$ α-dione).

Generally, the α-dione can have the structure $R^{k1}$—C(=O)—C(=O)—$R^{k2}$. In an aspect, $R^{k1}$ and $R^{k2}$ independently can be an organyl group; alternatively, an organyl group consisting essentially of inert functional groups; or alternatively, a hydrocarbyl group. In any aspect or embodiment disclosed herein, the organyl groups which can be utilized as $R^{k1}$ and/or $R^{k2}$ can be a $C_1$ to $C_{30}$, a $C_1$ to $C_{20}$, a $C_1$ to $C_{15}$, a $C_1$ to $C_{10}$, or a $C_1$ to $C_5$ organyl group. In any aspect or embodiment disclosed herein, the organyl groups consisting essentially of inert functional groups which can be utilized as $R^{k1}$ and/or $R^{k2}$ independently can be a $C_1$ to $C_{30}$, a $C_1$ to $C_{20}$, a $C_1$ to $C_{15}$, a $C_1$ to $C_{10}$, or a $C_1$ to $C_5$ organyl group consisting essentially of inert functional groups. In any aspect or embodiment disclosed herein, the hydrocarbyl groups which can be utilized as $R^{k1}$ and/or $R^{k2}$ independently can be a $C_1$ to $C_{30}$, a $C_1$ to $C_{20}$, a $C_1$ to $C_{15}$, a $C_1$ to $C_{10}$, or a $C_1$ to $C_5$ hydrocarbyl group. In any aspect or embodiment disclosed herein, the hydrocarbyl groups which can be utilized as $R^{k1}$ and/or $R^{k2}$ independently can be a $C_1$ to $C_{30}$, $C_1$ to $C_{20}$, a $C_1$ to $C_{15}$, a $C_1$ to $C_{10}$, or a $C_1$ to $C_5$ alkyl group.

In an aspect, the α-dione from which the α-diimine group of the α-diimine can be derived can be an acyclic α-dione, a semicyclic α-dione, or a cyclic α-dione; alternatively, an acyclic α-dione; alternatively, a semicyclic α-dione; or alternatively, a cyclic α-dione. When the α-dione is an acyclic α-dione, both $R^{k1}$ and $R^{k2}$ are acyclic. When the α-dione is a semi-cyclic α-dione, $R^{k1}$ and/or $R^{k2}$ are or can comprise a cyclic structure wherein $R^{k1}$ and $R^{k2}$ are not connected to form a ring or ring system containing both ketone carbon atoms of the α-dione group. When the α-dione is a cyclic α-dione, $R^{k1}$ and $R^{k2}$ are connected to form a ring or ring system containing both ketone carbon atoms of the α-dione group. In some semi-cyclic and/or cyclic α-dione aspects, the ring or ring system(s) can be saturated. In other semi-cyclic and/or cyclic α-dione aspects, the ring or ring system(s) can contain carbon-carbon double (and/or triple) bonds. In further semi-cyclic and/or cyclic α-dione aspects, the ring or ring system(s) can be a bicyclic ring system. In yet other semi-cyclic and/or cyclic α-dione aspects, the ring or ring system(s) can comprise an aromatic ring or an aromatic ring structure.

In an acyclic α-dione aspect, the α-dione can be 2,3-butanedione, a substituted 2,3-butanedione, 2,3-pentanedione, a substituted 2,3-pentanedione, 2,3-hexanedione, a substituted 2,3-hexanedione, 3,4-hexanedione, or a substituted 3,4-hexanedione. In some aspects, the α-dione can be 2,3-butanedione, 2,3-pentanedione, 2,3-hexanedione, or 3,4-hexanedione. In further aspects, the α-dione can be 2,3-butanedione; alternatively, 2,3-pentanedione; alternatively, 2,3-hexanedione; or alternatively, 3,4-hexanedione.

In an aromatic semi-cyclic α-dione aspect, the α-dione can be benzil or a substituted benzil. In other aspects, the α-dione can be benzil.

In a saturated cyclic α-dione aspect, the α-dione can be 1,2-cyclobutanedione, a substituted 1,2-cyclobutanedione, 1,2-cyclopentanedione, a substituted 1,2-cyclopentanedione, 1,2-cyclohexanedione, a substituted 1,2-cyclohexanedione, 1,2-cycloheptanedione, or a substituted 1,2-cycloheptanedione. In some saturated cyclic α-dione aspects, the α-dione can be 1,2-cyclopentanedione, a substituted 1,2-cyclopentanedione, 1,2-cyclohexanedione, or a substituted 1,2-cyclohexanedione. In some saturated cyclic α-dione aspects, the α-dione can be 1,2-cyclopentanedione, or 1,2-cyclohexanedione. In yet other aspects, the α-dione can be 1,2-cyclopentanedione; or alternatively, 1,2-cyclohexanedione.

In saturated ring system α-dione aspects, the α-dione can be bicyclo[2.2.1]hepta-1,2-dione, a substituted bicyclo[2.2.1]hepta-1,2-dione, bicyclo[2.2.2]octa-1,2-dione, a substituted bicyclo[2.2.2]octa-1,2-dione, or camphorquinone. In some saturated ring system aspects, the α-dione can be bicyclo[2.2.1]hepta-1,2-dione, bicyclo[2.2.2]octa-1,2-dione, or camphorquinone. In yet other saturated ring system α-dione aspects, the α-dione can be camphorquinone.

In unsaturated cyclic α-dione aspects, the α-dione can be 1,2-benzoquinone, a substituted 1,2-benzoquinone, cyclohex-3-ene-1,2-dione, a substituted cyclohex-3-ene-1,2-dione, cyclopent-3-ene-1,2-dione, a substituted cyclopent-3-ene-1,2-dione, cyclohex-4-ene-1,2-dione, a substituted cyclohex-4-ene-1,2-dione, 3,4-dihydro-1,2-naphthoquinone, a substituted 3,4-dihydro-1,2-naphtha-quinone, 1,4-dihydronaphthoquinone, or a substituted 1,4-dihydronaphthoquinone. In some unsaturated cyclic α-dione aspects, the α-dione can be 1,2-benzoquinone, cyclohex-3-ene-1,2-dione, cyclopent-3-ene-1,2-dione, cyclohex-4-ene-1,2-dione, 3,4-dihydronaphthoquinone, or 1,4-dihydronaphthoquinone. In other unsaturated ring α-dione aspects, the α-dione can be 1,2-benzoquinone; alternatively, 3,4-dihydronaphthoquinone; or alternatively, 1,4-dihydronaphthanoquinone.

In aromatic ring system α-dione aspects, the α-dione can be a 1,2-naphthoquinone, a substituted 1,2-naphthoquinone, 2,3-naphthoquinone, a substituted 2,3-naphthoquinone, acenaphthenequinone, a substituted acenaphthenequinone, phenanthrenequinone, a substituted phenanthrenequinone, pyrenequinone, or a substituted pyrenequinone. In some aromatic ring system α-dione aspects, the α-dione can be 1,2-naphthoquinone, 2,3-naphthoquinone, acenaphthenequinone, phenanthrenequinone, or pyrenequinone. In other aromatic ring system α-dione aspects, the α-dione can be acenaphthenequinone, phenanthrenequinone, or pyrenequinone. In yet other aromatic ring system α-dione aspects, the α-dione can be 1,2-naphthoquinone; alternatively, 2,3-naphthoquinone; alternatively, acenaphthenequinone; alternatively, phenanthrenequinone; or alternatively, pyrenequinone.

Within any substituted α-dione aspects, each substituent independently can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe the substituent of any substituted α-dione described herein.

In an aspect, the first imine group attached to the first imine nitrogen atom (first imine group for short) and/or second imine group attached to the second imine nitrogen atom (second imine group for short) of the α-diimine independently can be an organyl group; alternatively, an organyl group consisting essentially of inert functional groups; or alternatively, a hydrocarbyl group.

Generally, a bidentate α-diimine will have a first imine group and a second imine group which can be independently selected from an organyl group consisting essentially of inert functional groups and a hydrocarbyl group. Thus, when the α-diimine is a bidentate α-diimine, the bidentate α-diimine can comprise i) an α-diimine group, ii) a first imine nitrogen group consisting of an organyl group consisting essentially of inert functional groups (or a hydrocarbyl group) attached to a first imine nitrogen atom of the α-diimine group and ii) a second imine nitrogen group consisting of an organyl group consisting essentially of inert functional groups (or a hydrocarbyl group) attached to a second imine nitrogen atom of the α-diimine group.

Generally, a tridentate α-diimine will have a first imine group selected from an organyl group consisting essentially of inert functional groups or a hydrocarbyl group while the second imine group is an organyl group. When the α-diimine is a tridentate α-diimine, the organyl group which is the second imine group can be described as a second imine group comprising (1) an iron complexing group and (2) a linking group linking the iron complexing group to a second imine nitrogen atom of the α-diimine group. Thus, in some aspects, the tridentate α-diimine can comprise i) an α-diimine group, ii) a first imine nitrogen group consisting of an organyl group consisting essentially of inert functional groups (or a hydrocarbyl group) attached to a first imine nitrogen atom of the α-diimine group, and iii) a second imine nitrogen group comprising (1) an iron complexing group and (2) a linking group linking the iron complexing group to a second imine nitrogen atom of the α-diimine group. The iron complexing group and the linking group of the second imine group comprising (1) an iron complexing group and (2) a linking group linking the iron complexing group to a second imine nitrogen atom of the α-diimine group are independent elements of the second imine group and are independently described herein. The independent description of the iron complexing group and the linking group can be used without limitation and in any combination to further describe the second imine group comprising (1) an iron complexing group and (2) a linking group linking the iron complexing group to a second imine nitrogen atom of the α-diimine group of an α-diimine.

In any aspect and/or embodiment disclosed herein, the first and/or second imine organyl groups independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the first and/or second imine organyl groups consisting essentially of inert functional groups independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the first and/or second imine hydrocarbyl groups independently can be a $C_1$ to $C_{20}$, a $C_1$ to $C_{15}$, a $C_1$ to $C_{10}$, or a $C_1$ to $C_5$ hydrocarbyl group. Generally, the first imine group and the second imine group independently can be saturated or unsaturated, linear or branched, acyclic or cyclic, and/or aromatic or heteroaromatic. In other aspects the first imine group and/or second imine group, can be a primary, a secondary, a tertiary, or a quaternary group; alternatively, a primary group; alternatively, a secondary group; alternatively, a tertiary group; or alternatively, a quaternary group. One skilled in the art will readily recognize which imine nitrogen groups belong to the primary, secondary, tertiary, or quaternary imine nitrogen group classes.

In an aspect, the first imine group and/or second imine group independently can be an alkyl group, a substituted alkyl group, a cycloalkyl group, a substituted cycloalkyl group, an aryl group, or a substituted aryl group. In some aspects, the first imine group and/or second imine group independently can be an alkyl group or a substituted alkyl group; alternatively, a cycloalkyl group or a substituted cycloalkyl group; alternatively, an aryl group or a substituted aryl group; or alternatively, an alkyl group, a cycloalkyl group, or an aryl group. In other aspects, the first imine group and/or second imine group independently can be an alkyl group; alternatively, a substituted alkyl group, alternatively, a cycloalkyl group; alternatively, a substituted cycloalkyl group; alternatively, an aryl group; or alternatively, a substituted aryl group.

In any aspect and/or embodiment disclosed herein, the alkyl group which can be utilized as the first imine group and/or second imine group can be a $C_1$ to $C_{20}$, a $C_1$ to $C_{10}$, or a $C_1$ to $C_5$ alkyl group. In any aspect and/or embodiment disclosed herein, the substituted alkyl group which can be utilized as the first imine group and/or second imine group can be a $C_1$ to $C_{20}$, a $C_1$ to $C_{10}$, or a $C_1$ to $C_5$ substituted alkyl group. In any aspect and/or embodiment disclosed herein, the cycloalkyl group which can be utilized as the first imine group and/or second imine group can be a $C_4$ to $C_{20}$, a $C_4$ to $C_{15}$, or a $C_4$ to $C_{10}$ cycloalkyl group. In any aspect and/or embodiment disclosed herein, the substituted cycloalkyl group which can be utilized as the first imine group and/or second imine group can be a $C_4$ to $C_{20}$, a $C_4$ to $C_{15}$, or a $C_4$ to $C_{10}$ substituted cycloalkyl group. In any aspect and/or embodiment disclosed herein, the aryl group which can be utilized as the first imine group and/or second imine group can be a $C_6$ to $C_{20}$, a $C_6$ to $C_{15}$, or a $C_6$ to $C_{10}$ aryl group. In any aspect and/or embodiment disclosed herein, the substituted aryl group which can be utilized as the first imine group and/or second imine group can be a $C_6$ to $C_{20}$, a $C_6$ to $C_{15}$, or a $C_6$ to $C_{10}$ substituted aryl group. Each substituent of a substituted alkyl group (general or specific), a substituted cycloalkyl group (general or specific), a substituted aryl group (general or specific), and/or substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe the first imine group and/or second imine group.

In an aspect, the first imine nitrogen group and/or the second imine nitrogen group independently can be a methyl group, an ethyl group, a propyl group, a butyl group, or a pentyl group. In some aspects, the first imine nitrogen group and/or the second imine nitrogen group independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. In some aspects, the alkyl groups which can be utilized as the first imine nitrogen group and/or the second imine nitrogen group can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as the first imine nitrogen group and/or the second imine nitrogen group.

In an aspect, the first imine nitrogen group and/or the second imine nitrogen group can be a cyclopentyl group, a substituted cyclopentyl group, a cyclohexyl group, a substituted cyclohexyl group, an adamantyl group, or a substituted adamantyl group; alternatively, a cyclopentyl group or a substituted cyclopentyl group; alternatively, a cyclohexyl group or a substituted cyclohexyl group; alternatively, an adamantyl group or a substituted adamantyl group; alternatively, a cyclopentyl group; alternatively, a substituted cyclopentyl group; alternatively, a cyclohexyl group; alternatively, a substituted cyclohexyl group; alternatively, an adamantyl group; or alternatively, a substituted adamantyl group. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as the first imine nitrogen group and/or the second imine nitrogen group.

In an aspect, the first imine nitrogen group and/or the second imine nitrogen group can be a phenyl group, a substituted phenyl group, a naphthyl group, or a substituted naphthyl group; alternatively, a phenyl group or a substituted phenyl group; alternatively, a naphthyl group, or a substituted naphthyl group; alternatively, a phenyl group; alternatively, a substituted phenyl group; alternatively, a naphthyl group; or alternatively, a substituted naphthyl group. In an aspect, each substituted phenyl group which can be the first imine nitrogen group and/or the second imine nitrogen group can comprise a substituent at the 2 position, a substituent at the 3 position, a substituent at the 4 position, substituents at the 2 and 3 positions, substituents at the 2 and 4 positions, substituents at the 2 and 5 positions, substituents at the 3 and 5 positions, substituents at the 2 and 6 positions, or substituents at the 2, 4, and 6 positions; alternatively, a substituent at the 2 position, a substituent at the 4 position, substituents at the 2 and 4 positions, substituents at the 2 and 6 positions, or substituents at the 2, 4, and 6 position; alternatively, substituents at the 2 and 6 positions or substituents at the 2, 4, and 6 positions; alternatively, a substituent at the 2 position; alternatively, a substituent at the 3 position; alternatively, a substituent at the 4 position; alternatively, substituents at the 2 and 3 positions; alternatively, substituents at the 2 and 4 positions; alternatively, substituents at the 2 and 5 positions; alternatively, substituents at the 3 and 5 positions; alternatively, substituents at the 2 and 6 positions; or alternatively, substituents at the 2, 4, and 6 positions. In some aspects, the substituted phenyl group, which can be utilized as the first imine nitrogen group and/or the second imine nitrogen group, can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In an aspect, one or more substituents of a multi-substituted phenyl group utilized as the first imine nitrogen group and/or the second imine nitrogen group can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as the first imine nitrogen group and/or the second imine nitrogen group.

In a non-limiting aspect, the substituted phenyl group, which can be utilized as the first imine nitrogen group and/or the second imine nitrogen group can be a 2-alkylphenyl group, a 3-alkylphenyl group, a 4-alkylphenyl group, a 2,3-dialkylphenyl group, a 2,4-dialkylphenyl group, a 2,5-dialkylphenyl group, a 3,5-dialkylphenyl group, a 2,6-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-alkylphenyl group; alternatively, a 2,6-dialkylphenyl group, or a 2,4,6-trialkylphenyl group; alternatively, a 2-alkylphenyl group; alternatively, a 4-alkylphenyl group; alternatively, a 2,3-dialkylphenyl group; alternatively, a 2,4-dialkylphenyl group; alternatively, a 2,5-dialkylphenyl group; alternatively, a 3,5-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as the first imine nitrogen group and/or the second imine nitrogen group. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, the substituted phenyl groups which can be the first imine nitrogen group and/or the second imine nitrogen group can be a 2,6-dimethylphenyl group, a 2,6-diethylphenyl group, a 2,6-diisopropylphenyl group, or a 2,5-di-tert-butylphenyl group, a 2-isopropyl-6-methylphenyl group, or a 2,4,6-trimethylphenyl group; alternatively, a 2,6-dimethylphenyl group, a 2,6-diethylphenyl group, or a 2,6-diisopropylphenyl group; alternatively, a 2,6-dimethylphenyl group or a 2,4,6-trimethylphenyl group; alternatively, a 2,6-dimethylphenyl group; alternatively, a 2,6-diethylphenyl group; alternatively, a 2,6-diisopropylphenyl group; alternatively, a 2,5-di-tert-butylphenyl group; alternatively, a 2-isopropyl-6-methylphenyl group; or alternatively, a 2,4,6-trimethylphenyl group.

In tridentate α-diimine aspects, the second imine nitrogen group can comprise (1) an iron complexing group and (2) a linking group linking the iron complexing group to a second imine nitrogen atom of the α-diimine group. Generally, the iron complexing group and the linking group linking the iron complexing group to the second imine nitrogen atom of the α-diimine group are independent elements of the second imine group and are independently described herein. The independent descriptions of the iron complexing group and the linking group can be used without limitation, and in any combination, to further describe the second imine group comprising (1) an iron complexing group and (2) a linking group linking the iron complexing group to a second imine nitrogen atom of the α-diimine group of an α-diimine.

Generally, the iron salt complexing group can be any group comprising a heteroatom capable of complexing with the iron salt and the linking group can be any group capable of linking the iron salt complexing group to the second imine nitrogen atom of the α-diimine group. The linking group includes all atoms between the second imine nitrogen atom and the iron salt complexing group. If the iron salt complexing group is acyclic, the linking group includes all atoms between the second imine nitrogen atom and the heteroatom of the iron salt complexing functional group. For example, in an N,N-dimethylethylene group, the linking group is —CH$_2$CH$_2$— and the iron salt complexing group is the N,N-dimethylaminyl group, while in a 2-phenoxyethyl group the linking group is —CH$_2$CH$_2$— and the iron salt complexing group is the phenoxy group. However, if the heteroatom of the iron salt complexing group is contained within a ring, the linking group includes all the atoms between the second imine nitrogen atom and the first atom within the ring containing the iron salt complexing heteroatom of the iron salt complexing group. For example, in a 2-ethylpyridinyl group the linking group is —CH$_2$CH$_2$— and the iron salt complexing group is the 2-pyridinyl group, while in 1-ethylpiperidinyl group the linking group is —CH$_2$CH$_2$— and the iron salt complexing group is the 1-piperidinyl group.

The iron salt complexing group can be any group comprising a heteroatom capable of complexing with the iron salt. In an aspect, the iron salt complexing group can be a $C_2$ to $C_{30}$, a $C_2$ to $C_{20}$, a $C_2$ to $C_{10}$, or a $C_2$ to $C_5$ group comprising a heteroatom capable of complexing with the iron salt. In some aspects embodiments, the iron salt complexing heteroatom of the iron salt complexing group can be an oxygen, sulfur, nitrogen, or phosphorus; alternatively, oxygen or sulfur; or alternatively, nitrogen or phosphorus. In other aspects, the iron salt complexing heteroatom of the iron salt complexing group can be oxygen; alternatively, sulfur; alternatively, nitrogen; or alternatively, phosphorus. Optionally, the iron salt complexing group can contain additional heteroatoms which do not complex the iron salt in the α-diimine iron complex such as inert heteroatoms (e.g. halides, and silicon) and/or additional iron salt complexing heteroatom(s) which do not complex with the iron salt.

In an aspect, the iron salt complexing group can be a dihydrocarbyl aminyl group, a di(substituted hydrocarbyl) aminyl group, a dihydrocarbyl phosphinyl group, a di(substituted hydrocarbyl) phosphinyl group, a hydrocarbyl etheryl group, a substituted hydrocarbyl etheryl group, a hydrocarbyl sulfidyl group, a substituted hydrocarbyl sulfidyl group, a furanyl group, a substituted furanyl group, a tetrahydrofuranyl group, a substituted tetrahydrofuranyl group, a pyridinyl group, a substituted pyridinyl group, a morphilinyl group, a substituted morphilinyl group, a pyrrolyl group, a substituted pyrrolyl group, a pyrrolidinyl group, a substituted pyrrolidinyl group, a piperidinyl group, or a substituted piperidinyl group. In some aspects, the iron salt complexing group can be a dihydrocarbyl aminyl group or a di(substituted hydrocarbyl) aminyl group; alternatively, a dihydrocarbyl phosphinyl group or a di(substituted hydrocarbyl) phosphinyl group; alternatively, a hydrocarbyl etheryl group or a substituted hydrocarbyl etheryl group; or alternatively, a hydrocarbyl sulfidyl group or a hydrocarbyl sulfidyl group. In other aspects, the iron salt complexing group can be a dihydrocarbyl aminyl group; alternatively, a di(substituted hydrocarbyl) aminyl group; alternatively, a dihydrocarbyl phosphinyl group; or alternatively, a di(substituted hydrocarbyl) phosphinyl group. Each substituent of a substituted iron complexing group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted iron complexing group.

Each hydrocarbyl group of any iron complexing group having a hydrocarbyl group disclosed herein independently can be a $C_1$ to $C_{20}$, a $C_1$ to $C_{15}$, a $C_1$ to $C_{10}$, or a $C_1$ to $C_5$ hydrocarbyl group while each substituted hydrocarbyl group of an iron complexing group having a substituted hydrocarbyl group disclosed herein independently can be a $C_1$ to $C_{20}$, a $C_1$ to $C_{15}$, a $C_1$ to $C_{10}$, or a $C_1$ to $C_5$ substituted hydrocarbyl group. In an aspect, each hydrocarbyl/substituted hydrocarbyl group of an iron complexing group having a hydrocarbyl/substituted hydrocarbyl group described herein independently can be an alkyl group, a substituted alkyl group, a cycloalkyl group, a substituted cycloalkyl group, an aryl group, or a substituted aryl group; alternatively, an alkyl group or a substituted alkyl group; alternatively, a cycloalkyl group or a substituted cycloalkyl group; alternatively, an aryl group or a substituted aryl group; alternatively, an alkyl group, a cycloalkyl group, or an aryl group; alternatively, an alkyl group; alternatively, a substituted alkyl group, alternatively, a cycloalkyl group; alternatively, a substituted cycloalkyl group; alternatively, an aryl group; or alternatively, a substituted aryl group. Each substituent of a substituted alkyl group (general or specific), a substituted cycloalkyl group (general or specific), a substituted aryl group (general or specific), and/or a substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted iron complexing group.

In any aspect and/or embodiment disclosed herein, the alkyl group of any iron complexing group having an alkyl group disclosed herein independently can be a $C_1$ to $C_{20}$, a $C_1$ to $C_{10}$, or a $C_1$ to $C_5$ alkyl group while the substituted alkyl group of any iron complexing group having an alkyl group disclosed herein independently can be a $C_1$ to $C_{20}$, a $C_1$ to $C_{10}$, or a $C_1$ to $C_5$ substituted alkyl group. In an aspect, the alkyl group of any iron complexing group having an alkyl group disclosed herein independently can be a methyl group, an ethyl group, a propyl group, a butyl group, or a pentyl group. In some aspects, the alkyl group of any iron complexing group having an alkyl group disclosed herein independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group. In some aspects, the alkyl groups which can be utilized as the alkyl group of any iron complexing group having an alkyl group disclosed herein can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as the substituted alkyl group of an iron complexing group.

In any aspect or embodiment disclosed herein, the cycloalkyl group of any iron complexing group having a cycloalkyl group disclosed herein independently can be a $C_4$ to $C_{20}$, a $C_4$ to $C_{15}$, or a $C_4$ to $C_{10}$ cycloalkyl group while the substituted cycloalkyl group of any iron complexing group having a cycloalkyl group disclosed herein independently can be a $C_4$ to $C_{20}$, a $C_4$ to $C_{15}$, or a $C_4$ to $C_{10}$ substituted cycloalkyl group. In an aspect, each cycloalkyl/substituted cycloalkyl group of an iron complexing group having a cycloalkyl/substituted cycloalkyl group described herein independently can be cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group which can be utilized as the substituted cycloalkyl group of an iron complexing group.

In any aspect and/or embodiment disclosed herein, the aryl group of any iron complexing group having an aryl group disclosed herein independently can be a $C_6$ to $C_{20}$, a $C_6$ to $C_{15}$, or a $C_6$ to $C_{10}$ aryl group while the substituted aryl group of any iron complexing group having a substituted aryl group disclosed herein independently a $C_6$ to $C_{20}$, a $C_6$ to $C_{15}$, or a $C_6$ to $C_{10}$ substituted aryl group. In an aspect, the aryl/substituted aryl group of any iron complexing group having an aryl/substituted aryl group disclosed herein independently can be a phenyl group or a substituted phenyl group; alternatively, a phenyl group; or alternatively, a substituted phenyl group. In some aspects, the substituted phenyl group of any iron complexing group having a substituted phenyl group independently can be a $C_6$ to $C_{20}$, a $C_6$ to $C_{15}$, or a $C_6$ to $C_{10}$ substituted phenyl group. In some aspects, the substituted phenyl group of any iron complexing group having a substituted phenyl group independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as a substituted phenyl group for any iron complexing group having a substituted aryl group or substituted phenyl group described herein can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) which can be utilized as a substituted phenyl group for any iron complexing group having a substituted aryl group or substituted phenyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as utilized as a substituted phenyl group for any iron complexing group having a substituted aryl group or substituted phenyl group.

In an aspect, the substituted phenyl group of any iron complexing group having a substituted phenyl group disclosed herein independently can be a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as a substituted phenyl group for any iron complexing group having a substituted aryl group or substituted phenyl group described herein. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, the substituted phenyl group of any iron complexing group having a substituted phenyl group disclosed herein independently can be a 3,5-dimethylphenyl group.

The linking group linking the iron salt complexing group to the second imine nitrogen atom of the α-diimine group can be a bond or an organyl group; alternatively, a bond or an organyl group consisting essentially of inert functional groups; alternatively, a bond or a hydrocarbyl group; alternatively, an organyl group; alternatively, an organyl group consisting essentially of inert functional groups; alternatively, a hydrocarbyl group; or alternatively, a bond. In any aspect and/or embodiment disclosed herein, the organyl linking group linking the iron salt complexing group to the second imine nitrogen atom of the α-diimine group can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the organyl group consisting essentially of inert functional groups linking group linking the iron salt complexing group to the second imine nitrogen atom of the α-diimine group can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the hydrocarbyl group linking group linking the iron salt complexing group to the second imine nitrogen atom of the α-diimine group can be a $C_1$ to $C_{20}$, a $C_1$ to $C_{15}$, a $C_1$ to $C_{10}$, or a $C_1$ to $C_5$ hydrocarbyl group. In any aspect and/or embodiment disclosed herein, the hydrocarbyl group linking group linking the iron salt complexing group to the second imine nitrogen atom of the α-diimine group can be a $C_1$ to $C_{20}$, a $C_1$ to $C_{15}$, a $C_1$ to $C_{10}$, or a $C_1$ to $C_5$ alkyl group. Generally, the linking group linking the iron salt complexing group to the second imine nitrogen atom of the α-diimine group can be saturated or unsaturated, linear or branched, acyclic or cyclic, and/or aromatic.

In an aspect, the linking group linking the iron salt complexing group to the second imine nitrogen atom of the α-diimine group can be —$(CR^{L1})_m$—, a phenyl-1,2-ene group, or a substituted phenyl-1,2-ene group; alternatively, a phenyl-1,2-ene group or a substituted phenyl-1,2-ene group; alternatively, —$(CR^{L1})_m$—; alternatively, a phenyl-1,2-ene group; alternatively, a substituted phenyl-1,2-ene group. R" and m are independent elements of the linking group having the structure —$(CR^{L1})_m$— and are independently described herein. The independent description of $R^{L1}$ and m can be utilized without limitation, and in any combination, to further describe the linking group linking the iron salt complexing group to the second imine nitrogen atom of the α-diimine group having the structure —$(CR^{L1})_m$—. Within the structure —$(CR^{L1})_m$—, each $R^{L1}$ independently can be hydrogen, a methyl group, an ethyl group, a propyl group, an isopropyl group, or a butyl group; alternatively, hydrogen, a methyl group, or a propyl group. Within the structure —$(CR^{L1})_m$—, m can be an integer from 1 to 5; alternatively 2 or 3; alternatively 2; or alternatively, 3. Each substituent of a substituted phenyl-1,2-ene group which can be utilized as the linking group linking the iron salt complexing group to the second imine nitrogen atom of the α-diimine group can be a halide, an alkyl group, or a hydrocarboxy group; alternatively, a halide or an alkyl group; alternatively, a halide and a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe the substituted phenyl-1,2-ene group which can be utilized as the linking group linking the iron salt complexing group to the second imine nitrogen atom of the α-diimine group. In some aspects, the linking group linking the iron salt complexing group to the second imine nitrogen atom of the α-diimine group can be a methylene group, an eth-1,2-ylene group, a prop-1,3-ylene group, a butyl-1,3-ene group, a dimethylmethylene group, a butyl-1,4-ene group or a phen-1,2-ylene group. In some non-limiting aspects, the linking group linking the iron salt complexing group to the second imine nitrogen atom of the α-diimine group can be an eth-1,2-ylene group, a prop-1,3-ylene group, or a phen-1,2-ylene group; alternatively, an eth-1,2-ylene group, or a prop-1,3-ylene group; alternatively, an eth-1,2-ylene group; alternatively, a prop-1,3-ylene group; or alternatively, a phen-1,2-ylene group.

In a non-limiting aspect, the second imine group comprising (1) an iron complexing group and (2) a linking group linking the iron complexing group to a second imine nitrogen atom of the α-diimine group can be a 2-(N,N-diisopropylaminyl)ethyl group, a 2-(N,N-diphenylaminyl)ethyl group, a 2-(N,N-di-(3,5-dimethylphenyl)aminyl)ethyl group, a 2-(di(isopropylphenyl)phosphinyl)ethyl group, a 2-(diphenylphosphinyl)ethyl group, a 2-(di-(3,5-dimethylphenyl)phosphinyl)ethyl group, a 3-(diisopropylphosphinyl)propyl group, a 3-(diphenylphosphinyl)propyl group, a 3-(di-(3,5-dimethylphenyl)phosphinyl)propyl group, a 2-isopropoxyethyl group, a 2-phenoxyethyl group, or a 2-(3,5-dimethylphenoxy)ethyl group. In some non-limiting aspects, the second imine group comprising (1) an iron complexing group and (2) a linking group linking the iron complexing group to a second imine nitrogen atom of the α-diimine group can be a 2-(N,N-diisopropylaminyl)ethyl group, a 2-(N,N-diphenylaminyl)ethyl group, a 2-(N,N-di-(3,5-dimethylphenyl)aminyl)ethyl group; alternatively, a 2-(di(isopropylphenyl)phosphinyl)ethyl group, a 2-(diphenylphosphinyl)ethyl group, a 2-(di-(3,5-dimethylphenyl)phosphinyl)ethyl group, a 3-(diisopropylphosphinyl)propyl group, a 3-(diphenylphosphinyl)propyl group, a 3-(di-(3,5-dimethylphenyl)phosphinyl)propyl group; or alternatively, a 2-isopropoxyethyl group, a 2-phenoxyethyl group, or a 2-(3,5-dimethylphenoxy)ethyl group. In other non-limiting aspects, the second imine group comprising (1) an iron complexing group and (2) a linking group linking the iron complexing group to a second imine nitrogen atom of the α-diimine group can be a 2-(di(isopropylphenyl)phosphinyl)ethyl group, a 2-(diphenylphosphinyl)ethyl group, a 2-(di-(3,5-dimethylphenyl)phosphinyl)ethyl group; alternatively, a 3-(diisopropylphosphinyl)propyl group, a 3-(diphenylphosphinyl)propyl group, a 3-(di-(3,5-dimethylphenyl)phosphinyl)propyl group; alternatively, a 2-(di(isopropylphenyl)phosphinyl)ethyl group; alternatively, a 2-(diphenylphosphinyl)ethyl group; or alternatively, a 2-(di-(3,5-dimethylphenyl)phosphinyl)ethyl group.

In various aspects and/or embodiments, a pyridine bisimine or a pyridine bisimine iron salt complex can be utilized in the processes described herein. Generally, the pyridine bisimine or the pyridine bisimine iron salt complex can be any pyridine bisimine or any pyridine bisimine iron salt complex that when contacted with ethylene and any other appropriate reagent(s) under the appropriate conditions can form an oligomer product. Generally, the pyridine bisimine and the iron salt of the pyridine bisimine iron salt complex are independent elements of the pyridine bisimine iron salt complex and are independently disclosed herein. The independent descriptions of the pyridine bisimine and the iron salt of the pyridine bisimine iron salt complex can be used without limitation, and in any combination, to further describe the pyridine bisimine iron salt complex that can be utilized in aspects and/or embodiments of the processes described herein. In an aspect, the pyridine bisimine or the pyridine bisimine of the pyridine bisimine iron salt complex can comprise only one pyridine bisimine group; or alternatively, the pyridine bisimine can comprise only two pyridine bisimine groups.

In an aspect, the pyridine bisimine or the pyridine bisimine of the pyridine bisimine iron salt complex can have Structure PBI I or Structure PBI II; alternatively, Structure PBI I; or alternatively, Structure PBI II. In an aspect, the pyridine bisimine iron salt complex can have Structure PBIFe I or Structure PBIFe II; alternatively, Structure PBIFe I; or alternatively, Structure PBIFe II.

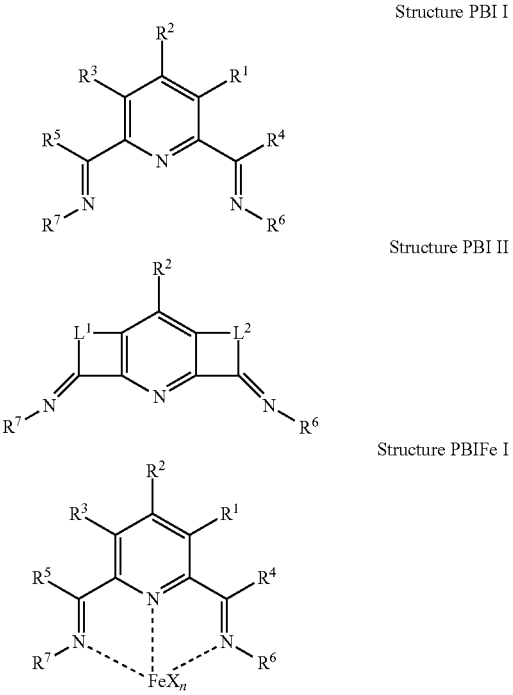

Structure PBI I

Structure PBI II

Structure PBIFe I

-continued

Structure PBIFe II

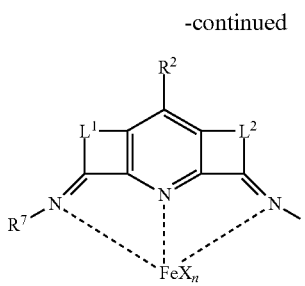

$R^1$, $R^2$, $R^3$, $R^4$, $R^5$, $R^6$, and $R^7$ of the pyridine bisimine having Structure PBI I or the pyridine bisimine iron salt complex having Structure PBIFe I are independent elements of the pyridine bisimine having Structure PBI I and the pyridine bisimine iron salt complex having Structure PBIFe I and are independently described herein. The independent descriptions of $R^1$, $R^2$, $R^3$, $R^4$, $R^5$, $R^6$, and $R^7$ can utilized without limitation, and in any combination, to further describe the pyridine bisimine having Structure PBI I and/or the pyridine bisimine iron salt complex having Structure PBIFe I. Similarly, $R^2$, $R^6$, $R^7$, $L^1$, and $L^2$ of the pyridine bisimine having Structure PBI II or the pyridine bisimine iron salt complex having Structure PBIFe II are independent elements of the pyridine bisimine having Structure PBI II and the pyridine bisimine iron salt complex having Structure PBIFe II and are independently described herein. The independent descriptions of $R^2$, $R^6$, $R^7$, $L^1$, and $L^2$ can utilized without limitation, and in any combination, to further describe the pyridine bisimine having Structure PBI II and/or the pyridine bisimine iron salt complex having Structure PBIFe II. Additionally, the iron salt, $FeX_n$, is independently described herein can be combined, without limitation, with the independently described $R^1$, $R^2$, $R^3$, $R^4$, $R^5$, $R^6$, $R^7$, $L^1$, and $L^2$ to further describe the appropriate pyridine bisimine iron salt complex structure described herein which have an $R^1$, $R^2$, $R^3$, $R^4$, $R^5$, $R^6$, $R^7$, $L^1$, and/or $L^2$.

Generally, $R^1$, $R^2$, and/or $R^3$ of the respective pyridine bisimines and pyridine bisimine iron salt complexes, which have an $R^1$, $R^2$, and/or $R^3$, independently can be hydrogen, an inert functional group, or an organyl group; alternatively, hydrogen or an organyl group; alternatively, an inert functional group or an organyl group; alternatively, hydrogen, an inert functional group, or an organyl group consisting essentially of inert functional groups; alternatively, hydrogen or an organyl group consisting essentially of inert functional groups; alternatively, an inert functional group or an organyl group consisting essentially of inert functional groups; alternatively, hydrogen, an inert functional group, or a hydrocarbyl group; alternatively, hydrogen or a hydrocarbyl group; alternatively, an inert functional group or a hydrocarbyl group; alternatively, alternatively, hydrogen or an inert functional group; alternatively, hydrogen; alternatively, an organyl group; alternatively, organyl group consisting essentially of inert functional groups; or alternatively, a hydrocarbyl group. In any aspect and/or embodiment disclosed herein, the $R^1$, $R^2$, and/or $R^3$ organyl groups of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^1$, $R^2$, and/or $R^3$ organyl groups consisting essentially of inert functional groups, of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^1$, $R^2$, and/or $R^3$ hydrocarbyl groups of the pyridine bisimines and/or pyridine bisimine iron salt complexes which have an $R^1$, $R^2$, and/or $R^3$ group, independently can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the $R^1$, $R^2$, and/or $R^3$ hydrocarbyl groups of the pyridine bisimines and pyridine bisimine iron salt complexes which have an $R^1$, $R^2$, and/or $R^3$ group, independently can be a $C_1$ to $C_{20}$, a $C_1$ to $C_{10}$, or a $C_1$ to $C_5$ alkyl group. In an aspect, the $R^1$, $R^2$, and/or $R^3$ alkyl groups of the pyridine bisimines and pyridine bisimine iron salt complexes which have an $R^1$, $R^2$, and/or $R^3$ group, independently can be a methyl group, an ethyl group, a propyl group, a butyl group, a pentyl group, a hexyl group, a heptyl group, or an octyl group. In some aspects, the $R^1$, $R^2$, and/or $R^3$ alkyl groups of the pyridine bisimines and pyridine bisimine iron salt complexes which have an $R^1$, $R^2$, and/or $R^3$ group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In a particular aspect, $R^1$, $R^2$, and/or $R^3$ of the pyridine bisimines which have an $R^1$, $R^2$, and/or $R^3$ group, each can be hydrogen. In these aspects, the pyridine bisimine can have Structure PBI III or Structure PBI IV; alternatively, Structure PBI III; or alternatively, Structure PBI IV. Similarly, in a particular aspect, $R^1$, $R^2$, and $R^3$ of the pyridine bisimine iron salt complexes which have an $R^1$, $R^2$, and/or $R^3$ group, each can be hydrogen. In these aspects, the pyridine bisimine iron salt complexes can have Structure PBIFe III or Structure PBIFe IV; alternatively, Structure PBIFe III; or alternatively, Structure PBIFe IV.

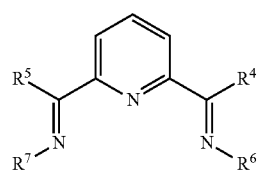

Structure PBI III

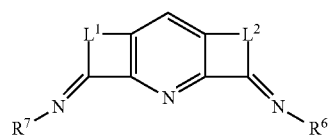

Structure PBI IV

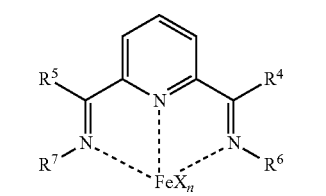

Structure PBIFe III

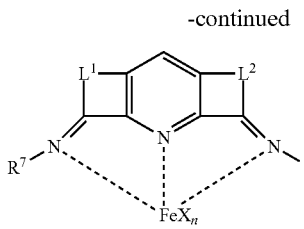

Structure PBIFe IV $R^4$, $R^5$, $R^6$, and $R^7$ of the pyridine bisimine having Structure PBI III or the pyridine bisimine iron salt complex having Structure PBIFe III are independent elements of the pyridine bisimine having Structure PBI III and the pyridine bisimine iron salt complex having Structure PBIFe III and are independently described herein. The independent descriptions of $R^4$, $R^5$, $R^6$, and $R^7$ can be utilized without limitation, and in any combination, to further describe the pyridine bisimine having Structure PBI III and/or the pyridine bisimine iron salt complex having Structure PBIFe III. Similarly, $R^6$, $R^7$, $L^1$, and $L^2$ of the pyridine bisimine having Structure PBI IV or the pyridine bisimine iron salt complex having Structure PBIFe IV are independent elements of the pyridine bisimine having Structure PBI IV and the pyridine bisimine iron salt complex having Structure PBIFe IV and are independently described herein. The independent descriptions of $R^6$, $R^7$, $L^1$, and $L^2$ can be utilized without limitation, and in any combination, to further describe the pyridine bisimine having Structure PBI III and/or the pyridine bisimine iron salt complex having Structure PBIFe III. Additionally, the iron salt, $FeX_n$, is independently described herein can be combined, without limitation, with the independently described $R^4$, $R^5$, $R^6$, $L^1$, and $L^2$ to further describe the appropriate pyridine bisimine iron salt complex structure described herein which have an $R^4$, $R^5$, $R^6$, $R^7$, $L^1$, and/or $L^2$.

Generally, $R^4$ and/or $R^5$ of the pyridine bisimines and pyridine bisimine iron salt complexes, which have an $R^4$ and/or $R^5$, independently can be hydrogen or an organyl group; alternatively, hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In any aspect and/or embodiment disclosed herein, the $R^4$ and/or $R^5$ organyl groups of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group. In any aspect and/or embodiment disclosed herein, the $R^4$ and/or $R^5$ organyl groups consisting essentially of inert functional groups, of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ organyl group consisting essentially of inert functional groups. In any aspect and/or embodiment disclosed herein, the $R^4$ and/or $R^5$ hydrocarbyl groups of the pyridine bisimines and pyridine bisimine iron salt complexes which have an $R^4$ and/or $R^5$ group, independently can be a $C_1$ to $C_{20}$, a $C_1$ to $C_{15}$, a $C_1$ to $C_{10}$, or a $C_1$ to $C_5$ hydrocarbyl group.

In any aspect and/or embodiment disclosed herein, the $R^4$ and/or $R^5$ hydrocarbyl groups of the pyridine bisimines and pyridine bisimine iron salt complexes which have an $R^4$ and/or $R^5$ group, independently can be a $C_1$ to $C_{20}$, a $C_1$ to $C_{10}$, or a $C_1$ to $C_5$ alkyl group. In an aspect, the $R^4$ and/or $R^5$ alkyl groups of the pyridine bisimines and pyridine bisimine iron salt complexes which have an $R^4$ and/or $R^5$ group, independently can be a methyl group, an ethyl group, a propyl group, a butyl group, a pentyl group, a hexyl group, a heptyl group, or an octyl group. In some aspects, the $R^4$ and/or $R^5$ alkyl groups of the pyridine bisimines and pyridine bisimine iron salt complexes which have an $R^4$ and/or $R^5$ group, independently can be a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group.

In an aspect, $R^1$ and $R^4$ and/or $R^3$ and $R^5$ can be joined to form a ring or a ring system containing two carbon atoms of the pyridine group and the carbon atom of the imine group. In such aspects, $L^1$ represents the joined $R^3$ and $R^5$ while $L^2$ represents the joined $R^1$ and $R^4$. Generally, $L^1$ and/or $L^2$ of a pyridine bisimine or pyridine bisimine iron salt complex having an $L^1$ and/or $L^2$ independently can be an organylene group; alternatively, an organylene group consisting essentially of inert functional groups; or alternatively, a hydrocarbylene group. In any aspect or embodiment disclosed herein, the $L^1$ and/or $L^2$ organylene groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ organylene group. In any aspect or embodiment disclosed herein, the $L^1$ and/or $L^2$ organylene groups consisting essentially of inert functional groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or alternatively, a $C_2$ to $C_5$ organylene group consisting essentially of inert functional groups. In any aspect or embodiment disclosed herein, the $L^1$ and/or $L^2$ hydrocarbylene groups of a pyridine bisimine or pyridine bisimine iron salt complex which have an $L^1$ and/or $L^2$ group, independently can be a $C_2$ to $C_{20}$, a $C_2$ to $C_{15}$, a $C_2$ to $C_{10}$, or a $C_2$ to $C_5$ hydrocarbylene group. In any aspect or embodiments disclosed herein, the $L^1$ and/or $L^2$ hydrocarbylene groups of the pyridine bisimines and pyridine bisimine iron salt complexes which have an $L^1$ and/or $L^2$, independently can be a $C_2$ to $C_{20}$, a $C_2$ to $C_{10}$, or a $C_2$ to $C_5$ alkylene group. In any aspect or embodiment where the pyridine bisimine or the pyridine bisimine iron salt complex has an $L^1$ and an $L^2$ group, $L^1$ and $L^2$ can be different; or alternatively, $L^1$ and $L^2$ can be the same.

In an aspect, $L^1$ and/or $L^2$ independently can have the structure $-(C(R^{11})_2)_p-$. Generally, $R^{11}$ and p are independent features of $L^1$ and/or $L^2$ having the structure $-(C(R^{11})_2)_p-$ and are independently described herein. The independent description of $R^{11}$ and p can be utilized without limitation, and in any combination, to describe $L^1$ and/or $L^2$ having the structure $-(CR^{11})_p-$ and can be further utilized to describe the pyridine bisimines and/or the pyridine bisimine iron salt complexes which have an $L^1$ and/or $L^2$. In an aspect, each $R^{11}$ independently can be hydrogen, an inert functional group, or a hydrocarbyl group; alternatively, hydrogen or a hydrocarbyl group; alternatively, hydrogen; or alternatively, a hydrocarbyl group. General and specific inert functional groups and hydrocarbyl group are independently described herein (e.g., as potential substituent groups) and these descriptions can be utilized without limitation to further describe $L^1$ and $L^2$. In an aspect, each p independently can be an integer from 2 to 5; alternatively, an integer from 2 to 3; alternatively, 2; or alternatively, 3. In a non-limiting aspect, $L^1$ and $L^2$ independently can be —CH$_2$CH$_2$—, —CH$_2$CH$_2$CH$_2$—, —CH(CH$_3$)CH$_2$—, —C(CH$_3$)$_2$—, or —CH$_2$CH$_2$CH$_2$CH$_2$—; alternatively, —CH$_2$CH$_2$— or —CH$_2$CH$_2$CH$_2$—; alternatively, —CH$_2$CH$_2$—; or alternatively, —CHCH$_2$CH$_2$—. In an aspect, L$^1$ and L$^2$ can be different. In other aspects, L$^1$ and L$^2$ can be the same.

Generally, R$^6$ and/or R$^7$ of the pyridine bisimines and the pyridine bisimine iron salt complexes independently can be an aryl group, a substituted aryl group, a phenyl group, or a substituted phenyl group; alternatively, aryl group or a substituted aryl group; alternatively, a phenyl group or a substituted phenyl group; alternatively, aryl group; alternatively, a substituted aryl group; alternatively, a phenyl group; or alternatively, a substituted phenyl group. In any aspect and/or embodiment disclosed herein, the R$^6$ and/or R$^7$ aryl groups of the pyridine bisimines and/or pyridine bisimine iron salt complexes independently can be a C$_6$ to C$_{20}$, a C$_6$ to C$_{15}$, or a C$_6$ to C$_{10}$ aryl group. In any aspect and/or embodiment disclosed herein, the R$^6$ and/or R$^7$ substituted aryl groups of the pyridine bisimines and/or pyridine bisimine iron salt complexes independently can be a C$_6$ to C$_{20}$, a C$_6$ to C$_{15}$, or a C$_6$ to C$_{10}$ substituted aryl group. In any aspect and/or embodiment disclosed herein, the R$^6$ and/or R$^7$ substituted phenyl groups of the pyridine bisimines and/or pyridine bisimine iron salt complexes independently can be a C$_6$ to C$_{20}$, a C$_6$ to C$_{15}$, or a C$_6$ to C$_{15}$ substituted phenyl group. Each substituent of a substituted aryl group (general or specific) or a substituted phenyl group (general or specific) which can be utilized as R$^6$ and/or R$^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe R$^6$ and/or R$^7$ of the pyridine bisimines and the pyridine bisimine iron salt complexes.

In an aspect, each substituted phenyl group which can be utilized as R$^6$ and/or R$^7$ of the pyridine bisimines and the pyridine bisimine iron salt complexes independently can be a substituted phenyl group comprising a substituent at the 2-position, a substituted phenyl group comprising a substituent at the 3-position, a substituted phenyl group comprising a substituent at the 4-position, a substituted phenyl group comprising substituents at the 2- and 3-positions, a substituted phenyl group comprising substituents at the 2- and 4-positions, a substituted phenyl group comprising substituents at the 2- and 5-positions, a substituted phenyl group comprising substituents at the 3- and 5-positions, a substituted phenyl group comprising substituents at the 2- and 6-positions, or a substituted phenyl group comprising substituents at the 2-, 4-, and 6-positions; alternatively, a substituted phenyl group comprising a substituent at the 2-position, a substituted phenyl group comprising a substituent at the 4-position, a substituted phenyl group comprising substituents at the 2- and 4-positions, a substituted phenyl group comprising substituents at the 2- and 6-positions, or a substituted phenyl group comprising substituents at the 2-, 4-, and 6-positions; alternatively, a substituted phenyl group comprising substituents at the 2- and 6-positions or a substituted phenyl group comprising substituents at the 2-, 4-, and 6-positions; alternatively, a substituted phenyl group comprising a substituent at the 2-position; alternatively, a substituted phenyl group comprising a substituent at the 3-position; alternatively, a substituted phenyl group comprising a substituent at the 4-position; alternatively, a substituted phenyl group comprising substituents at the 2- and 3-positions; alternatively, a substituted phenyl group comprising substituents at the 2- and 4-positions; alternatively, a substituted phenyl group comprising substituents at the 2- and 5-positions; alternatively, a substituted phenyl group comprising substituents at the 3- and 5-positions; alternatively, a substituted phenyl group comprising substituents at the 2- and 6-position; or alternatively, a substituted phenyl group comprising substituents at the 2-, 4-, and 6-positions. In some aspects, each substituted phenyl group which can be utilized as R$^6$ and/or R$^7$ of the pyridine bisimines and the pyridine bisimine iron salt complexes independently can be selected such that (1) one, two, or three of the 2- and 6-positions of the R$^6$ and R$^7$ phenyl groups and/or substituted phenyl groups independently can be a halogen, a primary carbon atom group, or a secondary carbon atom group and the remainder of the 2- and 6-positions of the R$^6$ and R$^7$ phenyl groups and/or substituted phenyl groups can be hydrogen, (2) one of the 2- and 6-positions of the R$^6$ and R$^7$ phenyl groups and/or substituted phenyl groups can be a tertiary carbon atom group, none, one, or two of the 2- and 6-positions of the R$^6$ and R$^7$ phenyl groups and/or substituted phenyl groups independently can be a halogen, a primary carbon atom group or a secondary carbon atom group, and the remainder of the 2- and 6-positions of the R$^6$ and R$^7$ phenyl groups and/or substituted phenyl groups can be hydrogen, (3) two of the 2- and 6-positions of the R$^6$ and R$^7$ phenyl groups and/or substituted phenyl groups can be a tertiary carbon atom group, none, or one of the 2- and 6-positions of the R$^6$ and R$^7$ phenyl groups and/or substituted phenyl groups independently can be a halogen, a primary carbon atom group, or a secondary carbon atom group, and the remainder of the 2- and 6-positions of the R$^6$ and R$^7$ phenyl groups and/or substituted phenyl groups can be hydrogen, (4) one or two of the 2- and 6-positions of the R$^6$ and R$^7$ phenyl groups and/or substituted phenyl groups can be a tertiary carbon atom group and the remainder of the 2- and 6-positions of the R$^6$ and R$^7$ phenyl groups and/or substituted phenyl groups can be hydrogen, 5) one or two of the 2- and 6-positions of the R$^6$ and R$^7$ phenyl groups and/or substituted phenyl groups can be a quaternary carbon atom group and the remainder of the 2- and 6-positions of the R$^6$ and R$^7$ phenyl groups and/or substituted phenyl groups can be hydrogen, or 6) all four of the 2- and 6-positions of the R$^6$ and R$^7$ substituted phenyl groups can be fluorine. Each substituent of a substituted aryl group (general or specific) or a substituted phenyl group (general or specific) which can be utilized as R$^6$ and/or R$^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe R$^6$ and/or R$^7$ of the pyridine bisimines and the pyridine bisimine iron salt complexes. Further, one having ordinary skill in the art can recognize the independently described substituted phenyl group(s) which meet the criteria for a substituted phenyl groups (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine iron salt described herein.

In an aspect, each substituted phenyl group which can be utilized as $R^6$ and/or $R^7$ of the pyridine bisimines and the pyridine bisimine iron salt complexes independently can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 3,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 3,5-disubstituted phenyl group; alternatively, a 2,6-disubstituted phenyl group; or alternatively, a 2,4,6-trisubstituted phenyl group. In some aspects, each substituted phenyl group which can be utilized as $R^6$ and/or $R^7$ of the pyridine bisimines and the pyridine bisimine iron salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of 2- and 6-positions of the $R^6$ and $R^7$ substituted phenyl groups can be fluorine. Each substituent of a substituted aryl group (general or specific) or a substituted phenyl group (general or specific) which can be utilized as $R^6$ and/or $R^7$ can be a halide, an alkyl group, or a hydrocarboxy group; alternatively, a halide or an alkyl group; alternatively, a halide or a hydrocarboxy group; alternatively, an alkyl group or a hydrocarboxy group; alternatively, a halide; alternatively, an alkyl group; or alternatively, a hydrocarboxy group. Halides, alkyl groups (general and specific), and hydrocarboxy groups (general and specific) that can be utilized as substituents are independently disclosed herein and can be utilized without limitation, and in any combination, to further describe $R^6$ and/or $R^7$ of the pyridine bisimines and the pyridine bisimine iron salt complexes. Further, one having ordinary skill in the art can recognize the independently described substituted phenyl group(s) which meet the criteria for a substituted phenyl groups (e.g., primary, secondary, tertiary, and quaternary carbon atom groups, among other criteria) and choose the appropriate substituted phenyl group(s) to meet any particular criteria for a substituted phenyl group(s) for a pyridine bisimine and/or a pyridine bisimine iron salt described herein.

In an aspect, $R^6$ and/or $R^7$ of the pyridine bisimines and the pyridine bisimine iron salt complexes independently can be a phenyl group, a 2-methylphenyl group, a 2-ethylphenyl group, a 2-isopropylphenyl group, a 2-tert-butylphenyl group, a 2-(phenyl)phenyl group, a 2-trifluoromethylphenyl group, a 2-fluorophenyl group, a 2-methoxyphenyl group, a 4-methylphenyl group, a 4-ethylphenyl group, a 4-isopropylphenyl group, a 4-tert-butylphenyl group, a 4-fluorophenyl group, a 4-trifluoromethylphenyl group, a 4-methoxyphenyl group, a 2,3-dimethyl phenyl group, a 2-fluoro-3-methylphenyl group, a 2,4-dimethylphenyl group, a 2,4-diethylphenyl group, a 2,4-diisopropylphenyl group, a 2,4-di-tert-butylphenyl group, a 2-fluoro-4-methylphenyl group, a 2,5-dimethylphenyl group, a 2,6-dimethylphenyl group, a 2,6-diethylphenyl group, a 2,6-diisopropylphenyl group, a 2,6-diphenylphenyl group, a 2-fluoro-6-methylphenyl group, a 2,6-bis(trifluoromethyl)phenyl group, a 2,6-difluorophenyl group, a 3,5-dimethylphenyl group, a 3,5-diethylphenyl group, a 3,5-diisopropylphenyl group, a 3,5-di-tert-butylphenyl group, a 3,5-di(trifluoromethyl)phenyl group, or a 2,4,6-trimethylphenyl group. In some aspects, $R^6$ and/or $R^7$ of the pyridine bisimines and the pyridine bisimine iron salt complexes independently can be selected such that (1) one, two, or three of the 2- and 6-positions of the $R^6$ and $R^7$ phenyl groups and/or substituted phenyl groups independently can be a halogen, a primary carbon atom group, or a secondary carbon atom group and the remainder of the 2- and 6-positions of the $R^6$ and $R^7$ phenyl groups and/or substituted phenyl groups can be hydrogen, (2) one of the 2- and 6-positions of the $R^6$ and $R^7$ phenyl groups and/or substituted phenyl groups can be a tertiary carbon atom group, none, one, or two of the 2- and 6-positions of the $R^6$ and $R^7$ phenyl groups and/or substituted phenyl groups independently can be a halogen, a primary carbon atom group or a secondary carbon atom group, and the remainder of the 2- and 6-positions of the $R^6$ and $R^7$ phenyl groups and/or substituted phenyl groups can be hydrogen, (3) two of the 2- and 6-positions of the $R^6$ and $R^7$ phenyl groups and/or substituted phenyl groups can be a tertiary carbon atom group, none, or one of the 2- and 6-positions of the $R^6$ and $R^7$ phenyl groups and/or substituted phenyl groups independently can be a halogen, a primary carbon atom group, or a secondary carbon atom group, and the remainder of the 2- and 6-positions of the $R^6$ and $R^7$ phenyl groups and/or substituted phenyl groups can be hydrogen, (4) one or two of the 2- and 6-positions of the $R^6$ and $R^7$ phenyl groups and/or substituted phenyl groups can be a tertiary carbon atom group and the remainder of the 2- and 6-positions of the $R^6$ and $R^7$ phenyl groups and/or substituted phenyl groups can be hydrogen, 5) one or two of the 2- and 6-positions of the $R^6$ and $R^7$ phenyl groups and/or substituted phenyl groups can be a quaternary carbon atom group and the remainder of the 2- and 6-positions of the $R^6$ and $R^7$ phenyl groups and/or substituted phenyl groups can be hydrogen, or 6) all four of the 2- and 6-positions of the R⁶ and R⁷ substituted phenyl groups can be fluorine. One having ordinary skill in the art can recognize the independently described substituted phenyl group(s) which meet the criteria for a substituted phenyl group (e.g., primary, secondary, and tertiary carbon atom groups, among other criteria) and choose the appropriate substituted phenyl group(s) to meet any particular criteria for a substituted phenyl group(s) for a pyridine bisimine and/or a pyridine bisimine iron salt described herein.

In an aspect, the pyridine bisimine can comprise, consist essentially of, or can be, a 2,6-bis[(arylimine)hydrocarbyl]pyridine, a bis[(substituted arylimine)hydrocarbyl]pyridine, or a [(arylimine)hydrocarbyl], [(substituted arylimine)hydrocarbyl]pyridine; alternatively, a 2,6-bis[(arylimine)hydrocarbyl]pyridine; alternatively, a bis[(substituted arylimine)hydrocarbyl]pyridine; or alternatively, an [(arylimine)hydrocarbyl], or a [(substituted arylimine)hydrocarbyl]pyridine. In an aspect, the pyridine bisimine iron salt complex can comprise, consist essentially of, or can be, a 2,6-bis[(arylimine)hydrocarbyl]pyridine iron salt complex, a bis[(substituted arylimine)hydrocarbyl]pyridine iron salt complex, or a [(arylimine)hydrocarbyl],[(substituted arylimine)hydrocarbyl]pyridine iron salt complex; alternatively, a 2,6-bis[(arylimine)hydrocarbyl]pyridine iron salt complex; alternatively, a bis[(substituted arylimine)hydrocarbyl]pyridine iron salt complex; or alternatively, a [(arylimine)hydrocarbyl],[(substituted arylimine)hydrocarbyl]pyridine iron salt complex. In some aspects, the aryl groups of the 2,6-bis[(arylimine)hydrocarbyl]pyridine or the 2,6-bis[(arylimine)hydrocarbyl]pyridine iron salt complex can be the same or can be different; alternatively, the same; or alternatively, different. In some aspects, the substituted aryl groups of the 2,6-bis[(substituted arylimine)hydrocarbyl]pyridine or the 2,6-bis[(substituted arylimine)hydrocarbyl]pyridine iron salt complex can be the same or can be different; alternatively, the same; or alternatively, different. In an aspect, the pyridine bisimine or the pyridine bisimine of the pyridine bisimine iron salt complex can comprise, consist essentially of, or can be, 2,6-bis[(arylimine)hydrocarbyl]pyridine, a bis[(substituted arylimine)hydrocarbyl]pyridine, and/or an [(arylimine)hydrocarbyl],[(substituted arylimine)hydrocarbyl]-pyridine wherein 1) one, two, or three of the aryl groups and/or substituted aryl groups positions ortho to the carbon atom attached to the imine nitrogen independently can be a halogen, a primary carbon atom group, or a secondary carbon atom group and the remainder of the aryl groups and/or substituted aryl groups positions ortho to the carbon atom attached to the imine nitrogen can be hydrogen, 2) one of the aryl groups and/or substituted aryl groups positions ortho to the carbon atom attached to the imine nitrogen can be a tertiary carbon atom group, none, one, or two of the aryl groups and/or substituted aryl groups positions ortho to the carbon atom attached to the imine nitrogen independently can be a halogen, a primary carbon atom group or a secondary carbon atom group, and the remainder of the aryl groups and/or substituted aryl groups positions ortho to the carbon atom attached to the imine nitrogen can be hydrogen, 3) two of the aryl groups and/or substituted aryl groups positions ortho to the carbon atom attached to the imine nitrogen independently can be a tertiary carbon atom group, none, or one of the aryl groups and/or substituted aryl groups positions ortho to the carbon atom attached to the imine nitrogen independently can be a halogen, a primary carbon atom group, or a secondary carbon atom group, and the remainder of the aryl groups and/or substituted aryl groups positions ortho to the carbon atom attached to the imine nitrogen can be hydrogen, 4) one or two of the aryl groups and/or substituted aryl groups positions ortho to the carbon atom attached to the imine nitrogen independently can be a tertiary carbon atom group(s) and the remainder of the aryl groups and/or substituted aryl groups positions ortho to the carbon atom attached to the imine nitrogen can be hydrogen, 5) one or two of the aryl groups and/or substituted aryl groups positions ortho to the carbon atom attached to the imine nitrogen can be a quaternary carbon atom group and the remainder of the aryl groups and/or substituted aryl groups positions ortho to the carbon atom attached to the imine nitrogen can be hydrogen, or 6) all four of the substituted aryl groups positions ortho to the carbon atom attached to the imine nitrogen can be fluorine. Hydrocarbyl groups (general and specific), aryl groups (general and specific), and substituted aryl groups (general and specific) are independently described herein. The independent descriptions of the hydrocarbyl group, aryl groups, and substituted aryl groups can be utilized without limitation, and in any combination, to further describe the 2,6-bis[(arylimine)hydrocarbyl]pyridine, the bis[(substituted arylimine)hydrocarbyl]pyridine, or the [(arylimine)hydrocarbyl],[(substituted arylimine)hydrocarbyl]-pyridine which can be utilized as the pyridine bisimine or the pyridine bisimine iron salt complex that can be utilized in the processes described herein. One having ordinary skill in the art can recognize the independently described aryl group(s) and/or substituted aryl group(s) which meet the criteria for aryl group and/or substituted aryl groups (e.g., primary, secondary, and tertiary carbon atom groups, among other criteria) and choose the appropriate aryl group(s) and/or substituted aryl group(s) to meet any particular criteria for the aryl group(s) and/or substituted phenyl group(s) for a pyridine bisimine and/or a pyridine bisimine iron salt complex described herein. Further, the iron salt, $FeX_n$, is independently described herein can be combined, without limitation, with the independently described aryl group(s) and substituted aryl group(s) to further describe the appropriate pyridine bisimine iron salt complexes which can be utilized in the processes described herein.

In an aspect, the pyridine bisimine and/or the pyridine bisimine of the pyridine bisimine iron salt complex can be 2,6-bis[(phenylimine) methyl]pyridine, 2,6-bis[(2-methylphenylimine)methyl]-pyridine, 2,6-bis[(2-ethylphenylimine)methyl]pyridine, 2,6-bis[(2-isopropylphenylimine)methyl]pyridine, 2,6-bis[(2,4-dimethylphenylimine)methyl]pyridine, 2,6-bis[(2,6-diethylphenylimine)methyl]pyridine, 2-[(2,4,6-trimethylphenylimine)methyl]-6-[(4-methylphenylimine)methyl]pyridine, 2-[(2,4,6-trimethyl-phenylimine)methyl]-6-[(3,5-dimethylphenylimine)methyl]pyridine, or 2-[(2,4,6-trimethylphenylimine)-methyl]-6-[(4-butylphenylimine)methyl]pyridine. The iron salt, $FeX_n$, is independently described herein and can be combined, without limitation, with the pyridine bisimine(s) to further describe the appropriate pyridine bisimine iron salt complexes which can be utilized in the processes described herein.

Additional descriptions of pyridine bisimine iron salt complexes suitable for use in the present disclosure can be found U.S. Pat. Nos. 5,955,555, 6,103,946, 6,291,733, 6,489,497, 6,451,939, 6,455,660, 6,458,739, 6,472,341, 6,545,108, 6,559,091, 6,657,026, 6,683,187, 6,710,006, 6,911,505, 6,911,506, 7,001,964, 7,045,632, 7,056,997, 7,223,893, 7,456,284, 7,683,149, 7902,415, 7,994,376 and EP 1229020A1.

Generally, the iron salt, the iron salt of the pyridine bisimine iron salt complex, or the iron salt of the α-diimine iron salt complex, can have the formula $FeX_n$. Within the formula of the iron salt having the formula $FeX_n$, X represents a monoanionic species, and n represent the number of monoanionic species (or the iron oxidation state). Generally, the monoanionic species, X, and the number of anionic species (or the iron oxidation state), n, are independent elements of the iron salt and are independently described herein. The iron salt having the formula $FeX_n$ can be described utilizing any aspect and/or embodiment of the monoanionic specie described herein, and any aspect and/or embodiment of the number of monoanionic species (or iron oxidation state) described herein.

Generally, the number of monoanionic species (or the iron oxidation state) of the iron salt, the iron salt of the pyridine bisimine iron salt complex, or the iron salt of the α-diimine iron salt complex, can be any positive value that corresponds to an oxidation state available to an iron atom. In an aspect, the number of monoanionic species, n, of the iron salt or the iron salt of the pyridine bisimine iron salt complex can be 1, 2 or 3; alternatively, 2 or 3; alternatively, 1; alternatively, 2; or alternatively, 3.

Generally, the monoanionic specie, X, of the iron salt, the iron salt of the pyridine bisimine iron salt complex, or the iron salt of the α-diimine iron salt complex, can be any monoanionic specie. In an aspect, the monoanionic specie, X, can be a halide, a carboxylate, a β-diketonate, a hydrocarboxide, a nitrate, or a chlorate. In some aspects, the monoanionic specie, X, of the iron salt, the iron salt of the pyridine bisimine iron salt complex, or the iron salt of the α-diimine iron salt complex, can be a halide, a carboxylate, a β-diketonate, or a hydrocarboxide; or alternatively, a halide, a carboxylate, or a β-diketonate. In any aspect and/or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanionic specie, X, of the iron salt, the iron salt of the pyridine bisimine iron salt complex, or the iron salt of the α-diimine iron salt complex, can be a halide, a carboxylate, a β-diketonate, or an alkoxide. In other aspects, the monoanionic specie, X, of the iron salt, the iron salt of the pyridine bisimine iron salt complex, or the iron salt of the α-diimine iron salt complex can be a halide; alternatively, a carboxylate; alternatively, a β-diketonate; alternatively, a hydrocarboxide; alternatively, an alkoxide; or alternatively, an aryloxide.

Generally, each halide monoanionic specie, X, of the iron salt, the iron salt of the pyridine bisimine iron salt complex, or the iron salt of the α-diimine iron salt complex, independently can be fluorine, chlorine, bromine, or iodine; or alternatively, chlorine, bromine, or iodine. In an aspect, each halide monoanionic specie, X, of the iron salt or the iron salt of the pyridine bisimine iron salt complex can be chlorine; alternatively, bromine; or alternatively, iodine.

Generally, each carboxylate monoanionic specie, X, of the iron salt, the iron salt of the pyridine bisimine iron salt complex, or the iron salt of the α-diimine iron salt complex, independently can be a $C_1$ to $C_{20}$ carboxylate; or alternatively, a $C_1$ to $C_{10}$ carboxylate. In an aspect, each carboxylate of the iron salt, the iron salt of the pyridine bisimine iron salt complex, or the iron salt of the α-diimine iron salt complex, independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, or a decanoate. In some aspects, each carboxylate monoanionic specie, X, of the iron salt, the iron salt of the pyridine bisimine iron salt complex, or the iron salt of the α-diimine iron salt complex, independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, or caprate (n-decanoate; alternatively, n-heptanoate; alternatively, caprylate (n-octanoate); or alternatively, 2-ethylhexanoate. In some aspects, the carboxylate can be triflate (trifluoroacetate).

Generally, each β-diketonate monoanionic specie, X, of the iron salt, the iron salt of the pyridine bisimine iron salt complex, or the iron salt of the α-diimine iron salt complex, independently can be a $C_1$ to $C_{20}$ β-diketonate; or alternatively, a $C_1$ to $C_{10}$ β-diketonate. In an aspect, each β-diketonate monoanionic specie, X, of the iron salt, the iron salt of the pyridine bisimine iron salt complex, or the iron salt of the α-diimine iron salt complex, independently can be acetylacetonate (i.e., 2,4-pentanedionate), hexafluoroacetylacetonate (i.e., 1,1,1,5,5,5-hexafluoro-2,4-pentanedionate), or benzoylacetonate; alternatively, acetylacetonate; alternatively, hexafluoroacetylacetone; or alternatively, benzoylacetonate.

Generally, each hydrocarboxide monoanionic specie, X, of the iron salt, the iron salt of the pyridine bisimine iron salt complex, or the iron salt of the α-diimine iron salt complex, independently can be any $C_1$ to $C_{20}$ hydrocarboxide; or alternatively, any $C_1$ to $C_{10}$ hydrocarboxide. In an aspect, each hydrocarboxide monoanionic specie, X, of the iron salt, the iron salt of the pyridine bisimine iron salt complex, or the iron salt of the α-diimine iron salt complex, independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide monoanionic specie, X, of the iron salt, the iron salt of the pyridine bisimine iron salt complex, or the iron salt of the α-diimine iron salt complex, independently can be methoxide, ethoxide, a propoxide, or a butoxide. In some aspects, each alkoxide monoanionic specie, X, of the iron salt, the iron salt of the pyridine bisimine iron salt complex, or the iron salt of the α-diimine iron salt complex, independently can be methoxide, ethoxide, isopropoxide, or tert-butoxide; alternatively, methoxide; alternatively, an ethoxide; alternatively, an iso-propoxide; or alternatively, a tert-butoxide. In an aspect, each aryloxide monoanionic specie, X, of the iron salt, the iron salt of the pyridine bisimine iron salt complex, or the iron salt of the α-diimine iron salt complex, independently can be phenoxide.

In an aspect, the iron salt, the iron salt of the pyridine bisimine iron salt complex, or the iron salt of the α-diimine iron salt complex, can comprise, or consist essentially of, or can be an iron halide, an iron acetylacetonate, an iron carboxylate, or any combination thereof. In some aspects, the iron salt, the iron salt of the pyridine bisimine iron salt complex, or the iron salt of the α-diimine iron salt complex, can comprise, consist essentially of, or can be, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, iron(II) nitrate, iron(III) nitrate, or any combination thereof; alternatively, iron(II) chloride, iron(III) chloride, iron(II) acetate, iron(III) acetate, iron(II) acetylacetonate, iron(III) acetylacetonate, or any combination thereof; alternatively, iron(II) chloride, iron (III) chloride, iron(II) acetylacetonate, iron(III) acetylacetonate, or any combination thereof; alternatively, iron(II) chloride; alternatively, iron(III) chloride; or alternatively, iron(II) acetylacetonate.

In some aspects, the heteroatomic ligand iron salt (e.g., the iron salt complex) can have a structure selected from the group consisting of ADIFe I

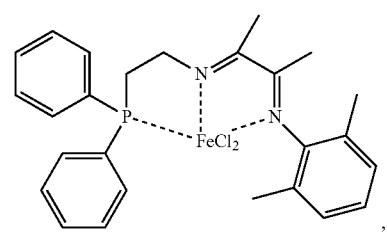

ADIFe II

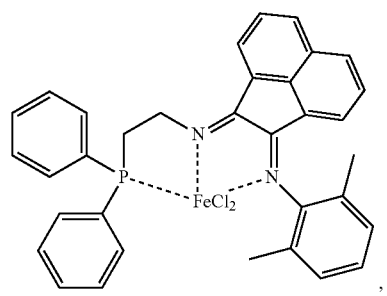

ADIFe III

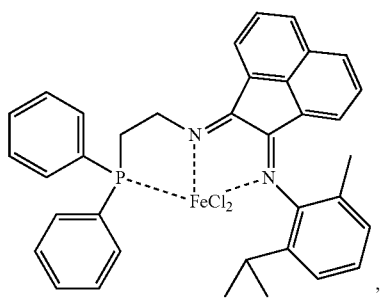

ADIFe IV

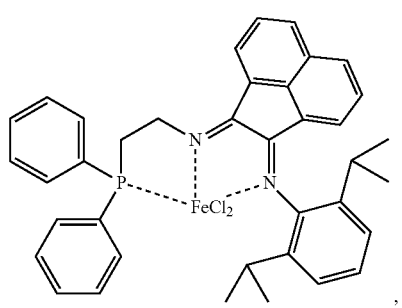

ADIFe V

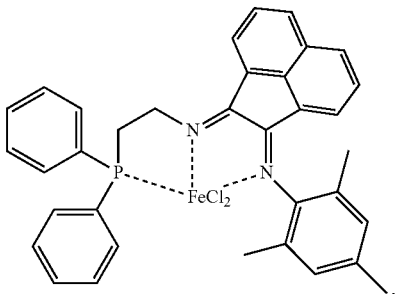

ADIFe VI

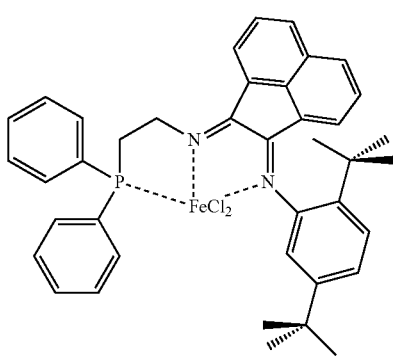

ADIFe VII

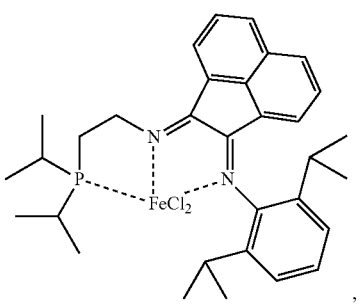

ADIFe VIII

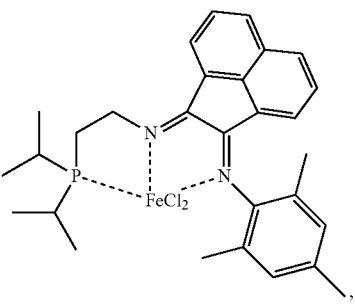

ADIFe IX

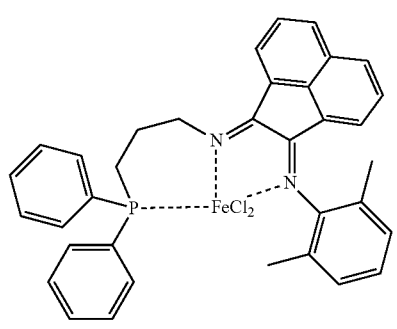

-continued

ADIFe X

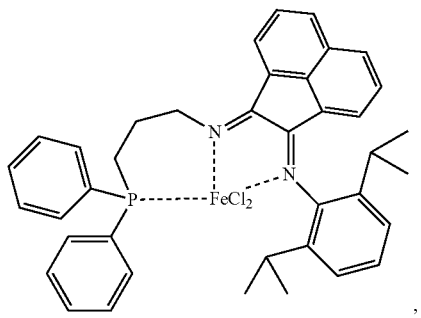

,

ADIFe XII

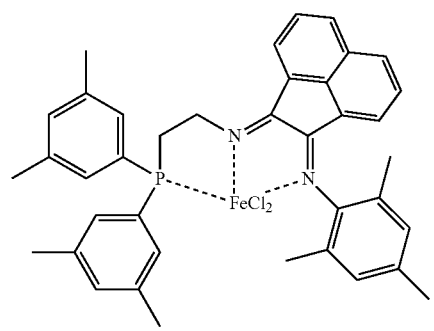

, and

ADIFe XIII

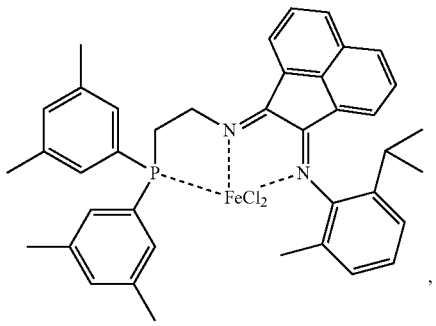

,

In other aspects, the heteroatomic ligand iron salt complex can be selected from the group consisting of 2,6-bis[(phenylimine) methyl]pyridine iron dichloride complex, 2,6-bis[(2-methylphenylimine)methyl]pyridine iron dichloride complex, 2,6-bis[(2-ethylphenylimine)-methyl]pyridine iron dichloride complex, 2,6-bis[(2-isopropylphenylimine) methyl]pyridine iron dichloride complex, 2,6-bis[(2,4-dimethylphenylimine)methyl]pyridine, 2,6-bis[(2,6-diethylphenyl-imine)methyl]pyridine iron dichloride complex, 2-[(2,4,6-trimethylphenylimine)methyl]-6-[(4-methylphenylimine) methyl]pyridine iron dichloride complex, 2-[(2,4,6-trimethylphenylimine)methyl]-6-[(3,5-dimethylphenylimine)methyl]pyridine iron dichloride complex, and 2-[(2,4,6-trimethyl-phenylimine)methyl]-6-[(4-t-butylphenylimine)methyl]pyridine iron dichloride complex.

It should be noted that while not explicitly shown or stated, the iron salts, the pyridine bisimine iron salt complexes, and/or the α-diimine iron salt complexes can further comprise a neutral ligand. While the non-pyridine bisimine neutral ligand and/or non-α-diimine neutral ligand for the iron salts, or the iron salt complexes are not provided in the names, structures, or formulas provided herein, it should be understood that the iron salts, the pyridine bisimine iron salt complexes, the α-diimine iron salt complexes name and depiction do not limit the iron salts, the pyridine bisimine iron salt complexes, and/or the α-diimine iron salt complexes to those not having a non-pyridine bisimine neutral ligand or a non-α-diimine neutral ligand. In fact the iron salts, the pyridine bisimine iron salt complexes, and/or the α-diimine iron salt complexes which can be utilized in any aspect disclosed herein or any aspect disclosed herein can include a non-pyridine bisimine neutral ligand or a non-α-diimine neutral ligand and that these names and depictions provided herein do not limit irons salts or iron salt complexes to those which do not comprise a non-pyridine bisimine neutral ligand or non-α-diimine neutral ligand regardless of the language utilized to describe the iron salts or iron salt complexes. Non-pyridine bisimine neutral ligands and non-α-diimine neutral ligands are provided herein and can be utilized without limitation to further describe the iron salts, the pyridine bisimine iron salt complexes, and/or the α-diimine iron salt complexes.

Generally, the neutral ligand, if present, can be any neutral ligand that forms an isolatable compound with the iron salt, the pyridine bisimine iron salt complex, and/or the α-diimine iron salt complex. In an aspect, each neutral ligand independently can be a nitrile, an ether, or an amine; alternatively, a nitrile; alternatively, an ether; or alternatively, an amine. The number of neutral ligands of the iron salt, the pyridine bisimine iron salt complex, and/or the α-diimine iron salt complex can be any number that forms an isolatable compound with the iron salts, the pyridine bisimine iron salt complexes, and/or the α-diimine iron salt complexes. In an aspect, the number of non-pyridine bisimine or non-α-diimine neutral ligands of the iron salt, the pyridine bisimine iron salt complex, and/or the α-diimine iron salt complex can be 1, 2, 3, 4, 5, or 6; alternatively, 1; alternatively, 2; alternatively, 3; alternatively, 4; alternatively, 5; or alternatively, 6.

Generally, each nitrile ligand which can be utilized as the non-pyridine bisimine or non-α-diimine neutral ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand which can be utilized as the non-pyridine bisimine or non-α-diimine neutral ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile which can be utilized as the non-pyridine bisimine neutral ligand or non-α-diimine independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand which can be utilized as the non-pyridine bisimine or non-α-diimine neutral ligand independently can be a $C_2$ to $C_{40}$ ether; alternatively, a $C_2$ to $C_{30}$ ether; or alternatively, a $C_2$ to $C_{20}$ ether. In an aspect, each ether ligand which can be utilized as the non-pyridine bisimine neutral ligand or non-α-diimine independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether;

alternatively, a $C_3$ to $C_{40}$ aliphatic cyclic ether; or alternatively, a $C_4$ to $C_{40}$ aromatic cyclic ether. In some aspects, each ether ligand which can be utilized as the non-pyridine bisimine or non-α-diimine neutral ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand which can be utilized as the non-pyridine bisimine or non-α-diimine neutral ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand which can be utilized as the non-pyridine bisimine or non-α-diimine neutral ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

In an aspect, each amine which can be utilized as the non-pyridine bisimine or non-α-diimine neutral ligand independently can be a monohydrocarbylamine, a dihydrocarbylamine, or a trihydrocarbylamine, or any combination thereof; alternatively, monohydrocarbylamine; alternatively, a dihydrocarbylamine; or alternatively, a trihydrocarbylamine. Monohydrocarbylamines which can be utilized as the non-pyridine bisimine or non-α-diimine neutral ligand can be a $C_1$ to $C_{30}$, a $C_1$ to $C_{20}$, a $C_1$ to $C_{10}$, or a $C_1$ to $C_5$ monohydrocarbylamine. Dihydrocarbylamines which can be utilized as the non-pyridine bisimine or non-α-diimine neutral ligand can be a $C_2$ to $C_{30}$, a $C_2$ to $C_{20}$, a $C_2$ to $C_{10}$, or a $C_2$ to $C_5$ dihydrocarbylamine. Trihydrocarbylamines which can be utilized as the non-pyridine bisimine or non-α-diimine neutral ligand can be a $C_3$ to $C_{30}$, a $C_3$ to $C_{20}$, or a $C_3$ to $C_{10}$ dihydrocarbylamine. Hydrocarbyl groups (general and specific) are disclosed herein (e.g., as substituent groups, among other places) and can be utilized without limitation to further describe the monohydrocarbylamines, dihydrocarbylamines, and/or trihydrocarbylamines which can be utilized as the non-pyridine bisimine or non-α-diimine neutral ligand. Generally, each hydrocarbyl group of the dihydrocarbylamine (or trihydrocarbylamine) is independent of each other and can be the same: or alternatively, can be different. In a non-limiting aspect, the monohydrocarbylamine, which can be utilized as the non-pyridine bisimine or non-α-diimine neutral ligand can be, comprise, or consist essentially of, methyl amine, ethyl amine, propyl amine, butyl amine, or any combination thereof, alternatively, methyl amine; alternatively, ethyl amine; alternatively, propyl amine; or alternatively, butyl amine. In some aspects, the dihydrocarbylamine, which can be utilized as the non-pyridine bisimine or non-α-diimine neutral ligand can be, comprise, or consist essentially of, dimethyl amine, diethyl amine, dipropyl amine, dibutylamine, or any combination thereof; alternatively, dimethyl amine; alternatively, diethyl amine; alternatively, dipropyl amine; or alternatively, dibutylamine. In some aspects, the trihydrocarbylamine, which can be utilized as the non-pyridine bisimine or non-α-diimine neutral ligand can be, comprise, or consist essentially of, trimethyl amine, triethyl amine, tripropyl amine, tributyl amine, or any combination thereof; alternatively, trimethyl amine; alternatively, triethyl amine; alternatively, tripropyl amine; or alternatively, tributyl amine.

In an aspect, the organoaluminum compound which can be utilized in the processes described herein can comprise an aluminoxane, an alkylaluminum compound, or a combination thereof; alternatively, an aluminoxane; or alternatively, an alkylaluminum compound. In an aspect, the alkylaluminum compound can be a trialkylaluminum, an alkylaluminum halide, an alkylaluminum alkoxide, or any combination thereof. In some aspects, the alkylaluminum compound can be a trialkylaluminum, an alkylaluminum halide, or any combination thereof, alternatively, a trialkylaluminum, an alkylaluminum halide, or any combination thereof; or alternatively, a trialkylaluminum. In other aspects, the alkylaluminum compound can be a trialkylaluminum; alternatively, an alkylaluminum halide; or alternatively, an alkylaluminum alkoxide.

In an aspect, each alkyl group of any organoaluminum compound or any alkylaluminum compound disclosed herein (e.g., trialkylaluminum, alkylaluminum halide, alkylaluminum alkoxide or aluminoxane) independently can be a $C_1$ to $C_{20}$, a $C_1$ to $C_{10}$, or a $C_1$ to $C_6$ alkyl group. In an aspect, each alkyl group of any organoaluminum compound or any alkylaluminum compound disclosed herein (e.g., trialkylaluminum, alkylaluminum halide, alkylaluminum alkoxide, or aluminoxane) independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some aspects, each alkyl group of any organoaluminum compound or any alkylaluminum compound disclosed herein (e.g., trialkylaluminum, alkylaluminum halide, alkylaluminum alkoxide or aluminoxane) independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each halide of any alkylaluminum halide disclosed herein independently can be chloride, bromide, or iodide. In some aspects, each halide of any alkylaluminum halide disclosed herein can be chloride or bromide; or alternatively, or chloride.

In an aspect, each alkoxide group of any alkylaluminum alkoxide disclosed herein independently can be a $C_1$ to $C_{20}$, a $C_1$ to $C_{10}$, or a $C_1$ to $C_6$ alkoxy group. In an aspect, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some aspects, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, the trialkylaluminum compound can comprise, can consist essentially of, or can be, trimethylaluminum, triethylaluminum, tripropylaluminum, tributylaluminum, trihexylaluminum, trioctylaluminum, or mixtures thereof. In some non-limiting aspects, the trialkylaluminum compound can comprise, can consist essentially of, or can be, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting aspects, the trialkylaluminum compound can comprise, can consist essentially of, or can be, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting aspect, the alkylaluminum halide can comprise, can consist essentially of, or can be, diethylaluminum chloride, diethylaluminum bromide, ethylaluminum dichloride, ethylaluminum sesquichloride, and mixtures thereof. In some non-limiting aspects, the alkylaluminum halide can comprise, can consist essentially of, or can be diethylaluminum chloride, ethylaluminum dichloride, ethylaluminum sesquichloride, and mixtures thereof; or alternatively, diethylaluminum chloride; alternatively, diethylaluminum bromide; alternatively, ethylaluminum dichloride; or alternatively, ethylaluminum sesquichloride.

In a non-limiting aspect, the aluminoxane can have a repeating unit characterized by the Formula I:

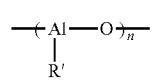

Formula I wherein R' is a linear or branched alkyl group. Alkyl groups for organoaluminum compounds are independently described herein and can be utilized without limitation to further describe the aluminoxanes having Formula I. Generally, n of Formula I is greater than 1; or alternatively, greater than 2. In an aspect, n can range from 2 to 15; or alternatively, range from 3 to 10.

In a non-limiting aspect, the aluminoxane can comprise, can consist essentially of, or can be, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentyl-aluminoxane, 2-entylaluminoxane, 3-pentyl-aluminoxane, iso-pentyl-aluminoxane, neopentylaluminoxane, or mixtures thereof. In some non-limiting aspects, the aluminoxane can comprise, can consist essentially of, or can be, methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

In an aspect, the processes described herein can utilize an organic reaction medium. Generally, the organic reaction medium can act as a solvent and/or a diluent in the processes described herein. In an aspect, the organic reaction medium can comprise, can consist essentially of, or can be, a hydrocarbon, a halogenated hydrocarbon, or a combination thereof; alternatively, a, at least one, or one or more, hydrocarbon(s); or alternatively, a, at least one, or one or more, halogenated hydrocarbon(s). In an aspect, hydrocarbons which can be utilized as the organic reaction medium can be an aliphatic hydrocarbon, an aromatic hydrocarbon, or any combination thereof; alternatively, an, at least one, or one or more aliphatic hydrocarbon(s); or alternatively, an, at least one, or one or more aromatic hydrocarbon(s). In some aspects, the, the at least one, the one or more, aliphatic hydrocarbon(s) which can be utilized as the organic reaction medium can comprise, can consist essentially of, or can be, a saturated aliphatic hydrocarbon, an olefinic aliphatic hydrocarbon, or any combination thereof; alternatively, a, at least one, or one or more saturated aliphatic hydrocarbon(s); or alternatively, an, at least one, or one or more olefinic aliphatic hydrocarbon(s). In an aspect, halogenated hydrocarbons which can be utilized as the organic reaction medium can be a halogenated aliphatic hydrocarbon, a halogenated aromatic hydrocarbon, or any combination thereof; alternatively, a halogenated aliphatic hydrocarbon; or alternatively, a halogenated aromatic hydrocarbon.

In an aspect, the hydrocarbon, aliphatic hydrocarbon, saturated aliphatic hydrocarbon, or olefinic aliphatic hydrocarbon which can be utilized as the organic reaction medium can comprise, consist essentially of, or can be, a, at least one, or one or more, $C_3$ to $C_{18}$, a $C_4$ to $C_{18}$, or a $C_5$ to $C_{10}$ hydrocarbon(s), aliphatic hydrocarbon, saturated aliphatic hydrocarbon(s), or olefinic aliphatic hydrocarbon(s). In other aspects, the, the at least one, or the one or more, aliphatic hydrocarbon(s) (saturated or olefinic) which can useful as an organic reaction medium can comprise, consist essentially of, or can be, a, at least one, or the one or more, $C_8$ to $C_{18}$, a $C_8$ to $C_{16}$, or alternatively, a $C_{10}$ to $C_{14}$ hydrocarbon(s), aliphatic hydrocarbon(s), saturated aliphatic hydrocarbon(s), or olefinic aliphatic hydrocarbon(s). The hydrocarbon(s), aliphatic hydrocarbon(s), saturated aliphatic hydrocarbon(s), or olefinic hydrocarbon(s) can be cyclic or acyclic and/or can be linear or branched, unless otherwise specified.

Non-limiting examples of suitable hydrocarbon organic reaction mediums that can be utilized singly or in any combination include propane, butane(s), pentane(s), hexane(s), heptane(s), octane(s), decane(s), undecane(s), dodecane(s), tridecane(s), tetradecane(s), pentadecane(s), hexadecane(s), heptadecane(s), octadecane(s), hexene(s), heptene(s), octene(s), nonene(s), decene(s), dodecene(s), tetradecene(s), hexadecene(s), octadecene(s), or any combination thereof; alternatively, propane, butane(s), pentane(s), hexane(s), heptane(s), octane(s), decane(s), undecane(s), dodecane(s), tridecane(s), tetradecane(s), pentadecane(s), hexadecane(s), heptadecane(s), octadecane(s), or any combination thereof; or alternatively, hexene(s), heptene(s), octene(s), nonene(s), decene(s), dodecene(s), tetradecene(s), hexadecene(s), octadecene(s), or any combination thereof. In an aspect, suitable acyclic aliphatic hydrocarbon organic reaction mediums that can be utilized can comprise, or can consist essentially of, propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or any combination thereof. In another aspect, a saturated aliphatic hydrocarbon can comprise, or consist essentially of 1-octane, 1-decane, 1-dodecane, 1-tetradecane, 1-hexadecane, 1-octadecane, or any combination thereof; alternatively, 1-decane, 1-dodecane, 1-tetradecane, or any combination thereof; alternatively, 1-decane; alternatively, 1-dodecane; or alternatively, 1-tetradecane. In an aspect, an olefinic aliphatic hydrocarbon which can be utilized as the organic reaction medium can comprise, can consist essentially of, or can be, a, at least one, or one or more, alpha olefin(s); or alternatively, a, at least one, or one or more, normal alpha olefin(s). In a non-limiting aspect, the olefinic aliphatic hydrocarbon which can be utilized as the organic reaction medium can be, comprise, or consist essentially of, 1-octene, 1-decene, 1-dodecene, 1-tetradecene, 1-hexadecene, 1-octadecene, or any combination thereof; alternatively, 1-decene, 1-dodecene, 1-tetradecene, or any combination thereof; alternatively, 1-decene; alternatively, 1-dodecene; or alternatively, 1-tetradecene. In a non-limiting aspect, the cyclic aliphatic hydrocarbon(s) which can be used as an organic reaction medium can comprise, or consist essentially of cyclohexane, methyl cyclohexane, or any combination thereof.

In an aspect, the aromatic hydrocarbon(s) which can be used as an organic reaction medium can comprise, or can consist essentially of, a, at least one, or one or more, $C_6$ to $C_{10}$ aromatic hydrocarbon(s). In a non-limiting aspect, the aromatic hydrocarbon(s) which can be utilized as the organic reaction medium can comprise, or can consist essentially of benzene, toluene, xylene (including ortho-xylene, meta-xylene, para-xylene, or mixtures thereof), ethylbenzene, or combinations thereof.

In an aspect, the halogenated aliphatic hydrocarbon(s) which can be used as the organic reaction medium can comprise, or can consist essentially of, a, at least one, or one or more, $C_1$ to $C_{15}$, $C_1$ to $C_{10}$, or $C_1$ to $C_5$ halogenated aliphatic hydrocarbon(s). The halogenated aliphatic hydrocarbon(s) which can be utilized as an organic reaction medium can be cyclic or acyclic and/or can be linear or branched, unless otherwise specified. In a non-limiting aspect, the halogenated aliphatic hydrocarbon(s) which can be utilized as an organic reaction medium can comprise, or can consist essentially of methylene chloride, chloroform, carbon tetrachloride, dichloroethane, trichloroethane, or combinations thereof.

In an aspect, the halogenated aromatic hydrocarbon(s) which can be useful as the organic reaction medium can comprise, or can consist essentially of, a, at least one, or one or more, $C_6$ to $C_{20}$, or a $C_6$ to $C_{10}$ halogenated aromatic hydrocarbon(s). In a non-limiting aspect, the halogenated aromatic hydrocarbon(s) which can be used as the organic reaction medium can comprise, or can consist essentially of, chlorobenzene, dichlorobenzene, or any combination thereof.

The choice of organic reaction medium can be made on the basis of convenience in processing. For example, isobutane can be chosen to be compatible with solvents and diluents used in processes using the product(s) of the processes described herein (e.g., using the product for the formation of polymer in a subsequent processing step). In some aspects, the organic reaction medium can be chosen to be easily separable from the one or more of the oligomer in the oligomer product. In some aspects, an oligomer of the oligomer product can be utilized as the reaction system solvent.

In an aspect, the oligomer product can be formed in a reaction zone. In an aspect, the reaction zone of any process described herein can comprise a continuous stirred tank reactor, a plug flow reactor, or any combination thereof; alternatively, a continuous stirred tank reactor; or alternatively, a plug flow reactor. In an aspect, the reaction zone of any process described herein can comprise a continuous stirred tank reactor, a loop reactor, a solution reactor, a tubular reactor, a recycle reactor, a bubble reactor, or any combination thereof; alternatively, a continuous stirred tank reactor; alternatively, a loop reactor; alternatively, a solution reactor; alternatively, a tubular reactor; alternatively, a recycle reactor; or alternatively, a bubble reactor. In some aspects, the reaction zone in which the oligomer product can be formed can comprise multiple reactors; or alternatively, only one reactor. When multiple reactors are present, each of the reactors can be the same or can be different types of reactors. Additionally, when reaction zone can comprise more than one reactor, each reactor independently can be any reactor described herein, and the reactors can be arranged in series, parallel, or any combination thereof; alternatively, in series; or alternatively, in parallel.

It should be noted that when reaction zone can comprise multiple reactors, each reactor can be independent of each other (regardless of whether they are operated in series or parallel). As such, the contact modes (if needed), the conditions under which the oligomer product can be formed, the oligomer product formation parameters under which the oligomer product can be formed and/or the reaction zone conditions can be different for each reactor. In particular, when the reaction zone comprises multiple reactors in series, each reactor can be operated to achieve different goals. For example, a first reactor can be operated to i) contact of the ethylene and the catalyst system (e.g., the catalyst system comprising a) a pyridine bisimine iron salt complex and an organoaluminum compound, b) a pyridine bisimine, an iron salt, and an organoaluminum compound, or c) an α-diimine iron salt complex and an organoaluminum compound), and the optional organic reaction medium, ii) initiate production of the oligomer product under a first set of conditions capable of producing the oligomer product to some intermediate ethylene conversion and the effluent of the first reactor transferred to a second reactor operated to achieve the desired ethylene conversion under a second set of conditions capable of producing the oligomer product (with or without additional ethylene, one or more of the catalyst system components (e.g., one or more components of a catalyst system comprising a) a pyridine bisimine iron salt complex and an organoaluminum compound, b) a pyridine bisimine, an iron salt, and an organoaluminum compound, or c) an α-diimine iron salt complex and an organoaluminum compound), and/or the organic reaction medium being added to the reactor/reaction zone.

In any aspect and/or embodiment, the oligomer product can be formed at, the reaction zone can have, or the reaction zone can operate at, conditions that can comprise, either singly or in any combination, an iron of the catalyst system concentration (e.g., iron of the iron salt concentration, iron of the pyridine bisimine iron salt complex concentration, or iron of the α-diimine iron salt complex depending upon the catalyst system utilized), a pyridine bisimine to iron salt equivalent ratio charged to the reaction zone for aspects using a catalyst system comprising an iron salt and a pyridine bisimine, an aluminum of the organoaluminum compound to the iron of the catalyst system molar ratio (e.g., aluminum of the organoaluminum compound to iron of the iron salt molar ratio, aluminum of the organoaluminum compound to iron of the pyridine bisimine iron salt complex molar ratio, or aluminum of the organoaluminum compound to iron of the α-diimine iron salt complex molar ratio depending upon the catalyst system utilized), aluminum of the organoaluminum compound concentration, an ethylene partial pressure, an ethylene to organic reaction medium mass ratio, a temperature (or an average temperature), an Schulz-Flory K value, a hydrogen partial pressure, and/or a hydrogen to ethylene mass ratio. In an aspect, the oligomer product can be formed at, the reaction zone can have, or the reaction zone can operate at, conditions that can comprise, either singly or in any combination, an iron of the catalyst system concentration (e.g., iron of the iron salt concentration, iron of the pyridine bisimine iron salt complex concentration, or iron of the α-diimine iron salt complex depending upon the catalyst system utilized), an aluminum of the organoaluminum compound to the iron of the catalyst system molar ratio (e.g., aluminum of the organoaluminum compound to iron of the iron salt molar ratio, aluminum of the organoaluminum compound to iron of the pyridine bisimine iron salt complex molar ratio, or aluminum of the organoaluminum compound to iron of the α-diimine iron salt complex molar ratio depending upon the catalyst system utilized), an ethylene partial pressure, and an ethylene to organic reaction medium mass ratio; or alternatively, an iron of the catalyst system concentration (e.g., iron of the iron salt concentration, iron of the pyridine bisimine iron salt complex concentration, or iron of the α-diimine iron salt complex depending upon the catalyst system utilized), an aluminum of the organoaluminum compound to the iron of the catalyst system molar ratio (e.g., aluminum of the organoaluminum compound to iron of the iron salt molar ratio, aluminum of the organoaluminum compound to iron of the pyridine bisimine iron salt complex molar ratio, or aluminum of the organoaluminum compound to iron of the α-diimine iron salt complex molar ratio depending upon the catalyst system utilized), an ethylene partial pressure, an ethylene to organic reaction medium mass ratio, and optionally a hydrogen partial pressure or hydrogen to ethylene mass ratio. In another aspect, the oligomer product can be formed at, the reaction zone can have, or the reaction zone can operate at, conditions that can comprise, either singly or in any combination an iron of the catalyst system concentration (e.g., iron of the iron salt concentration, iron of the pyridine bisimine iron salt complex concentration, or iron of the α-diimine iron salt complex depending upon the catalyst system utilized); alternatively, a pyridine bisimine to iron salt equivalent ratio charged to the reaction zone for aspects using a catalyst system comprising an iron salt and a pyridine bisimine; alternatively, an aluminum of the organoaluminum compound to the iron of the catalyst system molar ratio (e.g., aluminum of the organoaluminum compound to iron of the iron salt molar ratio, aluminum of the organoaluminum compound to iron of the pyridine bisimine iron salt complex molar ratio, or aluminum of the organoaluminum compound to iron of the α-diimine iron salt complex molar ratio depending upon the catalyst system utilized); alternatively, aluminum of the organoaluminum compound concentration; alternatively, an ethylene partial pressure; alternatively, an ethylene to organic reaction medium mass ratio; alternatively, a temperature (or an average temperature); alternatively, Schulz-Flory K value; alternatively, hydrogen partial pressure; or alternatively, a hydrogen to ethylene mass ratio.

In any aspect and/or embodiment, the oligomer product can be formed at, the reaction zone can have, or the reaction zone can operate at, a particular iron of the catalyst system concentration (e.g., iron of the iron salt concentration, iron of the pyridine bisimine iron salt complex concentration, or iron of the α-diimine iron salt complex depending upon the catalyst system utilized), hereafter iron concentration or Fe concentration. In an embodiment, the oligomer product can be formed at, the reaction zone can have, or the reaction zone can operate at, a minimum iron concentration $1\times10^{-6}$ mmol Fe/kg, $1\times10^{-5}$ mmol Fe/kg, or $1\times10^{-4}$ mmol Fe/kg based upon the kg mass of the reaction solution; alternatively or additionally, at a maximum iron concentration of $1\times10^{-2}$ mmol Fe/kg, $1\times10^{-2}$ mmol Fe/kg, or $1\times10^{-3}$ mmol Fe/kg based upon the kg mass of the reaction solution. In an embodiment, the oligomer product can be formed at, the reaction zone can have, or the reaction zone can operate at, an iron concentration in the range of any minimum iron concentration disclosed herein to any maximum iron concentration disclosed herein. In a non-limiting embodiment, the oligomer product can be formed, the reaction zone can have, or the reaction zone can operate, at an iron concentration in the range of $1\times10^{-6}$ mmol Fe/kg to $1\times10^{-1}$ mmol Fe/kg, $1\times10^{-5}$ mmol Fe/kg to $1\times10^{-2}$ mmol Fe/kg, or $1\times10^{-4}$ mmol Fe/kg to $1\times10^{-3}$ mmol Fe/kg based upon the kg mass of the reaction solution. Other iron concentration ranges that can be utilized are readily apparent to those skilled in the art with the aid of this disclosure.

In any aspect and/or embodiment wherein the catalyst system comprises an iron salt and a pyridine bisimine, the oligomer product can be formed at, the reaction zone can have, or the reaction zone can operate at, a particular pyridine bisimine to iron salt equivalent ratio charged to the reaction zone (also referred to as a pyridine bisimine to iron salt equivalent ratio). In an embodiment wherein the catalyst system comprises an iron salt and a pyridine bisimine, the oligomer product can be formed at, the reaction zone can have, or the reaction zone can operate at, at a minimum pyridine bisimine to iron salt equivalent ratio (also referred to as a minimum pyridine bisimine to iron salt equivalent ratio) of 0.8:1, 0.9:1, or 0.95:1; alternatively or additionally, a maximum pyridine bisimine to iron salt equivalent ratio (also referred to as a maximum pyridine bisimine to iron salt equivalent ratio) of 4:1, 2:1, 1.5:1, or 1.1:1. In an embodiment, the oligomer product can be formed at, the reaction zone can have, or the reaction zone can operate at, a pyridine bisimine to iron salt equivalent ratio in the range of any minimum pyridine bisimine to iron salt equivalent ratio disclosed herein to any maximum pyridine bisimine to iron salt equivalent ratio disclosed herein. In a non-limiting embodiment, the pyridine bisimine to iron salt equivalent ratio can be in the range of 0.8:1 to 4:1, from 0.9:1 to 2:1, from 0.90:1 to 1.5:1, from 0.95:1 to 1.5:1, or from 0.95:1 to 1.1:1. Other pyridine bisimine to iron salt equivalent ratio ranges that can be utilized are readily apparent to those skilled in the art with the aid of this disclosure.

In any aspect and/or embodiment, the oligomer product can be formed at, the reaction zone can have, or the reaction zone can operate at a particular aluminum of the organoaluminum compound to the iron of the catalyst system molar ratio (e.g., aluminum of the organoaluminum compound to iron of the iron salt molar ratio, aluminum of the organoaluminum compound to iron of the pyridine bisimine iron salt complex molar ratio, or aluminum of the organoaluminum compound to iron of the α-diimine iron salt complex molar ratio depending upon the catalyst system utilized), also referred to as an aluminum:iron molar ratio or Al:Fe molar ratio. In an embodiment, the oligomer product can be formed at, the reaction zone can have, or the reaction zone can operate at, a minimum Al:Fe molar ratio of 100:1, 200:1, 300:1, or 400:1; alternatively or additionally, a maximum reaction zone Al:Fe molar ratio of 5,000:1, 2,000:1, 1,500:1, or 1,000:1. In an embodiment, the oligomer product can be formed at, the reaction zone can have, or the reaction zone can operate at, an Al:Fe molar ratio in the range of any minimum Al:Fe molar ratio disclosed herein to any maximum Al:Fe molar ratio disclosed herein. In a non-limiting embodiment, the oligomer product can be formed at, the reaction zone can have, or the reaction zone can operate at, an Al:Fe molar ratio in the range of 100:1 to 5,000:1, 200:1 to 2,000:1, 300:1 to 1,500:1, 300:1 to 1,500:1, 400:1 to 1,000:1, or 400:1 to 1,000:1. Other Al:Fe molar ratio ranges that can be utilized are readily apparent to those skilled in the art with the aid of this disclosure.

In any aspect and/or embodiment, the oligomer product can be formed at, the reaction zone can have, or the reaction zone can operate at, a particular aluminum of the organoaluminum compound concentration, also referred to as aluminum concentration or Al concentration. In an embodiment, the oligomer product can be formed at, the reaction zone can have, or the reaction zone can operate at, a minimum Al concentration of 0.3 mmol Al/kg, 0.75 mmol Al/kg, 0.9 mmol Al/kg, or 1.1 mmol Al/kg based upon the kg mas of the reaction solution; alternatively or additionally, a maximum Al concentration of 15 mmol Al/kg, 12.5 mmol Al/kg, 10 mmol Al/kg, 7.5 mmol Al/kg, 5 mmol Al/kg, 2.6 mmol Al/kg, 2.2 mmol Al/kg, 1.8 mmol Al/kg, or 1.5 mmol Al/kg based upon the kg mass of the reaction solution. In an embodiment, the oligomer product can be formed at, the reaction zone can have, or the reaction zone can operate at, an Al concentration in the range of any minimum Al concentration disclosed herein to any maximum Al concentration disclosed herein. In a non-limiting embodiment, the oligomer product can be formed at, the reaction zone can have, or the reaction zone can operate at, an Al concentration in the range of 0.3 mmol Al/kg to 15 mmol Al/kg, 0.3 mmol Al/kg to 10 mmol Al/kg, 0.5 mmol Al/kg to 10 mmol Al/kg, 0.5 mmol Al/kg to 7.5 mmol Al/kg, 0.5 mmol Al/kg to 5 mmol Al/kg, 0.75 mmol Al/kg to 2.6 mmol Al/kg, 0.75 mmol Al/kg to 2.2 mmol Al/kg, 0.9 mmol Al/kg to 1.8 mmol Al/kg, 1.1 mmol Al/kg to 1.8 mmol Al/kg, or 1.1 mmol Al/kg to 1.5 mmol Al/kg based upon the kg mass of the reaction solution. Other Al concentration ranges that can be utilized are readily apparent to those skilled in the art with the aid of this disclosure.

In any aspect and/or embodiment, the oligomer product can be formed at, the reaction zone can have, or the reaction zone can operate at, a minimum ethylene partial pressure of 50 psi (344 KPa), 100 psi (689 KPa), 250 psi (1.72 MPa), 500 psi (3.45 MPa), or 800 psi (5.52 MPa); alternatively or additionally, a maximum ethylene partial pressure of 5,000 psi (34.5 MPa), 3,000 psi (20.9 MPa), 2,000 psi (13.8 MPa), 1,500 psi (10.3 MPa), or 1000 psi (6.89 MPa). In an embodiment, the oligomer product can be formed at, the reaction zone can have, or the reaction zone can operate at, an ethylene partial pressure in the range of any minimum ethylene partial pressure disclosed herein to any maximum ethylene partial pressure disclosed herein. In some non-limiting embodiments, the oligomer product can be formed at, the reaction zone can have, or the reaction zone can operate at, an ethylene partial pressure in the range of 50 psi (344 KPa) to 5,000 psi (34.5 MPa), 100 psi (689 KPa) to 3,000 psi (20.9 MPa), 250 psi (1.72 MPa) to 2,000 psi (13.8 MPa), 500 psi (3.45 MPa) to 2,000 psi (13.8 MPa), 500 psi (3.45 MPa) to 1,500 psi (10.3 MPa), or 800 psi (5.52 kPa) to 1000 psi (6.89 MPa). Other ethylene partial pressure ranges are readily apparent to those skilled in the art with the aid of this disclosure.

In any aspect and/or embodiment, the oligomer product can be formed at, the reaction zone can have, or the reaction zone can operate at, a minimum ethylene:organic reaction medium mass ratio of 0.8:1, 1:1, 1.25:1, or 1.5:1; alternatively, or additionally, a maximum ethylene:chromium mass ratio of 4.5:1, 4:1, 3.5:1, 3:1, or 2.5:1. In an embodiment, the oligomer product can be formed at, the reaction zone can have, or the reaction zone can operate at an ethylene:organic reaction medium mass ratio in the range of any minimum ethylene:organic reaction medium mass ratio disclosed herein to any maximum ethylene:organic reaction medium mass ratio disclosed herein. In some non-limiting embodiments, the oligomer product can be formed at, the reaction zone can have, or the reaction zone can operate at, an ethylene:organic reaction medium mass ratio in the range of 0.8:1 to 4.5:1, 1:1 to 4:1, 1:1 to 3.5:1, 1.25:1 to 3:1, or 1.5:1 to 2.5:1. Other ethylene:organic reaction medium mass ratio ranges that can be utilized are readily apparent to those skilled in the art with the aid of this disclosure.

In any aspect and/or embodiment, the oligomer product can be formed at, the reaction zone can have, or the reaction zone can operate at, a minimum reaction zone temperature of 0° C., 25° C., 40° C., 50° C., or 60° C.; alternatively or additionally, a maximum reaction zone reaction zone temperature 200° C., 150° C., 125° C., 110° C., or 100° C. In an embodiment, the oligomer product can be formed at, the reaction zone can have, or the reaction zone can operate at, a reaction zone temperature in the range of any minimum temperature disclosed herein to any maximum temperature disclosed herein. In a non-limiting embodiment, the oligomer product can be formed at, the reaction zone can have, or the reaction zone can operate at, a reaction zone temperature in the range of 0° C. to 200° C., 25° C. to 150° C., 40° C. to 125° C., 50° C. to 125° C., 50° C. to 110° C., or 60° C. to 100° C. Other temperature ranges that can be utilized are readily apparent to those skilled in the art with the aid of this disclosure. In embodiments where the temperature can vary within the reaction zone, the temperature provided herein can alternatively be an average temperature.

In any aspect and/or aspect embodiment, the oligomer product can have a minimum Schulz-Flory K value of (or can be at least) 0.4, 0.45, 0.5 or, 0.55; alternatively or additionally, a maximum value of 0.9, 0.85, 0.8, 0.75, 0.7 or, 0.65. In an embodiment, the oligomer product can have a Schulz-Flory K value in the range of any minimum Schulz-Flory K value disclosed herein to any maximum Schulz-Flory K value disclosed herein. For example, in some non-limiting embodiments, the oligomer product can have a Schulz-Flory K value in the range from 0.4 to 0.9; alternatively, from 0.4 to 0.8; alternatively, from 0.5 to 0.8; alternatively, from 0.5 to 0.7; alternatively, from 0.55 to 0.7. Other oligomer product Schulz-Flory K value ranges are readily apparent from the present disclosure.

In any aspect and/or embodiment, the Schulz-Flory K value can be determined using any one or more of the $C_8$, $C_{10}$, $C_{12}$, $C_{14}$, or $C_{16}$ oligomer product. In an embodiment, Schulz-Flory K value can be an average of any two or more Schulz-Flory K values using different adjacent pairs of produced oligomers described herein. In some embodiments, the Schulz-Flory K value can be an average of any two Schulz-Flory K values described herein; alternatively, any three Schulz-Flory K values described herein; or alternatively, any four Schulz-Flory K values described herein. For example, the Schulz-Flory K value can be determine using the $C_8$ and $C_{10}$ oligomer product; alternatively, the $C_{10}$ and $C_{12}$ oligomer product; alternatively, the $C_{12}$ and $C_{14}$ oligomer product; alternatively, the $C_{14}$ and $C_{16}$ oligomer product; alternatively, the $C_8$, $C_{10}$, and $C_{12}$ oligomer product, or alternatively, the $C_{10}$, $C_{12}$, and $C_{14}$ oligomer product, among other combinations of oligomer product.

In any aspect and/or embodiment wherein hydrogen is utilized, the oligomer product can be formed at, the reaction zone can have, or the reaction zone can operate at, a minimum hydrogen partial pressure of 1 psi (6.9 kPa), 2 psi (14 kPa); 5 psi (34 kPa), 10 psi (69 kPa), 15 psi (103 kPa), 20 psi (138 kPa), 30 psi (206 kPa); alternatively or additionally, a maximum hydrogen partial pressure of 150 psi (1.03 MPa), 100 psi (689 kPa), 75 psi (517 kPa), or 50 psi (345 kPa. In an embodiment, the oligomer product can be formed at, the reaction zone can have, or the reaction zone can operate at, a hydrogen partial pressure in the range of any minimum hydrogen partial pressure disclosed herein to any maximum hydrogen partial pressure disclosed herein. In some non-limiting embodiments wherein hydrogen is utilized, the oligomer product can be formed at, the reaction zone can have, or the reaction zone can operate at, a hydrogen partial pressure in the range of 1 psi (6.9 kPa) to 150 psi (1.4 MPa), from 5 psi (34 kPa) to 100 psi (689 kPa), from 10 psi (69 kPa) to 100 psi (689 kPa), or from 15 psi (100 kPa) to 75 psi (517 kPa). Other hydrogen partial pressure ranges that can be utilized are readily apparent to those skilled in the art with the aid of this disclosure.

In any aspect and/or embodiment wherein hydrogen is utilized, the oligomer product can be formed at, the reaction zone can have, or the reaction zone can operate at, a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed at, the reaction zone can have, or the reaction zone can operate at, a hydrogen to ethylene mass ratio in the range of any minimum hydrogen to ethylene mass ratio disclosed herein to any maximum hydrogen to ethylene mass ratio disclosed herein. In some non-limiting embodiments, the oligomer product can be formed at, the reaction zone can have, or the reaction zone can operate at, a hydrogen to ethylene mass ratio in the range of (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

In any aspect and/or embodiment, the processes described herein can produce an oligomer product with high selectivity to linear alpha olefins; or alternatively, to normal alpha olefins. In some embodiments, the processes described herein can produce a reactor effluent wherein the $C_6$ olefin oligomer product has a 1-hexene content of at least 98.5 wt. %; alternatively, at least 98.75 wt. %; alternatively, at least 99.0 wt. %; or alternatively, at least 99.25 wt. %. In other embodiments, the processes described herein can produce a reactor effluent wherein the $C_8$ olefin oligomer product has a 1-octene content of at least 98 wt. %; alternatively, at least 98.25 wt. %; alternatively, at least 98.5 wt. %; alternatively, at least 98.75 wt. %; or alternatively, at least 99.0 wt. %. In yet other embodiments, the processes described herein can produce a reactor effluent wherein the $C_{10}$ olefin oligomer product has a 1-decene content of at least 97.5 wt. %; alternatively, at least 97.75 wt. alternatively, at least 98 wt. %; alternatively, at least 98.25 wt. %; or alternatively, at least 98.5 wt. %. In yet other embodiments, the processes described herein can produce a reactor effluent wherein the $C_{12}$ olefin oligomer product has a 1-dodecene content of at least 96.5 wt. %; alternatively, at least 97 wt. %; alternatively, at least 97.5 wt. %; alternatively, at least 97.75 wt. %; or alternatively, at least 98.0 wt. %. In yet other embodiments, the processes described herein can produce a reactor effluent wherein the oligomer product can comprise any combination of any $C_6$ olefin oligomer product 1-hexene content described herein, any $C_8$ olefin oligomer product 1-octene content described herein, any $C_{10}$ olefin oligomer product 1-decene content described herein, and/or any olefin oligomer product 1-dodecene content described herein. In some non-limiting examples, the processes described herein can produce a reactor effluent having a $C_6$ olefin oligomer product 1-hexene content of at least 99 wt. % and a C olefin oligomer product 1-dodecene content of at least 97.5 wt. %; alternatively, a $C_8$ olefin oligomer product 1-octene content of at least 98.5 wt. % and a $C_{12}$ olefin oligomer product 1-dodecene octene content of at least 97.5 wt. %; or alternatively, a $C_5$ olefin oligomer product 1-hexene content of at least 99 wt. %, a $C_8$ olefin oligomer product 1-octene content of at least 98.5 wt. %, a $C_{10}$ olefin oligomer product 1-decene content of at least 98 wt. %, and a olefin oligomer product 1-dodecene content f at least 97.5 wt. %. Other combinations of reactor effluent olefin oligomer 1-alkene contents are readily apparent from the present disclosure.

In some aspects and/or embodiments, the processes, systems, and reaction systems described herein can produce less wax and/or polymer product per gram of oligomer product than an otherwise similar process which does not operate within the disclosed ranges of hydrogen partial pressure and/or hydrogen to ethylene mass ratio. Herein a "wax"

refers to a products having from 30 to 70 carbon atoms while a "polymer" refers to products having greater than 70 carbon atoms. In any aspect and/or embodiment, the processes, systems, and reaction systems described herein can produce an oligomer product wherein the amount of polymer product produced per gram of oligomer product produced can be decreased by at least 10%, 25%, 40%, 50%, 60%, 70%, or 80% as compared to an oligomer product produced by a similar oligomerization process, system, and/or reaction system operating in the substantial absence of hydrogen. In any aspect and/or embodiment, the processes, systems, and reaction systems described herein can produce an oligomer product wherein the amount of wax produced per gram of oligomer product produced can be decreased by at least 10%, 25%, 40%, 50%, 60%, 70%, or 80% as compared to an oligomer product produced by a similar oligomerization process, system, and/or reaction system operating in the substantial absence of hydrogen.

In some aspects and/or embodiments, the processes, systems, and reaction systems described herein utilizing hydrogen can produce an oligomer product having a particular amount of polymer, a particular amount compounds having greater than 70 carbon atoms, a particular amount of compounds having an weight average molecular weight greater than 1000 g/mol, or any combination thereof; alternatively, an oligomer product having a particular amount of polymer; alternatively, a particular amount compounds having greater than 70 carbon atoms; or alternatively, a particular amount of compounds having an weight average molecular weight greater than 1000 g/mol. In any aspect and/or embodiment, the amount of polymer produced by the processes, systems, and reaction systems described herein utilizing hydrogen can be less than 1, 0.75, 0.5, or 0.25 wt. % based upon the total weight of oligomer product produced. In any aspect and/or embodiment, the amount of compounds having greater than 70 carbon atoms produce by processes, systems, and reaction systems described herein utilizing hydrogen can be less than 1, 0.75, 0.5, or 0.25 wt. % based upon the total weight of oligomer product produced. In any aspect and/or embodiment, the amount of compounds having a weight average molecular weight greater than 1000 g/mol produced by processes, systems, and reaction systems described herein utilizing hydrogen can be less than 1, 0.75, 0.5, or 0.25 wt. % based upon the total weight of oligomer product produced.

Without being limited by theory, it is believed that the addition of hydrogen to the oligomerization processes, systems, and/or reaction systems can increase the amount of saturated oligomers (paraffin) in the oligomer product fractions. Consequently, while the addition of hydrogen to the oligomerization processes, systems, and/or reaction systems can have potential benefits (e.g., reducing the amount of polymer produce), the benefit can be adversely impacted reducing the purity of the oligomer product fractions. In some aspects and/or embodiments wherein hydrogen is utilized, the processes, systems, and reaction systems described herein can produce an oligomer product wherein each carbon number fraction from $C_4$ to $C_{18}$ of the oligomer product has a paraffin content of equal to or less than 2 times, 1.8 times, 1.6 times, or 1.4 times the paraffin content of a corresponding carbon number fraction of the oligomer product produced by a similar oligomerization process, system, and/or reaction system operating in the substantial absence of hydrogen. Generally, in these aspects and/or embodiments, the weight percentage of paraffin is based on the total weight of the carbon number fraction of the oligomer product. It should be noted that the physical separation of the carbon number fractions by physical fractionation of the oligomer product prior to the measurement of the paraffin content is not required to measure the paraffin content as the measurement of the paraffin content of the carbon number fractions can be made using analytic techniques (e.g., gas chromatography, among other techniques) applied to all or a portion of the oligomer product.

Without being limited by theory, it is believe that the addition of hydrogen to the oligomerization processes, systems, and/or reaction systems can decrease the Schulz-Flory K value of the oligomer product. Consequently, while the addition of hydrogen to the oligomerization processes, systems, and/or reaction systems can have potential benefits (e.g., reducing the amount of polymer produce), the benefit can be adversely impacted reducing the Schulz-Flory K value of the oligomer product. In some aspects and/or embodiments wherein hydrogen is utilized, the processes, systems, and reaction systems described herein can produce an oligomer product fraction having a Schulz-Flory K value within ±5, 4.5, 4, 3.5, 3, 2.5, or 2% of the Schulz-Flory K value of a corresponding oligomer product produced by a similar oligomerization process, system, and/or reaction system operating in the substantial absence of hydrogen.

In any aspect or embodiment disclosed herein, the one or more of any of the effects of hydrogen on any process described herein can be observed in any aspect of embodiment of the processes described herein.

In an embodiment, the substantial absence of hydrogen as it relates to condition at which the oligomer product is formed, the conditions of the reaction zone, or the condition for operating the reaction zone for the processes described herein can be a hydrogen partial pressure of less than 0.5 psi (3.4 kPa) 0.25 psi (1.7 kPa), 0.1 psi (0.69 kPa), 0.05 psi (0.34 kPa), 0.025 psi (0.17 kPa), or 0.01 psi (0.069 kPa). In another embodiment, the substantial absence of hydrogen as it relates to condition at which the oligomer product is formed, the conditions of the reaction zone, or the condition for operating the reaction zone for the processes described herein can be a hydrogen to ethylene mass ratio of (0.025 g hydrogen)/(kg ethylene), (0.01 g hydrogen)/(kg ethylene), (0.005 g hydrogen)/(kg ethylene), (0.0025 g hydrogen)/(kg ethylene), or (0.001 g hydrogen)/(kg ethylene).

Various aspects and/or embodiments described herein can refer to substituted groups or compounds. In an embodiment, each substituent of any aspect and/or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl group or substituent of any aspect and/or embodiment calling for a substituent can be a $C_1$ to $C_{10}$, or a $C_1$ to $C_5$ hydrocarbyl group. In an embodiment, each hydrocarboxy group or substituent of any aspect and/or embodiment calling for a substituent can be a $C_1$ to $C_{10}$, or a $C_1$ to $C_5$ hydrocarboxy group. In an embodiment, any halide substituent of any aspect and/or embodiment calling for a substituent can be a fluoride, chloride, bromide, or iodide; alternatively, a fluoride or chloride. In some embodiments, any halide substituent of any aspect and/or embodiment calling for a substituent can be a fluoride; alternatively, a chloride; alternatively, a bromide; or alternatively, an iodide.

In an embodiment, any hydrocarbyl group or substituent of any aspect and/or embodiment calling for a substituent can be an alkyl group, an aryl group, or an aralkyl group;

alternatively, an alkyl group; alternatively, an aryl group; or alternatively, an aralkyl group. In an embodiment, any alkyl group of any aspect and/or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl group of any aspect and/or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl group of any aspect and/or aspect calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy group or substituent of any aspect and/or embodiment calling for a substituent can be an alkoxy group, an aryloxy group, or an aralkoxy group; alternatively, an alkoxy group; alternatively, an aryloxy group, or an aralkoxy group. In an embodiment, any alkoxy group of any aspect and/or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy group of any aspect and/or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an aspect, any aralkoxy group of any aspect or aspect calling for a substituent can be benzoxy group.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the examples are given to show particular aspects and/or embodiments of the compounds, catalyst systems, and olefin oligomerization and/or olefin polymerization methods disclosed, and to demonstrate a number of the practices and advantages thereof. The examples are given as a more detailed demonstration of some of the aspects and/or embodiments described herein and are not intended to limit the disclosure or claims in any manner.

Additional Disclosure

The following enumerated aspects of the present disclosures are provided as non-limiting examples.

A first aspect which is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product wherein (1) the oligomer product has a Schulz-Flory K value from 0.4 to 0.8 and (2) the oligomer product comprises (a) less than 1 wt. % of polymer, (b) less than 1 wt. % compounds having greater than 70 carbon atoms, (c) less than 1 wt. % compounds having a weight average molecular weight of greater than 1000 g/mol, or (d) any combination thereof wherein the weight percentage is based on the total weight of the oligomer product.

A second aspect which is the process of the first aspect, wherein each carbon number fraction from $C_4$ to $C_{18}$ of the oligomer product has a paraffin content equal to or less than 2 times the paraffin content of a corresponding carbon number fraction of the oligomer product produced in a similar process operating in the substantial absence of hydrogen based on the total weight of the carbon number fraction of the oligomer product.

A third aspect which is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product wherein 1) the oligomer product has a Schulz-Flory K value from 0.4 to 0.8, and 2) each single carbon number fraction from $C_4$ to $C_{18}$ of the oligomer product has a paraffin content equal to or less than 2 times the paraffin content of a corresponding carbon number fraction of the oligomer product produced by a similar process operating in the substantial absence of hydrogen based on the total weight of the carbon number fraction of the oligomer product.

A fourth aspect which is the process of the third aspect, wherein the oligomer product comprises (a) less than 1 wt. % of polymer, (b) less than 1 wt. % compounds having greater than 70 carbon atoms, (c) less than 1 wt. % compounds having a weight average molecular weight greater than 1000 g/mole, or (d) any combination thereof wherein the weight percentage is based on the total weight of the oligomer product.

A fifth aspect which is a process comprising a) contacting (i) ethylene, (ii) a catalyst system comprising a heteroatomic ligand iron salt complex, or a heteroatomic ligand and an iron salt, (iii) hydrogen, and (iv) optionally an organic reaction medium; and b) forming an oligomer product having a Schulz-Flory K value of from 0.4 to 0.8 with a Schulz-Flory K value that is within ±5% of the Schulz-Flory K value of a corresponding oligomer product produced by a similar process operating in the substantial absence of hydrogen.

A sixth aspect which is the process of the fifth aspect, wherein each carbon number fraction from $C_4$ to $C_{18}$ of the oligomer has a paraffin content equal to or less than 2 times the paraffin content of a corresponding carbon number fraction of the oligomer product produced by a similar process operating in the substantial absence of hydrogen based on the total weight of the carbon number fraction of the oligomer product.

A seventh aspect which is the process of any of the fifth or sixth aspects, wherein the oligomer product comprises (a) less than 1 wt. % of polymer, (b) less than 1 wt. % compounds having greater than 70 carbon atoms, (c) less than 1 wt. % compounds having a Mw greater than 1000, or (d) any combination thereof wherein the weight percentage is based on the total weight of the oligomer product.

An eighth aspect which is the process of any of the first through seventh aspects, wherein the oligomer product is formed at a hydrogen to ethylene mass ratio in the range of 0.05 g $H_2$/kg ethylene to 5 g $H_2$/kg ethylene.

A ninth aspect which is the process of any of the first through eighth aspects, wherein the catalyst system comprises the heteroatomic ligand iron salt complex and the heteroatomic ligand iron salt complex is an α-diimine iron salt complex.

A tenth aspect which is the process of the ninth aspect, wherein the α-diimine comprises i) an α-diimine group, ii) a first imine group consisting of a hydrocarbyl group or substituted hydrocarbyl group attached to a first imine nitrogen atom of the α-diimine group, and iii) a second imine group comprising an iron salt complexing group and a linking group linking the iron salt complexing group to a second imine nitrogen atom of the α-diimine group.

An eleventh aspect which is the process of the ninth aspect wherein the α-diimine of the α-diimine iron salt complex comprises i) an α-diimine group derived from an aromatic diacyl compound, ii) a first imine group consisting of an aryl group or substituted aryl group, and iii) a second imine group comprising a diarylphosphinyl iron salt complexing group and a —$CH_2CH_2$— linking group linking the iron salt complexing group to the second imine nitrogen atom.

A twelfth aspect which is the process of the ninth aspect wherein the α-diimine comprises i) an α-diimine group derived from acenaphthenequinone, phenanthrenequinone, or pyrenequinone, ii) a first imine group consisting of an 2,6-dihydrocarbylphenyl group, and iii) a second imine group comprising a diphenylphosphinyl iron salt complex-ing group or a di(substituted phenyl)phosphinyl iron complexing group and a —$CH_2CH_2$— linking group linking the iron salt complexing group to the second imine nitrogen atom.

A thirteenth aspect which is the process of any of the ninth aspect, wherein the heteroatomic ligand iron salt complex has a structure selected from the group consisting of

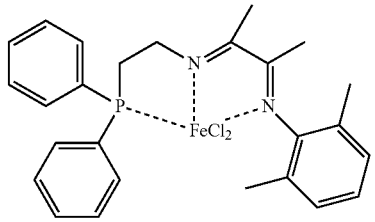

ADIFe I

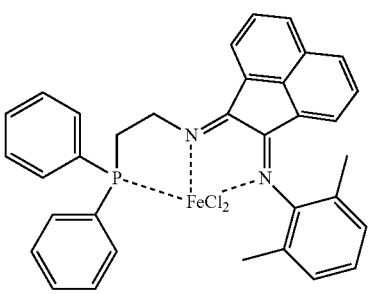

ADIFe II

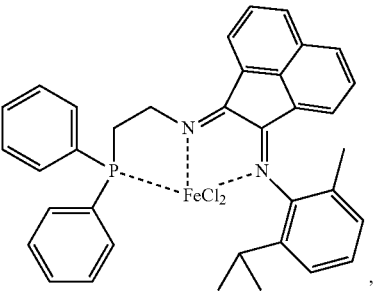

ADIFe III

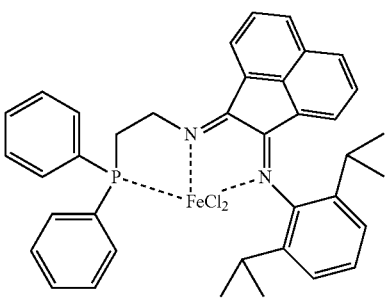

ADIFe IV

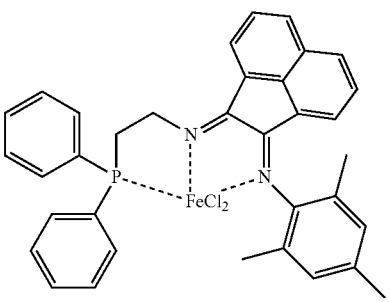

ADIFe V

,

ADIFe VI

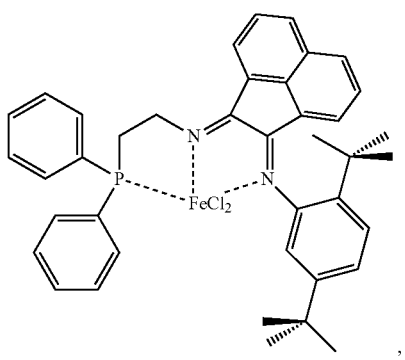

,

ADIFe VII

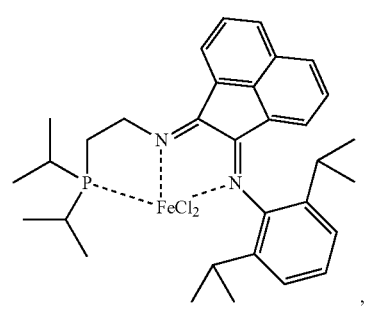

,

ADIFe VIII

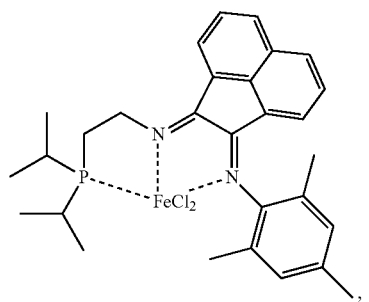

,

ADIFe IX

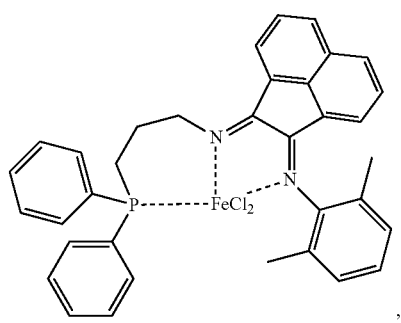

,

ADIFe X

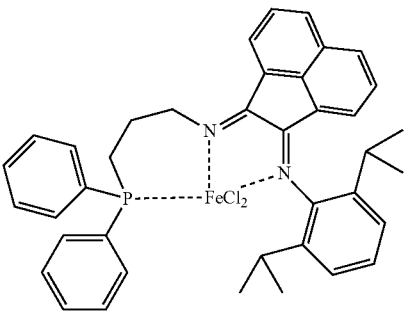

,

ADIFe XII

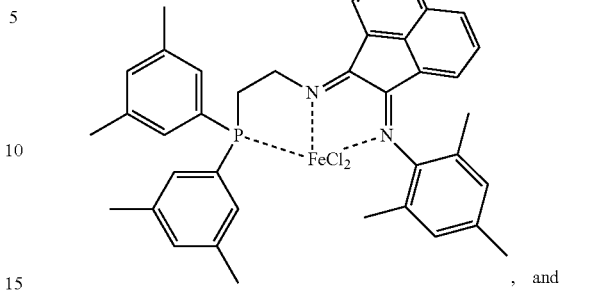

, and

ADIFe XIII

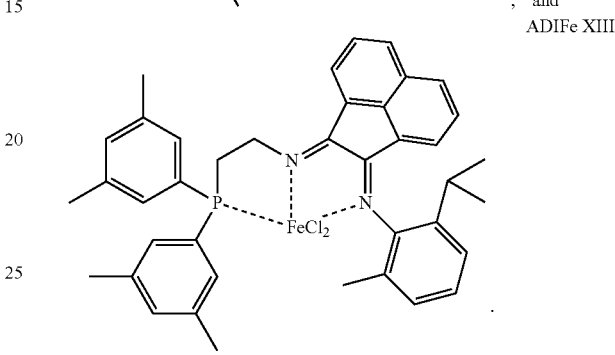

.

A fourteenth aspect which is the process of any of the first through eighth aspects, wherein the catalyst system comprises heteroatomic ligand iron salt complex, or a heteroatomic ligand and an iron salt, and the heteroatomic ligand or the heteroatomic ligand of the heteroatomic ligand iron salt complex is a pyridine bisimine.

An fifteenth aspect which is the process of the fourteenth aspect, wherein the pyridine bisimine comprises i) a 2,6-bis[(arylimine)hydrocarbyl]pyridine wherein the aryl groups can be the same or different, ii) a bis[(substituted arylimine)hydrocarbyl]pyridine wherein the substituted aryl groups can be the same or different, or iii) an [(arylimine)hydrocarbyl],[(substituted arylimine)hydrocarbyl]pyridine.

An fifteenth aspect which is the process of the fourteenth aspect, wherein 1) one, two, or three of the aryl groups and/or substituted aryl groups positions ortho to the carbon atom attached to the imine nitrogen independently are a halogen, a primary carbon atom group, or a secondary carbon atom group and the remainder of the aryl groups and/or substituted aryl groups positions ortho to the carbon atom attached to the imine nitrogen are hydrogen, 2) one of the aryl groups and/or substituted aryl groups positions ortho to the carbon atom attached to the imine nitrogen is a tertiary carbon atom group, none, one, or two of the aryl groups and/or substituted aryl groups positions ortho to the carbon atom attached to the imine nitrogen independently are a halogen, a primary carbon atom group or a secondary carbon atom group, and the remainder of the aryl groups and/or substituted aryl groups positions ortho to the carbon atom attached to the imine nitrogen are hydrogen, 3) two of the aryl groups and/or substituted aryl groups positions ortho to the carbon atom attached to the imine nitrogen independently are a tertiary carbon atom group, none, or one of the aryl groups and/or substituted aryl groups positions ortho to the carbon atom attached to the imine nitrogen independently are a halogen, a primary carbon atom group, or a secondary carbon atom group, and the remainder of the aryl groups and/or substituted aryl groups positions ortho to the carbon atom attached to the imine nitrogen are hydrogen, 4) one or two of the aryl groups and/or substituted aryl groups positions ortho to the carbon atom attached to the imine nitrogen independently are a tertiary carbon atom group(s) and the remainder of the aryl groups and/or substituted aryl groups positions ortho to the carbon atom attached to the imine nitrogen are hydrogen, 5) one or two of the aryl groups and/or substituted aryl groups positions ortho to the carbon atom attached to the imine nitrogen are a quaternary carbon atom group and the remainder of the aryl groups and/or substituted aryl groups positions ortho to the carbon atom attached to the imine nitrogen are hydrogen, or 6) all four of the substituted aryl groups positions ortho to the carbon atom attached to the imine nitrogen are fluorine.

A seventeenth aspect which is the process fourteenth aspect, wherein the heteroatomic ligand of the heteroatomic ligand iron salt complex is selected from the group consisting of 2,6-bis[(phenylimine) methyl]pyridine, 2,6-bis[(2-methylphenylimine)methyl]pyridine, 2,6-bis[(2-ethylphenylimine)-methyl]pyridine, 2,6-bis[(2-isopropylphenylimine)methyl]pyridine, 2,6-bis[(2,4-dimethylphenylimine)-methyl]pyridine, 2,6-bis[(2,6-diethylphenylimine)methyl]pyridine, 2-[(2,4,6-trimethylphenylimine)-methyl]-6-[(4-methylphenylimine)methyl]pyridine, 2-[(2,4,6-trimethylphenylimine)methyl]-6-[(3,5-dimethylphenylimine)methyl]pyridine, and 2-[(2,4,6-trimethylphenylimine)methyl]-6-[(4-t-butylphenyl-imine)methyl]pyridine.

An eighteenth aspect which is the process of any of the ninth through twelfth aspects or fourteenth through seventeenth aspects, wherein the iron salt comprises an iron halide, an iron acetylacetonate, an iron carboxylate, or any combination thereof.

A nineteenth aspect which is the process of any of the first through eighteenth aspects, wherein the catalyst system further comprises an organoaluminum compound.

A twentieth aspect which is the process of any of the first through eighteenth aspects, wherein the organoaluminum compound comprises an aluminoxane.

A twenty first aspect which is the process of any of the first through twentieth aspects, wherein a $C_6$ oligomer product has a 1-hexene content of at least 98.5 wt. %.

A twenty second aspect which is the process of any of the first through twenty first aspects, wherein a $C_8$ oligomer product has a 1-octene content of at least 98 wt. %.

A twenty third aspect which is the process of any of the first through twenty second aspects, wherein a $C_{10}$ oligomer product has a 1-decene content of at least 97.5 wt. %.

An twenty fourth aspect which is the process of any of the first through twenty third aspects, wherein a $C_{12}$ oligomer product has a 1-dodecene content of at least 96.5 wt. %.

EXAMPLES

All operations were performed in an oxygen free and moisture free environment. Solvents were dried over 13× molecular sieves, and ethylene was purified using in-stream de-oxygenation and moisture removal beds. MMAO-3A was purchased from Akzo Nobel.

Examples 1-6

Figure 2:
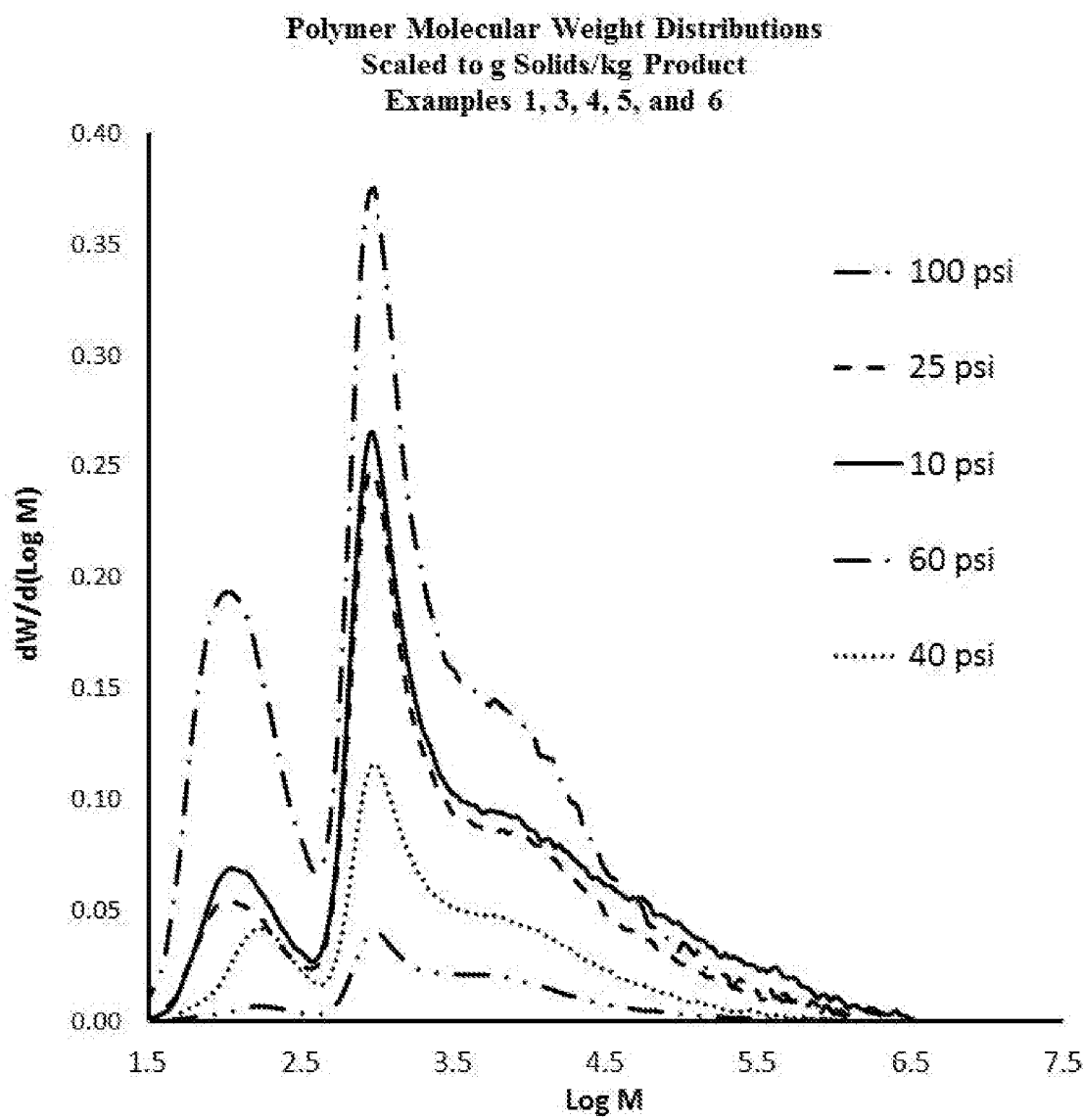
FIG. 2 provides a plot of the molecular weight of the polymer produced in Examples 1, 3, 4, 5, and 6 scaled to the mass of polymer produced per mass of oligomer product produced.

In a nitrogen filled drybox, a 6 mL toluene stock solution containing 1 μmol of ADIFe XIII was charged to a 10 mm NMR tube and sealed. Also in the drybox, a 500 mL glass charger was prepared with 200 mL of cyclohexane, 2 mL n-nonane, and 0.27 mL of 7 wt. % of MMAO-3A and then sealed with a rubber septum. The NMR tube and charger were removed from the drybox. The NMR tube was secured to the stirrer shaft of a 500 mL autoclave reactor with wire in a manner where the glass would shatter on starting the mixer. The autoclave reactor was then sealed and evacuated under high vacuum. The addition funnel was affixed to a charging port on the top of the autoclave reactor. After evacuating the reactor for several minutes, the entire contents of the addition funnel were loaded into the autoclave reactor under vacuum. The autoclave reactor was then degassed with ethylene by carrying out several fill/vent cycles. Following the final vent cycle, the reactor was backfilled to a desired pressure of hydrogen. The reactor was then pressurized with ethylene to 600 psig (4.1 mPa). Stirring was initiated resulting in breakage of the 10 mm NMR tube and activation of the catalyst. Ethylene was then fed to the autoclave reactor on demand to maintain a pressure of 600 psig (4.1 mPa) for the remainder of the reaction. The reaction temperature was moderated by way of cooling water passed through internal cooling coils inside the autoclave reactor. The reactor temperature, following the initial exotherm, was maintained at 60° C. After 30 min, the reactor was cooled to room temperature and vented to atmospheric pressure. The reactor was lowered and the liquid contents measured by way of a graduated cylinder. The contents were allowed to cool and sit for at least one hour prior to being filtered over a filter frit to isolate the reaction solids. The liquid products were analyzed by a gas chromatograph with a flame ionization detector (FID) detector against the n-nonane internal standard. The solids (waxes>$C_{100}$ and polyethylene) were analyzed by gel permeation chromatography (GPC) using Chevron Phillips Chemicals Company's HDPE polyethylene resin, MARLEX® BHB5003, as the broad molecular weight standard. Calibration samples of MARLEX® BHB5003 can be obtained from Chevron Phillips Chemicals Company, LP. Table 1 details the results of these ethylene oligomerization runs. FIG. 1 provides a plot of the molecular weight of the polymer produced in Examples 1, 3, 4, 5, and 6. FIG. 2 provides a plot of the molecular weight of the polymer produced in Examples 1, 3, 4, 5, and 6 scaled to the mass of polymer produced per mass of oligomer product produced.

TABLE 1

| Example | Al, ppm by mass | Al:Cat, Molar Ratio | $H_2$ Pressure, psi (kPa) | Productivities | | | Schulz-Flory K value | $T_{max}$, ° C. |
| | | | | g Prod/ g bisimine Fe Complex | g Prod/ g Al | g Solid/ kg Prod | $C_{12}/C_{10}$ | |
| --- | --- | --- | --- | --- | --- | --- | --- | --- |
| 1 | 85 | 497 | 100 (689) | 103,614 | 5,459 | 1.5 | 0.541 | 49 |
| 2 | 85 | 497 | 80 (552) | 103,313 | 5,444 | 0.0 | 0.578 | 53 |

TABLE 1-continued

| Example | Al, ppm by mass | Al:Cat, Molar Ratio | H$_2$ Pressure, psi (kPa) | Productivities g Prod/ g bisimine Fe Complex | g Prod/ g Al | g Solid/ kg Prod | C$_{12}$/C$_{10}$ Schulz-Flory K value | T$_{max}$, °C. |
|---|---|---|---|---|---|---|---|---|
| 3 | 85 | 497 | 60 (414) | 139,444 | 7,347 | 11.2 | 0.545 | 58 |
| 4 | 85 | 497 | 40 (276) | 132,661 | 6,990 | 3.5 | 0.541 | 59 |
| 5 | 85 | 497 | 25 (172) | 115,951 | 6,110 | 5.5 | 0.542 | 60 |
| 6 | 85 | 497 | 10 (69) | 109,029 | 5,745 | 6.9 | 0.556 | 61 |

The results of Example 1-6 demonstrate that increasing H$_2$ relative to ethylene feed reduces the weight percent of generated polymer to effectively zero.

Examples 7-10

In an N$_2$ filled glovebox, a solution of ADIFe XIII was prepared at 0.25 mg/mL in dichloromethane and loaded into a glass charger. A solution of MMAO-3A was prepared at 0.1 mL/mL in anhydrous n-nonane and loaded into a glass charger. The chargers were removed from the glovebox and charged to the separate ISCO syringe pumps attached to a 500 mL autoclave reactor. The autoclave reactor was then filled with cyclohexane as the organic reaction medium, the organic reaction medium pump was then initiated, and the feed rate set for 275 to 200 g/hour. The autoclave reactor was then brought to a pressure of 1150 psig. Once the oligomerization pressure was achieved, the overhead magnetic stirrer of the autoclave reactor was switched on and stirring at a rate of approximately 1200 rpm was initiated. Heating of the autoclave reactor was then initiated and the autoclave reactor was brought to the desired temperature. The ISCO pumps for the MMAO-3A feed and the ADIFe XIII feed were turned on and the ADIFe XIII feed set to 1.35 mg/hour. The MMAO-3A feed was set to provide the desired Al:fe molar ratio. Thirty minutes after initiating the MMAO-3A feed and the ADIFe XIII feed, ethylene was then introduced to the as the autoclave reactor at a rate of 170 to 250 g/h and hydrogen (if utilized) was introduced to the autoclave reactor at the desired feed rate. The autoclave reactor was then allowed to achieve steady state. Samples were taken of the reaction mixture every 30 minutes.

Figure 3:
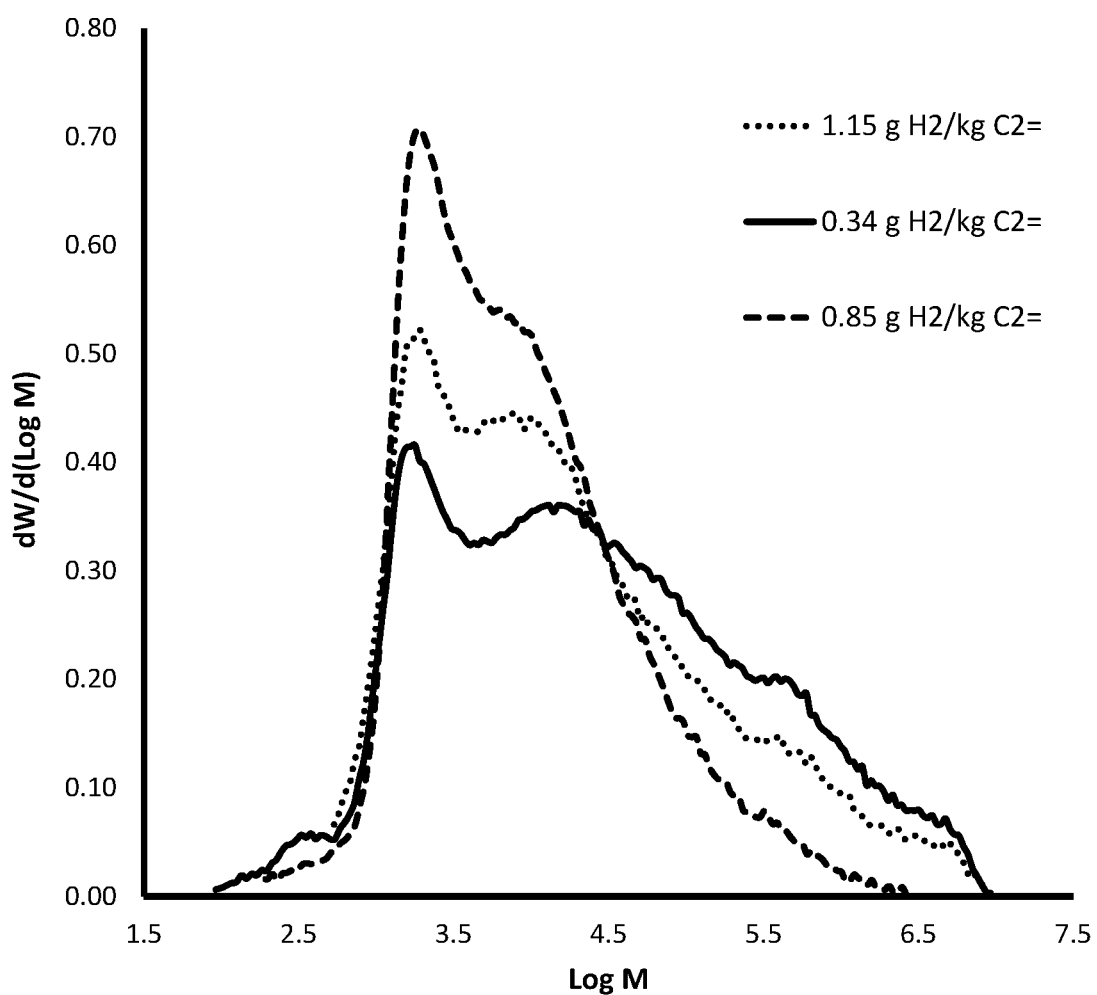
FIG. 3 provides a plot of the molecular weight of the polymer produced in Examples 7, 9, and 10.
Figure 4:
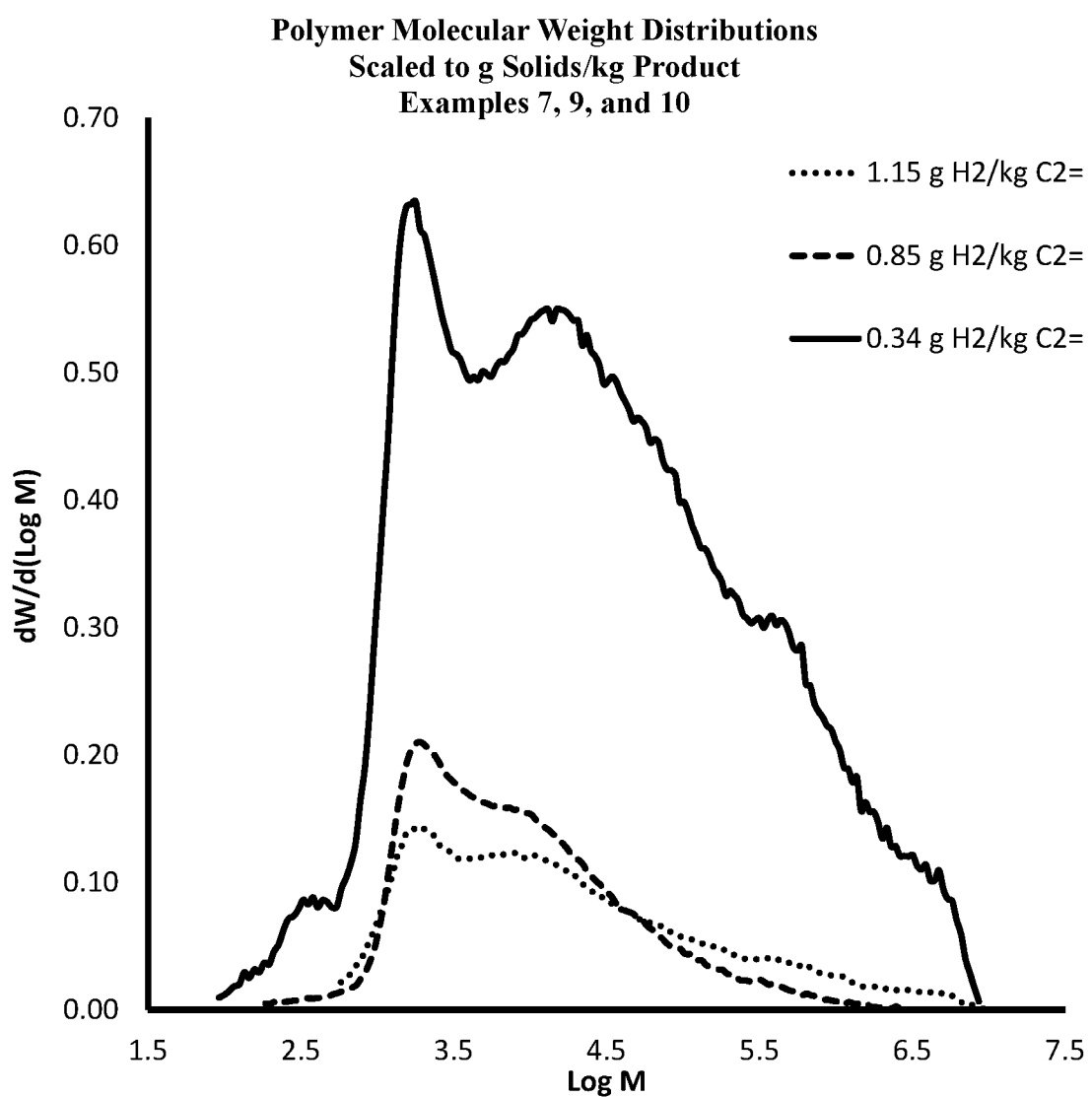
FIG. 4 provides a plot of the molecular weight of the polymer produced in Examples 7, 9, and 10 scaled to the mass of polymer produced per mass of oligomer product produced.

The liquid products were analyzed by a gas chromatograph with a flame ionization detector (FID) detector against the n-nonane internal standard. The solids (waxes>C$_{100}$ and polyethylene) were analyzed by gel permeation chromatography (GPC) using Chevron Phillips Chemicals Company's HDPE polyethylene resin, MARLEX® BHB5003, as the broad molecular weight standard. Calibration samples of MARLEX® BHB5003 can be obtained from Chevron Phillips Chemicals Company, LP. Table 2 details the results of these ethylene oligomerization runs. FIG. 3 provides a plot of the molecular weight of the polymer produced in Examples 7, 9, and 10. FIG. 4 provides a plot of the molecular weight of the polymer produced in Examples 7, 9, and 10 scaled to the mass of polymer produced per mass of oligomer product produced.

TABLE 2

| Example | Temp, °C. | Al, ppm by mass | Al:Fe Molar Ratio | H$_2$, g H$_2$/ kg C$_2$= | Maximum Productivities g Prod/ g bisimine Fe complex | g Prod/ g Al | Reactor Solids Total Solids, g | Wt. % Solids† | C$_{12}$/C$_{10}$ Schulz-Flory K Value |
|---|---|---|---|---|---|---|---|---|---|
| 7 | 62 | 29 | 337 | 0.00 | 99,690 | 7,495 | 4.4 | 0.59 | 0.537 |
| 8 | 56 | 57 | 600 | 0.34 | 82,514 | 3,601 | 11.4 | 2.93 | 0.554 |
| 9 | 56 | 30 | 300 | 0.85 | 98,044 | 8,558 | 4.8 | 0.60 | 0.570 |
| 10 | 52 | 49 | 450 | 1.15 | 87,395 | 5,085 | 4.6 | 0.53 | 0.561 |

†Based upon total Oligomer product

The results of Examples 7-10 demonstrate that increasing H$_2$ relative to ethylene feed reduced the weight percent of generated polymer to effectively zero. Specifically going from 0 added hydrogen to 1.15 g H$_2$/kg ethylene resulted in decreasing the amount of solids from greater than 2 wt. % to less than 1 wt. %. Examples 9 and 10 also demonstrate that the use of hydrogen can affect the molecular weight of the polymer formed in the ethylene oligomerizations. Specifically, FIG. 4 indicates that the addition of hydrogen can reduce the overall molecular weight of the polymer produced and can reduce the high molecular weight tail of the polymer produced in the ethylene oligomerizations.

Example 11

In a nitrogen filled drybox, a toluene stock solution containing 2-[(2,4,6-trimethylphenylimine)methyl]-6-[(3,5-dimethylphenylimine)methyl]pyridine is charged to a 10 mm NMR tube and sealed. Also in the drybox, a 500 mL glass charger is prepared with cyclohexane, n-nonane, and MMAO-3A and is sealed with a rubber septum. The NMR tube and charger are removed from the drybox. The NMR tube is secured to the stirrer shaft of a one liter autoclave reactor with wire in a manner where the glass shatters on starting the stirrer. The autoclave reactor is then sealed and evacuated under high vacuum. The addition funnel is affixed to a charging port on the top of the autoclave reactor. After evacuating the reactor for several minutes, the entire contents of the addition funnel are loaded into the autoclave reactor under vacuum. The autoclave reactor is then degassed with ethylene by carrying out several fill/vent cycles. Following the final vent cycle, the reactor is backfilled with a prescribed pressure of desired amount of hydrogen (individual runs with 0 psi (0 kPa), 10 psi (69 kPa), 25 psi (172 kPa), 40 psi (276 kPa), 60 psi (414 kPa), 80 psi (552 kPa), and 100 psi (689 kPa)). The reactor is then pressurized with ethylene to the desired pressure. Stirring is initiated, breaking the 10 mm NMR tube, and activating the catalyst. Ethylene is fed to the autoclave reactor on demand to maintain the desired for the remainder of the reaction. The reaction temperature is moderated using cooling water passing through internal cooling coils inside the autoclave reactor. The reactor temperature, following the initial exotherm, is at the desired temperature. After 30 min, the reactor is cooled to room temperature and is vented to atmospheric pressure. The reactor is lowered and the liquid contents are measured by way of a graduated cylinder. The contents are allowed to cool and sit for at least 1 h. The contents of the graduated cylinder are then filtered to through a filter frit to isolate the reaction solids. The liquid products are analyzed by gas chromatograph with a flame ionization detector (FID) detector against the n-nonane internal standard. The solids (waxes>$C_{100}$ and polyethylene) are analyzed by gel permeation chromatography (GPC) using Chevron Phillips Chemicals Company's HDPE polyethylene resin, MARLEX® BHB5003, as the broad molecular weight standard. Calibration samples of MARLEX® BHB5003 can be obtained from Chevron Phillips Chemicals Company, LP. The results of these runs demonstrate that increasing $H_2$ relative to ethylene feed reduces the generated polymer as compared to the amount of polymer produced in the $H_2$. The result of these runs also indicates that the addition of hydrogen reduces the overall molecular weight of the polymer produced and the high molecular weight tail of the polymer produced in these ethylene oligomerizations.

We claim:
1. A process comprising:
a) contacting (i) ethylene, (ii) a catalyst system comprising an α-diimine iron salt complex, a pyridine bisimine iron salt complex, or a pyridine bisimine and an iron salt, (iii) hydrogen, and (iv) optionally an organic reaction medium; and
b) forming an oligomer product wherein the oligomer product is formed in the presence of ethylene and hydrogen at a ratio in the range of 0.4 g hydrogen/kg ethylene to 5 g hydrogen/kg ethylene, and wherein 1) the oligomer product has a Schulz-Flory K value from 0.4 to 0.8 and 2) the oligomer product comprises (a) less than 1 wt. % compounds having greater than 70 carbon atoms, (b) less than 1 wt % compounds having a weight average molecular weight greater than 1000 g/mol, or (c) any combination thereof wherein the weight percentage is based on the total weight of the oligomer product.

2. The process of claim 1, wherein each carbon number fraction from $C_4$ to $C_{18}$ of the oligomer product has a paraffin content equal to or less than 2 times the paraffin content of a corresponding carbon number fraction of the oligomer product produced in the absence of hydrogen based on the total weight of the carbon number fraction of the oligomer product.

3. The process of claim 1, wherein the catalyst system comprises the α-diimine iron salt complex, and wherein the α-diimine of the α-diimine iron salt complex comprises i) an α-diimine group, ii) a first imine group consisting of a hydrocarbyl group or substituted hydrocarbyl group attached to a first imine nitrogen atom of the α-diimine group, and iii) a second imine group comprising an iron salt complexing group and a linking group linking the iron salt complexing group to a second imine nitrogen atom of the α-diimine group.

4. The process of claim 1, wherein the catalyst system comprises the α-diimine iron salt complex, and wherein the α-diimine of the α-diimine iron salt complex comprises i) an α-diimine group derived from an aromatic diacyl compound, ii) a first imine group consisting of an aryl group or substituted aryl group, and iii) a second imine group comprising a diarylphosphinyl iron salt complexing group and a —$CH_2CH_2$— linking group linking the iron salt complexing group to a second imine nitrogen atom.

5. The process of claim 1, wherein the catalyst system comprises the α-diimine iron salt complex, and wherein the α-diimine of the α-diimine iron salt complex comprises i) an α-diimine group derived from acenaphthenequinone, phenanthrenequinone, or pyrenequinone, ii) a first imine group consisting of a 2,6-dihydrocarbylphenyl group, and iii) a second imine group comprising a diphenylphosphinyl iron salt complexing group or a disubstituted phenyl)phosphinyl iron complexing group and a —$CH_2CH_2$— linking group linking the iron salt complexing group to a second imine nitrogen atom.

6. The process of claim 1, wherein the catalyst system comprises the α-diimine iron salt complex, and wherein the iron salt of the α-diimine iron salt complex comprises an iron halide, an iron acetylacetonate, an iron carboxylate, or any combination thereof.

7. The process of claim 1, wherein the catalyst system comprises the α-diimine iron salt complex, and wherein the α-diimine iron salt complex has a structure selected from the group consisting of

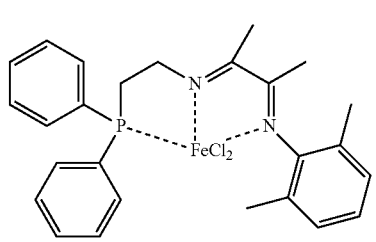

ADIFe I

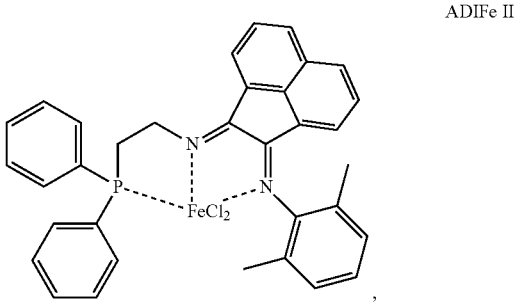

ADIFe II

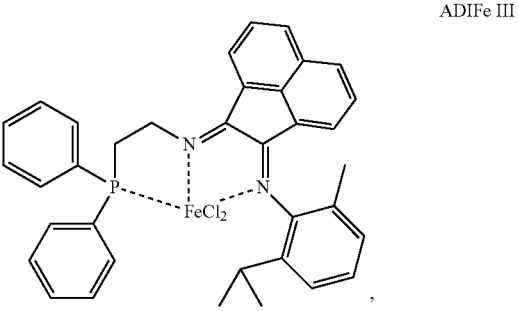

ADIFe III

ADIFe IV

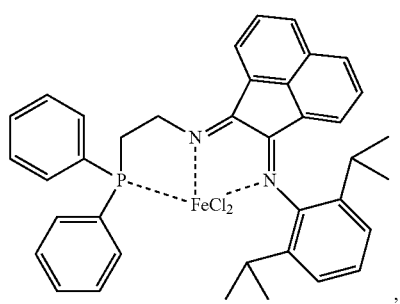

ADIFe V

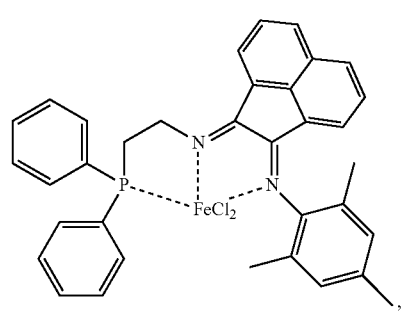

ADIFe VI

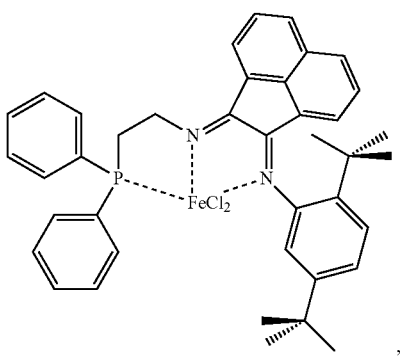

ADIFe VII

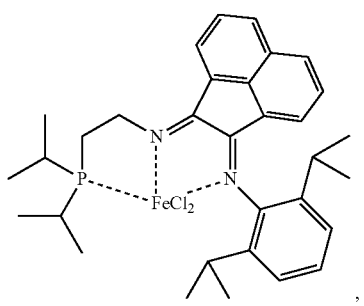

ADIFe VIII

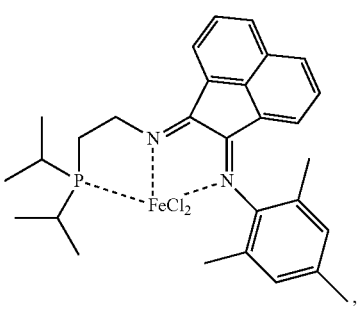

ADIFe IX

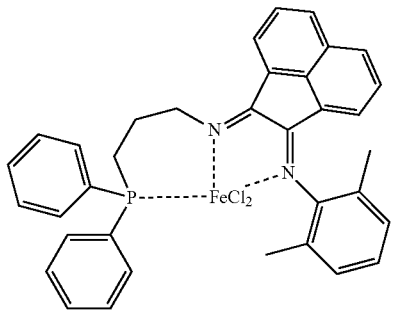

ADIFe X

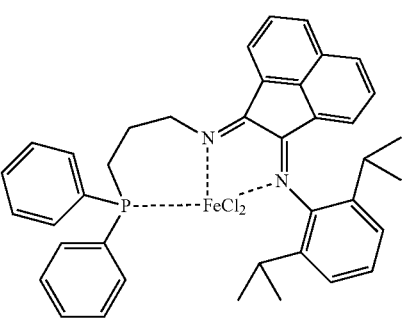

ADIFe XII

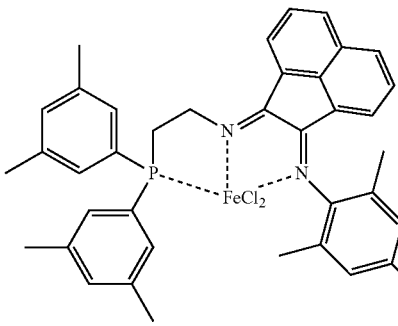

, and

ADIFe XIII

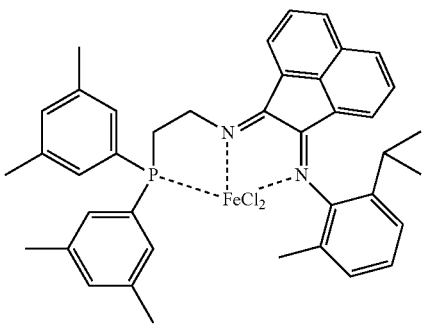

8. The process of claim 1, wherein the catalyst system comprises the pyridine bisimine iron salt complex or the pyridine bisimine and the iron salt, and wherein the pyridine bisimine or the pyridine bisimine of the pyridine bisimine iron salt complex comprises i) a 2,6-bis[(arylimine)hydrocarbyl]pyridine wherein the aryl groups can be the same or different, ii) a bis[(substituted arylimine)hydrocarbyl]pyridine wherein the substituted aryl groups can be the same or different, or iii) an [(arylimine)hydrocarbyl],[(substituted arylimine)hydrocarbyl]pyridine.

9. The process of claim 1, wherein the catalyst system comprises the pyridine bisimine iron salt complex or the pyridine bisimine and the iron salt, and wherein the pyridine bisimine or the pyridine bisimine of the pyridine bisimine iron salt complex is selected from the group consisting of 2,6-bis[(phenylimine) methyl]pyridine, 2,6-bis[(2-methylphenylimine)methyl]pyridine, 2,6-bis[(2-ethylphenylimine) methyl]pyridine, 2,6-bis[(2-isopropylphenylimine)methyl] pyridine, 2,6-bis[(2,4-dimethylphenylimine)methyl] pyridine, 2,6-bis[(2,6-diethylphenylimine)methyl]pyridine, 2-[(2,4,6-trimethylphenylimine)methyl]-6-[(4-methylphenylimine)methyl]pyridine, 2-[(2,4,6-trimethylphenylimine) methyl]-6-[(3,5-dimethylphenylimine)methyl]pyridine, and 2-[(2,4,6-trimethylphenylimine)methyl]-6-[(4-t-butylphenylimine)methyl]pyridine.

10. The process of claim 1, wherein the catalyst system further comprises an organoaluminum compound.

11. The process of claim 10, wherein the organoaluminum compound comprises an aluminoxane.

12. The process of claim 1, wherein the oligomer product comprises a $C_6$ oligomer product having a 1-hexene content of at least 98.5 wt. %.

13. The process of claim 1, wherein the oligomer product comprises a $C_8$ olefin oligomer product having a 1-octene content of at least 98 wt. %.

14. The process of claim 1, wherein the oligomer product comprises a $C_{10}$ oligomer product having a 1-decene content of at least 97.5 wt. %.

15. The process of claim 1, wherein the oligomer product comprises a $C_{12}$ oligomer product having a 1-dodecene content of at least 96.5 wt. %.

16. The process of claim 1, wherein the catalyst system further comprises an aluminoxane and wherein b) further comprises forming the oligomer product at i) a temperature in a range of 0° C. to 200° C., ii) an ethylene partial pressure in a range of 50 psi (344 KPa) to 5000 psi (34.5 MPa), iii) an iron of the iron salt concentration, an iron of the pyridine bisimine iron salt complex concentration or an iron of the α-diimine iron salt complex concentration in a range of $1\times10^{-6}$ mmol Fe/kg to $1\times10^{-1}$ mmol Fe/kg, iv) an Al:Fe molar ratio in the range of 100:1 to 5,000:1, and v) optionally an ethylene to organic reaction medium mass ratio in a range of 0.8:1 to 45:1.

17. A process comprising:
a) contacting (i) ethylene, (ii) a catalyst system comprising an α-diimine iron salt complex, a pyridine bisimine iron salt complex, or a pyridine bisimine and an iron salt, (iii) hydrogen, and (iv) optionally an organic reaction medium; and
b) forming an oligomer product wherein the oligomer product is formed in the presence of ethylene and hydrogen at a ratio in the range of 0.4 g hydrogen 1 kg ethylene to 5 g hydrogen/kg ethylene, and wherein 1) the oligomer product has a Schulz-Flory K value from 0.4 to 0.8, and 2) each carbon number fraction from $C_4$ to $C_{18}$ of the oligomer product has a paraffin content equal to or less than 2 times the paraffin content of a corresponding carbon number fraction of the oligomer product produced in the absence of hydrogen based on the total weight of the carbon number fraction of the oligomer product.

18. The process of claim 17, wherein the oligomer product comprises (a) less than 1 wt. % compounds having greater than 70 carbon atoms, (b) less than 1 wt. % compounds having a weight average molecular weight greater than 1000 g/mole, or (c) any combination thereof wherein the weight percentage is based on the total weight of the oligomer product.

19. The process of claim 17, wherein the catalyst system further comprises an aluminoxane and wherein b) further comprises forming the oligomer product at i) a temperature in a range of 0° C. to 200° C., ii) an ethylene partial pressure in a range of 50 psi (344 KPa) to 5000 psi (34.5 MPa), iii) an iron of the iron salt concentration, an iron of the pyridine bisimine iron salt complex concentration or an iron of the α-diimine iron salt complex concentration in a range of $1\times10^{16}$ mmol Fe/kg to $1\times10^{11}$ mmol Fe/kg, iv) an Al:Fe molar ratio in the range of 100:1 to 5,000:1, and v) optionally an ethylene to organic reaction medium mass ratio in a range of 0.8:1 to 4.5:1.

20. A process comprising:
a) contacting (i) ethylene, (ii) a catalyst system comprising an α-diimine iron salt complex, a pyridine bisimine iron salt complex, or a pyridine bisimine and an iron salt, (iii) hydrogen, and (iv) optionally an organic reaction medium; and
b) forming an oligomer product wherein the oligomer product is formed in the presence of ethylene and hydrogen at a ratio in the range of 0.4 g hydrogen/kg ethylene to 5 g hydrogen/kg ethylene, and wherein the oligomer product has a Schulz-Flory K value of from 0.4 to 0.8 and a Schulz-Flory K value that is within ±5% of an oligomer product produced in the absence of hydrogen.

21. The process of claim 20, wherein each carbon number fraction from $C_4$ to $C_{18}$ of the oligomer product has a paraffin content of equal to or less than 2 times the paraffin content of a corresponding carbon number fraction of the oligomer product produced in the absence of hydrogen based on the total weight of the carbon number fraction of the oligomer product.

22. The process of claim 20, wherein the oligomer product comprises (a) less than 1 wt. % compounds having greater than 70 carbon atoms, (b) less than 1 wt. % compounds having a weight average molecular weight greater than 1000 g/mole, or (c) any combination thereof wherein the weight percentage is based on the total weight of the oligomer product.

23. The process of claim 20, wherein the catalyst system further comprises an aluminoxane and wherein b) further comprises forming the oligomer product at i) a temperature in a range of 0° C. to 200° C., ii) an ethylene partial pressure in a range of 50 psi (344 KPa) to 5000 psi (34.5 MPa), iii) an iron of the iron salt concentration, an iron of the pyridine bisimine iron salt complex concentration or an iron of the α-diimine iron salt complex concentration in a range of $1\times10^{-6}$ mmol Fe/kg to $1\times10^{-1}$ mmol Fe/kg, iv) an Al:Fe molar ratio in the range of 100:1 to 5,000:1, and v) optionally an ethylene to organic reaction medium mass ratio in a range of 0.8:1 to 4.5:1.

* * * * *

UNITED STATES PATENT AND TRADEMARK OFFICE
CERTIFICATE OF CORRECTION

PATENT NO. : 10,604,457 B2
APPLICATION NO. : 15/394317
DATED : March 31, 2020
INVENTOR(S) : Steven Bischof et al.

It is certified that error appears in the above-identified patent and that said Letters Patent is hereby corrected as shown below:

In the Claims

Claim 19, Column 74, Line 15, replace "$1\times10^{16}$" with the following --$1\times10^{-6}$--

Claim 19, Column 74, Line 15, replace "$1\times10^{11}$" with the following --$1\times10^{-1}$--

Signed and Sealed this
Twenty-eighth Day of June, 2022

Katherine Kelly Vidal
*Director of the United States Patent and Trademark Office*